(12) United States Patent
Müller et al.

(10) Patent No.: US 6,838,415 B1
(45) Date of Patent: Jan. 4, 2005

(54) SUBSTITUTED BENZOYLISOXAZOLES AND THE USE THEREOF AS HERBICIDES

(75) Inventors: Klaus-Helmut Müller, Düsseldorf (DE); Stefan Lehr, Langenfeld (DE); Otto Schallner, Monheim (DE); Hans-Georg Schwarz, Langenfeld (DE); Heinz-Jürgen Wroblowsky, Langenfeld (DE); Mark Wilhelm Drewes, Langenfeld (DE); Dieter Feucht, Monheim (DE); Rolf Pontzen, Leichlingen (DE); Ingo Wetcholowsky, Cond. Estancia Marambaia (BR)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/980,666

(22) PCT Filed: Apr. 20, 2000

(86) PCT No.: PCT/EP00/03608

§ 371 (c)(1),
(2), (4) Date: Nov. 2, 2001

(87) PCT Pub. No.: WO00/68227

PCT Pub. Date: Nov. 16, 2000

(30) Foreign Application Priority Data

May 6, 1999 (DE) .......................................... 199 20 791

(51) Int. Cl.$^7$ .................... C07D 413/10; C07D 249/12; A01N 43/80

(52) U.S. Cl. ........................ 504/225; 504/228; 504/242; 504/243; 504/265; 504/269; 504/271; 544/137; 544/180; 544/215; 544/310; 544/318; 548/144; 548/210; 548/221; 548/248

(58) Field of Search ................................ 544/137, 180, 544/215, 310, 318; 548/144, 210, 221, 248; 504/225, 228, 242, 243, 265, 269, 271

(56) References Cited

U.S. PATENT DOCUMENTS

| | | | |
|---|---|---|---|
| 3,742,014 A | 6/1973 | Grivsky .................. 260/465 B |
| 3,978,127 A | 8/1976 | Engelhardt et al. ... 260/570.5 R |
| 4,542,127 A | 9/1985 | Hitzel et al. ................. 514/161 |
| 4,837,333 A | 6/1989 | Manley et al. .............. 548/341 |
| 5,171,748 A | 12/1992 | Roberts et al. ............. 514/381 |
| 5,185,351 A | 2/1993 | Finkelstein et al. ......... 514/341 |
| 5,189,033 A | 2/1993 | Tucker ........................ 514/211 |
| 5,371,063 A | 12/1994 | Cramp et al. ............... 504/270 |
| 5,374,606 A | 12/1994 | Cramp et al. ............... 504/270 |
| 5,378,681 A | 1/1995 | Schallner et al. ........... 504/273 |
| 5,476,946 A | 12/1995 | Linker et al. ............... 504/373 |
| 5,489,570 A | 2/1996 | Geach et al. ............... 504/270 |
| 5,554,580 A | 9/1996 | Fischer et al. .............. 504/281 |
| 5,650,533 A | 7/1997 | Roberts et al. ................ 560/17 |

(List continued on next page.)

FOREIGN PATENT DOCUMENTS

| | | |
|---|---|---|
| CA | 2119673 | 9/1994 |
| CA | 2183641 | 8/1995 |
| EP | 0 093 488 A2 | 11/1983 |
| EP | 487 357 | 5/1992 |
| EP | 0 560 483 A1 | 9/1993 |
| EP | 0 527 037 B1 | 10/1996 |
| EP | 0 527 036 B1 | 11/1996 |
| WO | 95/22903 | 8/1995 |
| WO | 95/31446 | 11/1995 |
| WO | 96/26192 | 8/1996 |
| WO | 97/27187 | 7/1997 |
| WO | 99/03856 | 1/1999 |

Primary Examiner—Deepak Rao
(74) Attorney, Agent, or Firm—Richard E. L. Henderson; Raymond J. Harmuth

(57) ABSTRACT

The invention relates to novel substituted benzoylisoxazoles of the general formula (I),

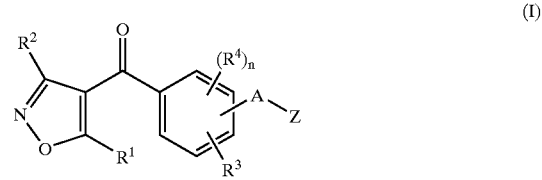

in which n represents the number 0, 1, 2 or 3, A represents a single bond or represents alkanediyl (alkylene), $R^1$ represents hydrogen or represents in each case optionally substituted alkyl, alkenyl or cycloalkyl, $R^2$ represents hydrogen, cyano, carbamoyl, halogen, or represents in each case optionally substituted alkyl, alkylcarbonyl, alkoxy, alkoxycarbonyl or alkylthio, alkylsulphinyl or alkylsulphonyl, $R^3$ represents hydrogen, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, $R^4$ represents nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, and Z represents an optionally substituted 4- to 12-membered, saturated or unsaturated, monocyclic or bicyclic, heterocyclic grouping which contains 1 to 4 hetero atoms (up to 4 nitrogen atoms and optionally—alternatively or additionally—one oxygen atom or one sulphur atom, or one SO grouping or one $SO_2$ grouping) and which additionally contains one to three oxo groups (C=O) and/or thioxo groups (C=S) as components of the heterocycle, and to processes for their preparation and to their use as herbicides.

17 Claims, No Drawings

U.S. PATENT DOCUMENTS

| | | | |
|---|---|---|---|
| 5,656,573 A | 8/1997 | Roberts et al. | 504/271 |
| 5,663,362 A | 9/1997 | Haas et al. | 548/263.2 |
| 5,747,424 A | 5/1998 | Roberts et al. | 504/271 |
| 5,834,402 A | 11/1998 | Von Deyn et al. | 504/271 |
| 5,859,283 A | 1/1999 | Cramp | 560/124 |
| 5,863,865 A | 1/1999 | Lee et al. | 504/271 |
| 5,880,147 A | 3/1999 | Yoshida et al. | 514/452 |
| 6,040,339 A | 3/2000 | Yoshida et al. | 514/485 |
| 6,063,789 A | 5/2000 | Hamley et al. | 514/301 |
| 6,297,198 B1 | 10/2001 | Lee | 504/271 |
| 6,624,121 B1 * | 9/2003 | Yanagi et al. | 504/261 |

* cited by examiner

SUBSTITUTED BENZOYLISOXAZOLES AND THE USE THEREOF AS HERBICIDES

The invention relates to novel substituted benzoylisoxazoles, to processes for their preparation and to their use as herbicides.

It is already known that certain substituted benzoylisoxazoles have herbicidal properties (cf. EP-A-418 175, EP-A-487 357, EP-A-527 036, EP-A-527 037, EP-A-560 483, EP-A-609 797, EP-A-609 798, EP-A-636 622, U.S. Pat. No. 5 834402, U.S. Pat. No. 5,863,865, WO-A-96/26192, WO-A-97/27187, WO-A-97/43270, WO-A-99/03856). However, the activity of these compounds is not entirely satisfactory.

This invention, accordingly, provides the novel compounds of the general formula (I),

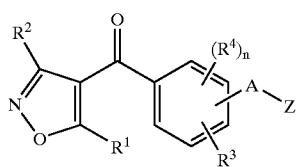

(I)

in which
- n represents the number 0, 1, 2 or 3,
- A represents a single bond or represents alkanediyl (alkylene),
- $R^1$ represents hydrogen or represents in each case optionally substituted alkyl, alkenyl or cycloalkyl,
- $R^2$ represents hydrogen, cyano, carbamoyl, halogen, or represents in each case optionally substituted alkyl, alkylcarbonyl, alkoxy, alkoxycarbonyl, alkylthio, alkylsulphinyl or alkylsulphonyl.
- $R^3$ represents hydrogen, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl,
- $R^4$ represents nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, and
- Z represents an optionally substituted 4- to 12-membered, saturated or unsaturated, monocyclic or bicyclic, heterocyclic grouping which contains 1 to 4 hetero atoms (up to 4 nitrogen atoms and optionally—alternatively or additionally—one oxygen atom or one sulphur atom, or one SO grouping or one $SO_2$ grouping) and which additionally contains one to three oxo groups (C=O) and/or thioxo groups (C=S) as components of the heterocycle.

In the definitions, the hydrocarbon chains, such as alkyl or alkanediyl—including in combination with hetero atoms, such as alkoxy—are in each case straight-chain or branched.

n preferably represents the number 0, 1 or 2.

A preferably represents a single bond or represents alkanediyl (alkylene) having 1 to 4 carbon atoms.

$R^1$ preferably represents hydrogen, represents optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl having 1 to 6 carbon atoms, represents optionally cyano- or halogen-substituted alkenyl having 2 to 6 carbon atoms, or represents optionally cyano-, halogen- or $C_1$–$C_4$-alkyl-substituted cycloalkyl having 3 to 6 carbon atoms.

$R^2$ preferably represents hydrogen, cyano, carbamoyl, halogen, represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkylcarbonyl, alkoxy or alkoxycarbonyl having in each case up to 6 carbon atoms, or represents in each case optionally halogen-substituted alkylthio, alkylsulphinyl or alkylsulphonyl having in each case 1 to 6 carbon atoms.

$R^3$ preferably represents hydrogen, nitro, cyano, carboxyl, carbamoyl, thio-carbamoyl, halogen, represents in each case optionally halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl or alkylsulphonyl having in each case up to 4 carbon atoms in the alkyl groups, or represents alkylamino, dialkylamino or dialkylaminosulphonyl having in each case up to 4 carbon atoms in the alkyl groups.

$R^4$ preferably represents nitro, cyano, carboxyl, carbamoyl, thiocarbamoyl, halogen, represents in each case optionally halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl or alkylsulphonyl having in each case up to 4 carbon atoms in the alkyl groups, or represents alkylamino, dialkylamino or dialkylaminosulphonyl having in each case up to 4 carbon atoms in the alkyl groups, and Z preferably represents one of the heterocyclic groupings below

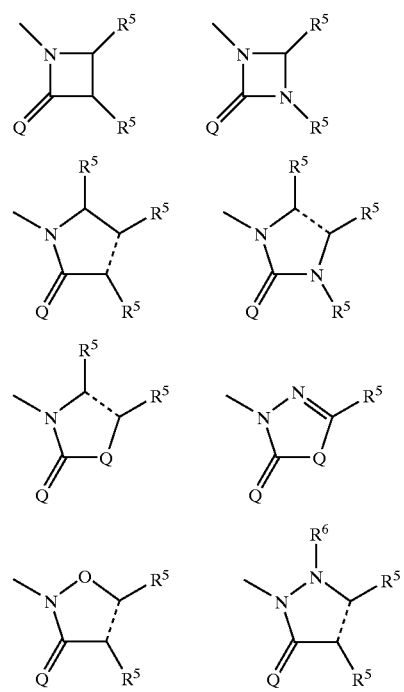

-continued

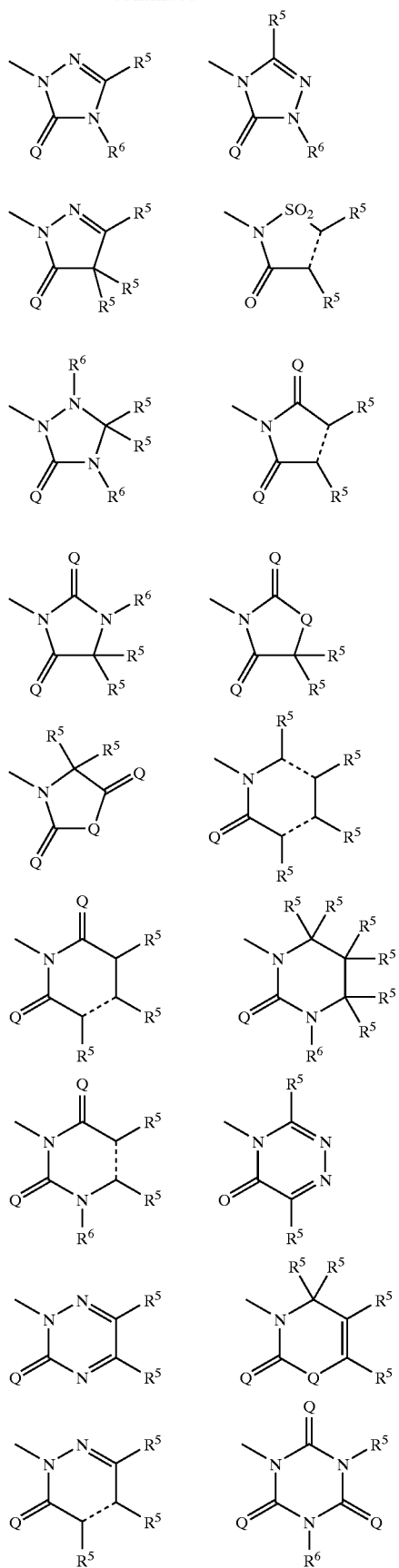

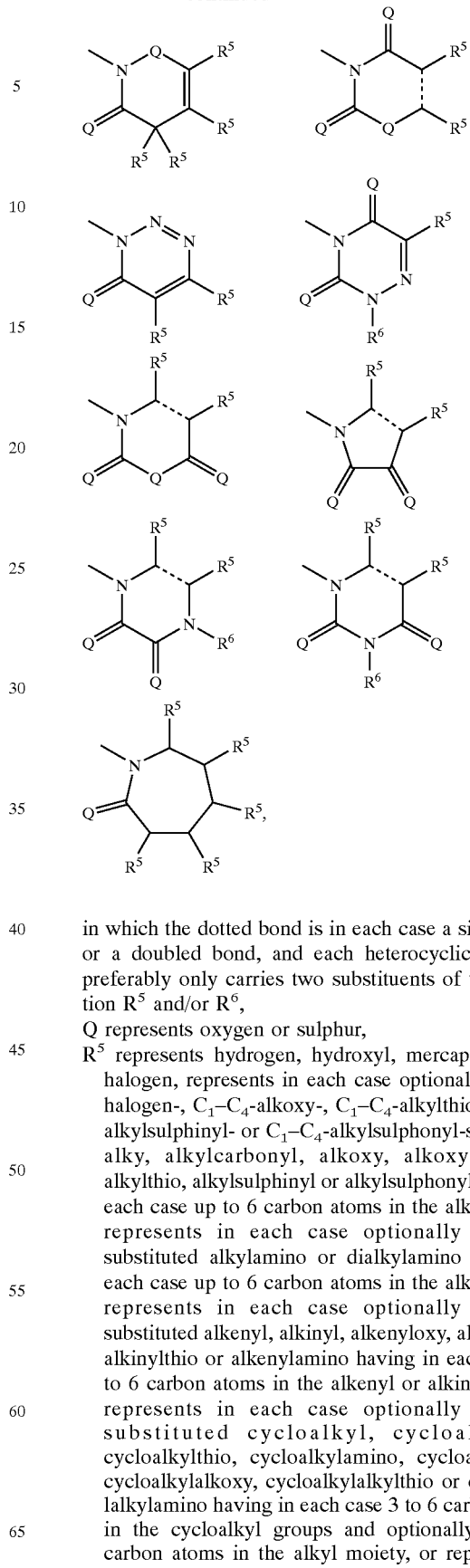

in which the dotted bond is in each case a single bond or a doubled bond, and each heterocyclic grouping preferably only carries two substituents of the definition $R^5$ and/or $R^6$, Q represents oxygen or sulphur, $R^5$ represents hydrogen, hydroxyl, mercapto, cyano, halogen, represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alky, alkylcarbonyl, alkoxy, alkoxycarbonyl, alkylthio, alkylsulphinyl or alkylsulphonyl having in each case up to 6 carbon atoms in the alkyl groups, represents in each case optionally halogen-substituted alkylamino or dialkylamino having in each case up to 6 carbon atoms in the alkyl groups, represents in each case optionally halogen-substituted alkenyl, alkinyl, alkenyloxy, alkenylthio, alkinylthio or alkenylamino having in each case up to 6 carbon atoms in the alkenyl or alkinyl groups, represents in each case optionally halogen-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and optionally up to 4 carbon atoms in the alkyl moiety, or represents in each case optionally halogen-, $C_1$–$C_4$-alkyl- or $C_1$–$C_4$-alkoxy-substituted phenyl, phenyloxy, phenylthio, phenyl-amino, benzyl, benzyloxy, benzylthio or benzylamino, represents pyrrolidino, piperidino or morpholino, or—if two adjacent radicals $R^5$ and $R^5$ are located at a double bond—also together with the adjacent radical $R^5$ represents a benzo grouping, and $R^6$ represents hydrogen, hydroxyl, amino, alkylidenamino having up to 4 carbon atoms, represents in each case optionally halogen- or $C_1$–$C_4$-alkoxy-substituted alkyl, alkoxy, alkylamino, dialkylamino or alkanoylamino having in each case up to 6 carbon atoms in the alkyl groups, represents in each case optionally halogen-substituted alkenyl, alkinyl or alkenyloxy having in each case up to 6 carbon atoms in the alkenyl or alkinyl groups, represents in each case optionally halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents in each case optionally halogen-, $C_1$–$C_4$-alkyl- or $C_1$–$C_4$-alkoxy-substituted phenyl or benzyl, or together with an adjacent radical $R^5$ or $R^6$ represents optionally halogen- or $C_1$–$C_4$-alkyl-substituted alkanediyl having 3 to 5 carbon atoms, where the individual radicals $R^5$ and $R^6$—if a plurality of them are attached to the same heterocyclic grouping—can have identical or different meanings within the scope of the above definition.

Q preferably represents oxygen (O).

$R^5$ preferably represents hydrogen, hydroxyl, mercapto, cyano, fluorine, chlorine, bromine, iodine, represents in each case optionally fluorine-, chlorine-, methoxy-, ethoxy-, n- or i-propoxy-, n-, i-, s- or t-butoxy-, methylthio-, ethylthio-, n- or i-propylthio-, n-, i-, s- or t-butylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, n-, i-, s- or t-butylamino, dimethylamino, diethylamino, di-n-propylamino or di-i-propylamino, represents in each case optionally fluorine-and/or chlorine-substituted ethenyl, propenyl, butenyl, ethinyl, propinyl, butinyl, propenyloxy, butenyloxy, propenylthio, butenylthio, propenylamino or butenylamino, represents in each case optionally fluorine- and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluorine-, chlorine-, methyl-, ethyl-, n- or i-propyl-, n-, i-, s- or t-butyl-, methoxy-, ethoxy-, n- or i-propoxy-substituted phenyl, phenyloxy, phenylthio, phenylamino, benzyl, benzyloxy, benzylthio or benzylamino, represents pyrrolidino, piperidino or morpholino, or—if two adjacent radicals $R^5$ and $R^5$ are located at a double bond—together with the adjacent radical $R^5$ also represents a benzo grouping.

$R^6$ preferably represents hydrogen, hydroxyl, amino, represents in each case optionally fluorine- and/or chlorine-, methoxy- or ethoxy-substituted methyl, ethyl, n- or i-propyl, n-, i- or s-butyl, methoxy, ethoxy, n- or i-propoxy, methylamino, ethylamino or dimethylamino, represents in each case optionally fluorine- and/or chlorine-substituted ethenyl, propenyl, ethinyl, propinyl or propenyloxy, represents in each case optionally fluorine- and/or chlorine-substituted cyclopropyl, cyclobutyl, cyclopentyl, cyclohexyl, cyclopropylmethyl, cyclobutylmethyl cyclopontylmethyl, cyclohexylmethyl, or represents in each case optionally fluorine-, chlorine-, methyl-, ethyl-, n- or i-propyl-, n-, i-, s- or t-butyl-, methoxy-, ethoxy-, n- or i-propoxy-substituted phenyl or benzyl, or together with an adjacent radical $R^5$ or $R^6$ represents in each case optionally methyl- and/or ethyl-substituted propane-1,3-diyl (trimethylene) or butane-1,4-diyl (tetramethylene).

A particularly preferably represents a single bond, methylene, ethylidene (ethane-1,1-diyl) or dimethylene (ethane-1,2-diyl).

$R^1$ particularly preferably represents hydrogen, represents in each case optionally fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, represents in each case optionally fluorine-, chlorine- or bromine-substituted propenyl, butenyl, propinyl or butinyl, or represents in each case optionally cyano-, fluorine-, chlorine-, bromine-, methyl- or ethyl-substituted cyclopropyl, cyclobutyl, cyclopentyl or cyclohexyl.

$R^2$ particularly preferably represents hydrogen, cyano, carbamoyl, fluorine, chlorine, bromine, represents in each case optionally cyano-, fluorine-, chlorine-, methoxy- or ethoxy-substituted methyl, ethyl, n- or i-propyl, acetyl, propionyl, n- or i-butyroyl, methoxy, ethoxy, n- or i-propoxy, methoxycarbonyl, ethoxycarbonyl, n- or i-propoxycarbonyl, or represents in each case optionally fluorine- and/or chlorine-substituted methylthio, ethylthio, n- or i-propylthio, methylsulphinyl, ethylsulphinyl, n- or i-propylsulphinyl, methylsulphonyl or ethylsulphonyl.

$R^3$ particularly preferably represents hydrogen, nitro, cyano, carboxyl, carbamoyl, thiocarbamoyl, fluorine, chlorine, bromine, iodine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl.

$R^4$ particularly preferably represents nitro, cyano, carboxyl, carbamoyl, thiocarbamoyl, fluorine, chlorine, bromine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-; i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl.

Z particularly preferably represents the heterocyclic groupings

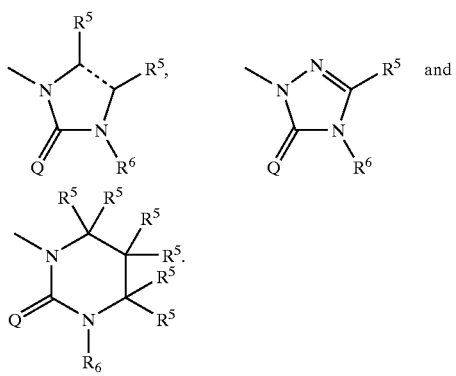

$R^5$ particularly preferably represents hydrogen, hydroxyl, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, fluoroethyl, chloroethyl, difluoroethyl, dichloroethyl, fluoro-n-propyl, fluoro-i-propyl, chloro-n-propyl, chloro-i-propyl, methoxymethyl, ethoxymethyl, methoxyethyl, ethoxyethyl, methoxy, ethoxy, n- or i-propoxy, n-, i-, s- or t-butoxy, fluoroethoxy, chloroethoxy, difluoroethoxy, dichloroethoxy, trifluoroethoxy, trichloroethoxy, chlorofluoroethoxy, chlorodifluoroethoxy, fluorodichloroethoxy, methylthio, ethylthio, n- or i-propylthio, fluoroethylthio, chloroethylthio, difluoroethylthio, dichloroethylthio, chlorofluoroethylthio, chlorodifluoroethylthio, fluorodichloroethylthio, methylsulphinyl, ethylsulphinyl, n- or i-propylsulphinyl, methylsulphonyl, ethylsulphonyl, n- or i-propylsulphonyl, dimethylamino, propenylthio, butenylthio, propinylthio, butinylthio, cyclopropyl, cyclopropylmethyl, cyclopropylmethoxy, phenyl or phenoxy.

$R^6$ particularly preferably represents amino, methyl, ethyl, n- or i-propyl, n-, i-, s- or t-butyl, methoxy, ethoxy, methylamino, dimethylamino, cyclopropyl or cyclopropylmethyl, or together with $R^5$ represents propane-1,3-diyl (trimethylene), butane-1,4-diyl (tetramethylene) or pentane-1,5-diyl (pentamethylene).

A very particularly preferably represents a single bond or represents methylene.

$R^1$ very particularly preferably represents hydrogen, represents in each case optionally fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, i-, s- or t-butyl, or represents optionally cyano-, fluorine-, chlorine-, bromine-, methyl- or ethyl-substituted cyclopropyl.

$R^2$ very particularly preferably represents hydrogen, cyano, carbamoyl, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxycarbonyl, ethoxycarbonyl, n- or i-propoxycarbonyl, or represents in each case optionally fluorine- and/or chlorine-substituted methylthio, ethylthio, n- or i-propylthio, methylsulphinyl, ethylsulphinyl, methylsulphonyl or ethylsulphonyl.

$R^3$ very particularly preferably represents hydrogen, nitro, cyano, fluorine, chlorine, bromine, iodine, methyl, ethyl, trifluoromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl.

$R^4$ very particularly preferably represents nitro, cyano, fluorine, chlorine, bromine, methyl, ethyl, trifluoromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl.

A most preferably represents methylene.

$R^1$ most preferably represents cyclopropyl.

$R^2$ most preferably represents hydrogen, methoxycarbonyl or ethoxycarbonyl $R^3$ most preferably represents chlorine, bromine, cyano, trifluoromethyl or methylsulphonyl.

$R^4$ most preferably represents hydrogen, cyano, chlorine, nitro, methyl, trifluoromethyl, methoxy or methylsulphonyl.

Preference according to the invention is given to those compounds of the formula (I) which contain a combination of the meanings listed above as being preferred.

Particular preference according to the invention is given to those compounds of the formula (I) which contain a combination of the meanings listed above as being particularly preferred.

Very particular preference according to the invention is given to those compounds of the formula (I) which contain a combination of the meanings listed above as being very particularly preferred.

Most preference according to the invention is given to those compounds of the formula (I) which contain a combination of the meanings listed above as being most preferred.

Among the meanings given as preferred, particularly preferred, very particularly preferred or most preferred, still greater emphasis is given to the compounds of the general formula (IA)

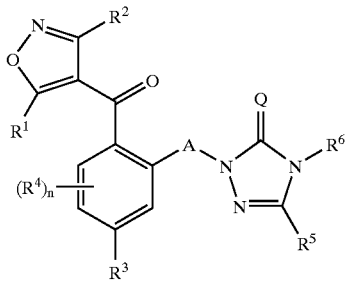
(IA)

in which
n, A, Q, $R^1$, $R^2$, $R^3$, $R^4$, $R^5$ and $R^6$ are each as defined above, with very particular emphasis on the compounds of the formula (IA) in which A represents methylene.

Moreover, among the meanings given as being preferred, particularly preferred, very particularly preferred or most particularly preferred, still greater emphasis is given to the compounds of the general formula (IB)

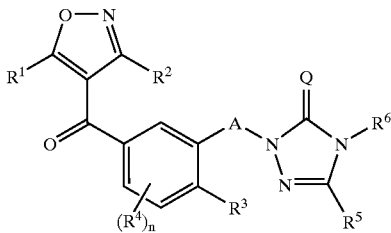
(IB)

in which.
n, A, Q, $R^1$, $R^2$, $R^3$, $R^4$, $R^5$ and $R^6$ are each as defined above.

Furthermore, among the meanings given as being preferred, particularly preferred, very particularly preferred or most preferred, still greater emphasis is given to those compounds of the general formula (IC)

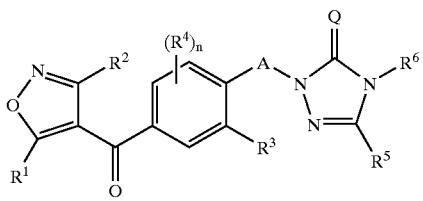
(IC)

in which
n, A, Q, $R^1$, $R^2$, $R^3$, $R^4$, $R^5$ and $R^6$ are each as defined above.

The abovementioned general or preferred radical definitions apply both to the end products of the formula (I) and, correspondingly, to the starting materials or intermediates required in each case for the preparation. These radical definitions can be combined with one another as desired, i.e. including combinations between the given preferred ranges.

Examples of compounds of the general formula (I) according to the invention are listed in the groups below.

Group 1

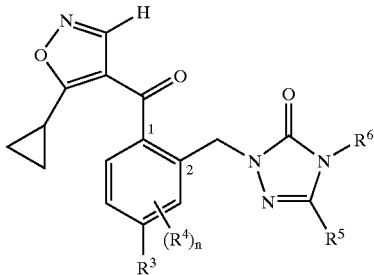
(IA-1)

Here, $R^3$, $(R^4)_n$, $R^5$ and $R^6$ each have, for example, the meanings given in the table below:

| $R^3$ | (position-) $(R^4)_n$ | $R^5$ | $R^6$ |
|---|---|---|---|
| H | — | $CF_3$ | $CH_3$ |
| F | — | $CF_3$ | $CH_3$ |
| Cl | — | $CF_3$ | $CH_3$ |
| Br | — | $CF_3$ | $CH_3$ |
| I | — | $CF_3$ | $CH_3$ |
| $NO_2$ | — | $CF_3$ | $CH_3$ |
| CN | — | $CF_3$ | $CH_3$ |
| $CH_3$ | — | $CF_3$ | $CH_3$ |
| $OCH_3$ | — | $CF_3$ | $CH_3$ |
| $CF_3$ | — | $CF_3$ | $CH_3$ |
| $OCHF_2$ | — | $CF_3$ | $CH_3$ |
| $OCF_3$ | — | $CF_3$ | $CH_3$ |
| $SO_2CH_3$ | — | $CF_3$ | $CH_3$ |
| H | — | $OCH_3$ | $CH_3$ |
| F | — | $OCH_3$ | $CH_3$ |
| Cl | — | $OCH_3$ | $CH_3$ |
| Br | — | $OCH_3$ | $CH_3$ |
| I | — | $OCH_3$ | $CH_3$ |
| $NO_2$ | — | $OCH_3$ | $CH_3$ |
| CN | — | $OCH_3$ | $CH_3$ |
| $CH_3$ | — | $OCH_3$ | $CH_3$ |
| $OCH_3$ | — | $OCH_3$ | $CH_3$ |
| $CF_3$ | — | $OCH_3$ | $CH_3$ |
| $OCHF_2$ | — | $OCH_3$ | $CH_3$ |
| $OCF_3$ | — | $OCH_3$ | $CH_3$ |
| $SO_2CH_3$ | — | $OCH_3$ | $CH_3$ |
| H | — | $SCH_3$ | $CH_3$ |
| F | — | $SCH_3$ | $CH_3$ |
| Cl | — | $SCH_3$ | $CH_3$ |
| Br | — | $SCH_3$ | $CH_3$ |
| I | — | $SCH_3$ | $CH_3$ |
| $NO_2$ | — | $SCH_3$ | $CH_3$ |
| CN | — | $SCH_3$ | $CH_3$ |
| $CH_3$ | — | $SCH_3$ | $CH_3$ |
| $OCH_3$ | — | $SCH_3$ | $CH_3$ |
| $CF_3$ | — | $SCH_3$ | $CH_3$ |
| $OCHF_2$ | — | $SCH_3$ | $CH_3$ |
| $OCF_3$ | — | $SCH_3$ | $CH_3$ |
| $SO_2CH_3$ | — | $SCH_3$ | $CH_3$ |
| H | — | $OC_2H_5$ | $CH_3$ |
| F | — | $OC_2H_5$ | $CH_3$ |
| Cl | — | $OC_2H_5$ | $CH_3$ |
| Br | — | $OC_2H_5$ | $CH_3$ |
| I | — | $OC_2H_5$ | $CH_3$ |
| $NO_2$ | — | $OC_2H_5$ | $CH_3$ |
| CN | — | $OC_2H_5$ | $CH_3$ |
| $CH_3$ | — | $OC_2H_5$ | $CH_3$ |
| $OCH_3$ | — | $OC_2H_5$ | $CH_3$ |
| $CF_3$ | — | $OC_2H_5$ | $CH_3$ |
| $OCHF_2$ | — | $OC_2H_5$ | $CH_3$ |
| $OCF_3$ | — | $OC_2H_5$ | $CH_3$ |
| $SO_2CH_3$ | — | $OC_2H_5$ | $CH_3$ |
| H | — | $N(CH_3)_2$ | $CH_3$ |
| F | — | $N(CH_3)_2$ | $CH_3$ |
| Cl | — | $N(CH_3)_2$ | $CH_3$ |

-continued

| $R^3$ | (position-) $(R^4)_n$ | $R^5$ | $R^6$ |
|---|---|---|---|
| Br | — | N(CH$_3$)$_2$ | CH$_3$ |
| I | — | N(CH$_3$)$_2$ | CH$_3$ |
| NO$_2$ | — | N(CH$_3$)$_2$ | CH$_3$ |
| CN | — | N(CH$_3$)$_2$ | CH$_3$ |
| CH$_3$ | — | N(CH$_3$)$_2$ | CH$_3$ |
| OCH$_3$ | — | N(CH$_3$)$_2$ | CH$_3$ |
| CF$_3$ | — | N(CH$_3$)$_2$ | CH$_3$ |
| OCHF$_2$ | — | N(CH$_3$)$_2$ | CH$_3$ |
| OCF$_3$ | — | N(CH$_3$)$_2$ | CH$_3$ |
| SO$_2$CH$_3$ | — | N(CH$_3$)$_2$ | CH$_3$ |
| H | — | OCH$_3$ | ▷ |
| F | — | OCH$_3$ | ▷ |
| Cl | — | OCH$_3$ | ▷ |
| Br | — | OCH$_3$ | ▷ |
| I | — | OCH$_3$ | ▷ |
| NO$_2$ | — | OCH$_3$ | ▷ |
| CN | — | OCH$_3$ | ▷ |
| CH$_3$ | — | OCH$_3$ | ▷ |
| OCH$_3$ | — | OCH$_3$ | ▷ |
| CF$_3$ | — | OCH$_3$ | ▷ |
| OCHF$_2$ | — | OCH$_3$ | ▷ |
| OCF$_3$ | — | OCH$_3$ | ▷ |
| SO$_2$CH$_3$ | — | OCH$_3$ | ▷ |
| H | (3-) Cl | CF$_3$ | CH$_3$ |
| F | (3-) Cl | CH$_3$ | CH$_3$ |
| Cl | (3-) Cl | OCH$_3$ | CH$_3$ |
| Br | (3-) Cl | Br | ▷ |
| Cl | (3-) Cl | CF$_3$ | CH$_3$ |
| NO$_2$ | (3-) Cl | CH$_3$ | CH$_3$ |

-continued

| $R^3$ | (position-) $(R^4)_n$ | $R^5$ | $R^6$ |
|---|---|---|---|
| Cl | (3-) Cl | SCH$_3$ | CH$_3$ |
| CH$_3$ | (3-) Cl | Cl | CH$_3$ |
| OCH$_3$ | (3-) Cl | OCH$_3$ | CH$_3$ |
| CF$_3$ | (3-) Cl | CF$_3$ | CH$_3$ |
| OCHF$_2$ | (3-) Cl | CH$_3$ | CH$_3$ |
| OCF$_3$ | (3-) Cl | CH$_3$ | CH$_3$ |
| SO$_2$CH$_3$ | (3-) Cl | OCH$_3$ | CH$_3$ |

Group 2

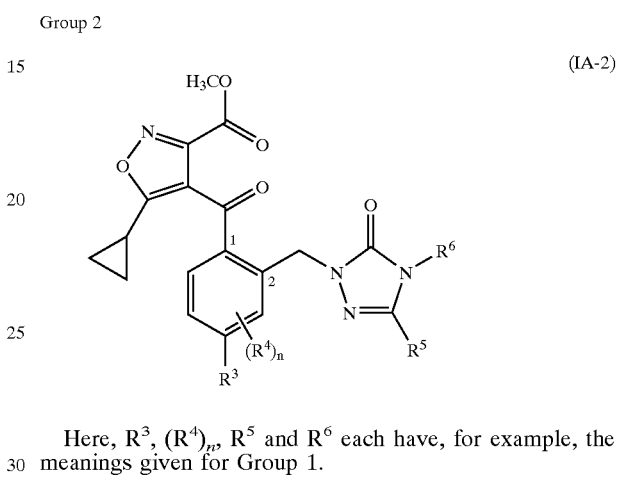

(IA-2)

Here, $R^3$, $(R^4)_n$, $R^5$ and $R^6$ each have, for example, the meanings given for Group 1.

Group 3

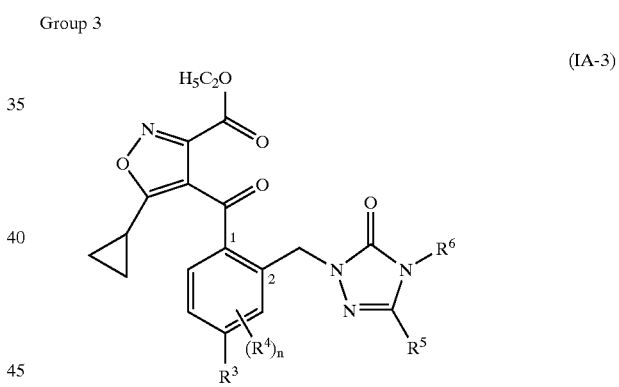

(IA-3)

Here, $R^3$, $(R^4)_n$, $R^5$ and $R^6$ each have, for example, the meanings given for Group 1.

Group 4

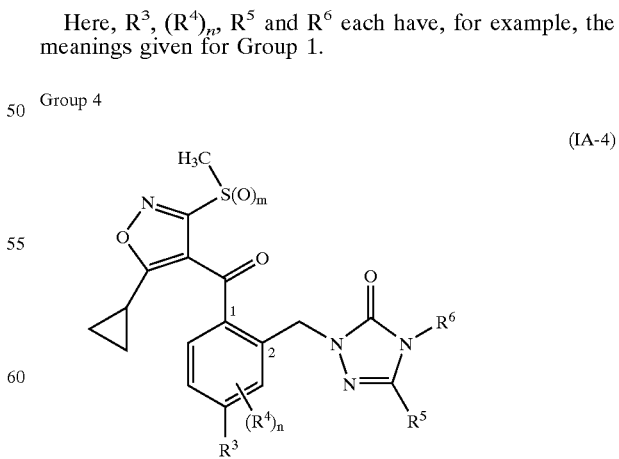

(IA-4)

Here, $R^3$, $(R^4)_n$, $R^5$ and $R^6$ each have, for example, the meanings given for Group 1, and m represents the number 0, 1 or 2.

Group 5

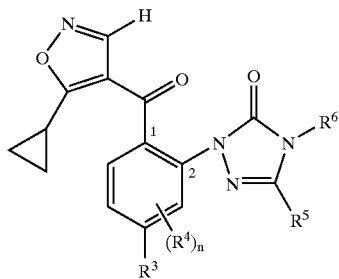
(IA-5)

Here, $R^3$, $(R^4)_n$, $R^5$ and $R^6$ each have, for example, the meanings given for Group 1.

Group 6

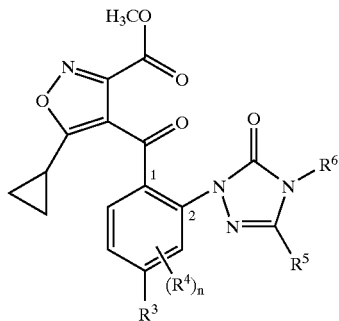
(IA-6)

Here, $R^3$, $(R^4)_n$, $R^5$ and $R^6$ each have, for example, the meanings given for Group 1.

Group 7

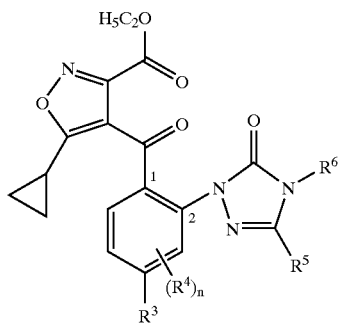
(IA-7)

Here, $R^3$, $(R^4)_n$, $R^5$ and $R^6$ each have, for example, the meanings given for Group 1.

Group 8

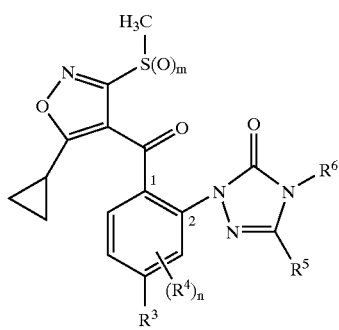
(IA-8)

Here, $R^3$, $(R^4)_n$, $R^5$ and $R^6$ each have, for example, the meanings given for group 1, and m represents the number 0, 1 or 2.

Group 9

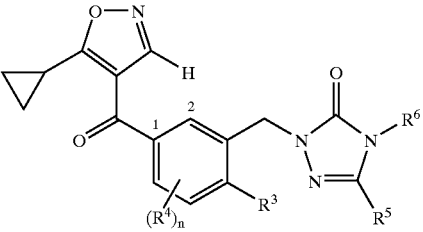
(IB-1)

Here, $R^3$, $(R^4)_n$, $R^5$ and $R^6$ each have, for example, the meanings given in the table below:

| $R^3$ | (position-) $(R^4)_n$ | $R^5$ | $R^6$ |
|---|---|---|---|
| Cl | (2-) Cl | $CF_3$ | $CH_3$ |
| Cl | (2-) Cl | $SCH_3$ | $CH_3$ |
| Cl | (2-) Cl | $SC_2H_5$ | $CH_3$ |
| Cl | (2-) Cl | $SC_3H_7$ | $CH_3$ |
| Cl | (2-) Cl | $SC_3H_7$-i | $CH_3$ |
| Cl | (2-) Cl | 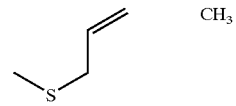 | $CH_3$ |
| Cl | (2-) Cl | 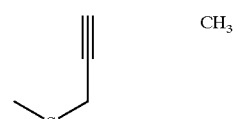 | $CH_3$ |
| Cl | (2-) Cl | 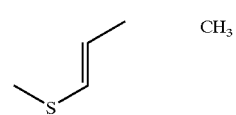 | $CH_3$ |
| Cl | (2-) Cl |  | $CH_3$ |
| Cl | (2-) Cl |  | $CH_3$ |
| Cl | (2-) Cl | $SCH=C=CH_2$ | $CH_3$ |
| Cl | (2-) Cl | $SCH_2CN$ | $CH_3$ |
| Cl | (2-) Cl | $SCH_2CH_2CN$ | $CH_3$ |
| Cl | (2-) Cl | $OCH_3$ | $CH_3$ |
| Cl | (2-) Cl | $OC_2H_5$ | $CH_3$ |
| Cl | (2-) Cl | $OC_3H_7$ | $CH_3$ |
| Cl | (2-) Cl | $OC_3H_7$-i | $CH_3$ |
| Cl | (2-) Cl | $OC_4H_9$ | $CH_3$ |
| Cl | (2-) Cl | $OCH_2CF_3$ | $CH_3$ |
| Cl | (2-) Cl | 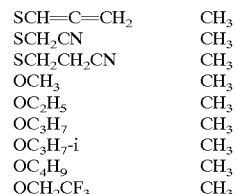 | $CH_3$ |
| | | 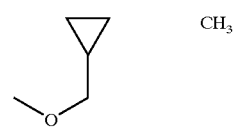 | |

-continued

| $R^3$ | (position-) $(R^4)_n$ | $R^5$ | $R^6$ |
|---|---|---|---|
| Cl | (2-) Cl | $OC_6H_5$ | $CH_3$ |
| Cl | (2-) Cl | H | $CH_3$ |
| Cl | (2-) Cl | $CH_3$ | $CH_3$ |
| Cl | (2-) Cl | $C_2H_5$ | $CH_3$ |
| Cl | (2-) Cl | $C_3H_7$ | $CH_3$ |
| Cl | (2-) Cl | $C_3H_7$-i | $CH_3$ |
| Cl | (2-) Cl | $C_4H_9$ | $CH_3$ |
| Cl | (2-) Cl | $C_4H_9$-i | $CH_3$ |
| Cl | (2-) Cl | $C_4H_9$-s | $CH_3$ |
| Cl | (2-) Cl | $C_4H_9$-t | $CH_3$ |
| Cl | (2-) Cl | cyclopropylmethyl | $CH_3$ |
| Cl | (2-) Cl | cyclopropylethyl | $CH_3$ |
| Cl | (2-) Cl | $CH=CHCH_3$ | $CH_3$ |
| Cl | (2-) Cl | benzyl | $CH_3$ |
| Cl | (2-) Cl | 4-chlorobenzyl | $CH_3$ |
| Cl | (2-) Cl | phenethyl | $CH_3$ |
| Cl | (2-) Cl | $N(CH_3)_2$ | $CH_3$ |
| Cl | (2-) Cl | N-methylmorpholinyl | $CH_3$ |
| Cl | (2-) Cl | Cl | $CH_3$ |
| Cl | (2-) Cl | Br | $CH_3$ |
| $SO_2CH_3$ | (2-) Cl | $CF_3$ | $CH_3$ |
| $SO_2CH_3$ | (2-) Cl | $SCH_3$ | $CH_3$ |
| $SO_2CH_3$ | (2-) Cl | $SC_2H_5$ | $CH_3$ |
| $SO_2CH_3$ | (2-) Cl | $SC_3H_7$ | $CH_3$ |
| $SO_2CH_3$ | (2-) Cl | $SC_3H_7$-i | $CH_3$ |
| $SO_2CH_3$ | (2-) Cl | $SCH_2CH=CH_2$ | $CH_3$ |
| $SO_2CH_3$ | (2-) Cl | $SCH_2C{\equiv}CH$ | $CH_3$ |
| $SO_2CH_3$ | (2-) Cl | $SCH=CHCH_3$ | $CH_3$ |
| $SO_2CH_3$ | (2-) Cl | $SC{\equiv}CCH_3$ | $CH_3$ |
| $SO_2CH_3$ | (2-) Cl | $SCH_2$-cyclopropyl | $CH_3$ |
| $SO_2CH_3$ | (2-) Cl | $SCH=C=CH_2$ | $CH_3$ |
| $SO_2CH_3$ | (2-) Cl | $SCH_2CN$ | $CH_3$ |
| $SO_2CH_3$ | (2-) Cl | $SCH_2CH_2CN$ | $CH_3$ |
| $SO_2CH_3$ | (2-) Cl | $OCH_3$ | $CH_3$ |
| $SO_2CH_3$ | (2-) Cl | $OC_2H_5$ | $CH_3$ |
| $SO_2CH_3$ | (2-) Cl | $OC_3H_7$ | $CH_3$ |
| $SO_2CH_3$ | (2-) Cl | $OC_3H_7$-i | $CH_3$ |
| $SO_2CH_3$ | (2-) Cl | $OC_4H_9$ | $CH_3$ |
| $SO_2CH_3$ | (2-) Cl | $OCH_2CF_3$ | $CH_3$ |
| $SO_2CH_3$ | (2-) Cl | cyclopropylmethoxymethyl | $CH_3$ |
| $SO_2CH_3$ | (2-) Cl | $OC_6H_5$ | $CH_3$ |
| $SO_2CH_3$ | (2-) Cl | H | $CH_3$ |
| $SO_2CH_3$ | (2-) Cl | $CH_3$ | $CH_3$ |
| $SO_2CH_3$ | (2-) Cl | $C_2H_5$ | $CH_3$ |
| $SO_2CH_3$ | (2-) Cl | $C_3H_7$ | $CH_3$ |
| $SO_2CH_3$ | (2-) Cl | $C_3H_7$-i | $CH_3$ |
| $SO_2CH_3$ | (2-) Cl | $C_4H_9$ | $CH_3$ |
| $SO_2CH_3$ | (2-) Cl | $C_4H_9$-i | $CH_3$ |
| $SO_2CH_3$ | (2-) Cl | $C_4H_9$-s | $CH_3$ |
| $SO_2CH_3$ | (2-) Cl | $C_4H_9$-t | $CH_3$ |
| $SO_2CH_3$ | (2-) Cl | cyclopropylmethyl | $CH_3$ |
| $SO_2CH_3$ | (2-) Cl | cyclopropylethyl | $CH_3$ |
| $SO_2CH_3$ | (2-) Cl | $CH=CHCH_3$ | $CH_3$ |
| $SO_2CH_3$ | (2-) Cl | benzyl | $CH_3$ |
| $SO_2CH_3$ | (2-) Cl | 4-chlorobenzyl | $CH_3$ |
| $SO_2CH_3$ | (2-) Cl | phenethyl | $CH_3$ |
| $SO_2CH_3$ | (2-) Cl | $N(CH_3)_2$ | $CH_3$ |
| $SO_2CH_3$ | (2-) Cl | N-methylmorpholinyl | $CH_3$ |
| $SO_2CH_3$ | (2-) Cl | Cl | $CH_3$ |

-continued

| R³ | (position-) (R⁴)ₙ | R⁵ | R⁶ |
|---|---|---|---|
| SO₂CH₃ | (2-) Cl | Br | CH₃ |
| Cl | (2-) SO₂CH₃ | CF₃ | CH₃ |
| Cl | (2-) SO₂CH₃ | SCH₃ | CH₃ |
| Cl | (2-) SO₂CH₃ | SC₂H₅ | CH₃ |
| Cl | (2-) SO₂CH₃ | SC₃H₇ | CH₃ |
| Cl | (2-) SO₂CH₃ | SC₃H₇-i | CH₃ |
| Cl | (2-) SO₂CH₃ | allyl-S- | CH₃ |
| Cl | (2-) SO₂CH₃ | propargyl-S- | CH₃ |
| Cl | (2-) SO₂CH₃ | propenyl-S- | CH₃ |
| Cl | (2-) SO₂CH₃ | propynyl-S- | CH₃ |
| Cl | (2-) SO₂CH₃ | cyclopropylmethyl-S- | CH₃ |
| Cl | (2-) SO₂CH₃ | SCH=C=CH₂ | CH₃ |
| Cl | (2-) SO₂CH₃ | SCH₂CN | CH₃ |
| Cl | (2-) SO₂CH₃ | SCH₂CH₂CN | CH₃ |
| Cl | (2-) SO₂CH₃ | OCH₃ | CH₃ |
| Cl | (2-) SO₂CH₃ | OC₂H₅ | CH₃ |
| Cl | (2-) SO₂CH₃ | OC₃H₇ | CH₃ |
| Cl | (2-) SO₂CH₃ | OC₃H₇-i | CH₃ |
| Cl | (2-) SO₂CH₃ | OC₄H₉ | CH₃ |
| Cl | (2-) SO₂CH₃ | OCH₂CF₃ | CH₃ |
| Cl | (2-) SO₂CH₃ | cyclopropylmethyl-O- | CH₃ |
| Cl | (2-) SO₂CH₃ | OC₆H₅ | CH₃ |
| Cl | (2-) SO₂CH₃ | H | CH₃ |
| Cl | (2-) SO₂CH₃ | CH₃ | CH₃ |
| Cl | (2-) SO₂CH₃ | C₂H₅ | CH₃ |
| Cl | (2-) SO₂CH₃ | C₃H₇ | CH₃ |
| Cl | (2-) SO₂CH₃ | C₃H₇-i | CH₃ |
| Cl | (2-) SO₂CH₃ | C₄H₉ | CH₃ |
| Cl | (2-) SO₂CH₃ | C₄H₉-i | CH₃ |
| Cl | (2-) SO₂CH₃ | C₄H₉-s | CH₃ |
| Cl | (2-) SO₂CH₃ | C₄H₉-t | CH₃ |
| Cl | (2-) SO₂CH₃ | cyclopropyl | CH₃ |
| Cl | (2-) SO₂CH₃ | cyclopropylmethyl | CH₃ |
| Cl | (2-) SO₂CH₃ | CH=CHCH₃ | CH₃ |
| Cl | (2-) SO₂CH₃ | phenyl | CH₃ |
| Cl | (2-) SO₂CH₃ | 4-chlorophenyl | CH₃ |
| Cl | (2-) SO₂CH₃ | benzyl | CH₃ |
| Cl | (2-) SO₂CH₃ | N(CH₃)₂ | CH₃ |
| Cl | (2-) SO₂CH₃ | morpholinyl | CH₃ |
| Cl | (2-) SO₂CH₃ | Cl | CH₃ |
| Cl | (2-) SO₂CH₃ | Br | CH₃ |
| Cl | (2-) Cl | CF₃ | cyclopropyl |
| Cl | (2-) Cl | SCH₃ | cyclopropyl |
| Cl | (2-) Cl | SC₂H₅ | cyclopropyl |
| Cl | (2-) Cl | SC₃H₇ | cyclopropyl |
| Cl | (2-) Cl | SC₃H₇-i | cyclopropyl |
| Cl | (2-) Cl | allyl-S- | cyclopropyl |
| Cl | (2-) Cl | propargyl-S- | cyclopropyl |
| Cl | (2-) Cl | propenyl-S- | cyclopropyl |
| Cl | (2-) Cl | propynyl-S- | cyclopropyl |

-continued

| R³ | (position-) (R⁴)ₙ | R⁵ | R⁶ |
|---|---|---|---|
| Cl | (2-) Cl |  |  |
| Cl | (2-) Cl | SCH=C=CH₂ |  |
| Cl | (2-) Cl | SCH₂CN |  |
| Cl | (2-) Cl | SCH₂CH₂CN |  |
| Cl | (2-) Cl | OCH₃ |  |
| Cl | (2-) Cl | OC₂H₅ |  |
| Cl | (2-) Cl | OC₃H₇ |  |
| Cl | (2-) Cl | OC₃H₇-i |  |
| Cl | (2-) Cl | OC₄H₉ |  |
| Cl | (2-) Cl | OCH₂CF₃ |  |
| Cl | (2-) Cl |  |  |
| Cl | (2-) Cl | OC₆H₅ |  |
| Cl | (2-) Cl | H |  |
| Cl | (2-) Cl | CH₃ |  |
| Cl | (2-) Cl | C₂H₅ |  |
| Cl | (2-) Cl | C₃H₇ |  |
| Cl | (2-) Cl | C₃H₇-i |  |

-continued

| R³ | (position-) (R⁴)ₙ | R⁵ | R⁶ |
|---|---|---|---|
| Cl | (2-) Cl | C₄H₉ |  |
| Cl | (2-) Cl | C₄H₉-i |  |
| Cl | (2-) Cl | C₄H₉-s |  |
| Cl | (2-) Cl | C₄H₉-t |  |
| Cl | (2-) Cl |  |  |
| Cl | (2-) Cl |  | |
| Cl | (2-) Cl | CH=CHCH₃ | |
| Cl | (2-) Cl | | |
| Cl | (2-) Cl | | |
| Cl | (2-) Cl | | |
| Cl | (2-) Cl | N(CH₃)₂ | |
| Cl | (2-) Cl | | |
| Cl | (2-) Cl | Cl | |
| Cl | (2-) Cl | Br | |
| SO₂CH₃ | (2-) Cl | CF₃ | |
| SO₂CH₃ | (2-) Cl | SCH₃ | |
| SO₂CH₃ | (2-) Cl | SC₂H₅ | |

-continued

| R³ | (position-) (R⁴)ₙ | R⁵ | R⁶ |
|---|---|---|---|
| SO₂CH₃ | (2-) Cl | SC₃H₇ | cyclopropyl |
| SO₂CH₃ | (2-) Cl | SC₃H₇-i | cyclopropyl |
| SO₂CH₃ | (2-) Cl | SCH₂CH=CH₂ | cyclopropyl |
| SO₂CH₃ | (2-) Cl | SCH₂C≡CH | cyclopropyl |
| SO₂CH₃ | (2-) Cl | SCH₂CH=CHCH₃ | cyclopropyl |
| SO₂CH₃ | (2-) Cl | SC≡CCH₃ | cyclopropyl |
| SO₂CH₃ | (2-) Cl | SCH₂-cyclopropyl | cyclopropyl |
| SO₂CH₃ | (2-) Cl | SCH=C=CH₂ | cyclopropyl |
| SO₂CH₃ | (2-) Cl | SCH₂CN | cyclopropyl |
| SO₂CH₃ | (2-) Cl | SCH₂CH₂CN | cyclopropyl |
| SO₂CH₃ | (2-) Cl | OCH₃ | cyclopropyl |
| SO₂CH₃ | (2-) Cl | OC₂H₅ | cyclopropyl |
| SO₂CH₃ | (2-) Cl | OC₃H₇ | cyclopropyl |
| SO₂CH₃ | (2-) Cl | OC₃H₇-i | cyclopropyl |
| SO₂CH₃ | (2-) Cl | OC₄H₉ | cyclopropyl |
| SO₂CH₃ | (2-) Cl | OCH₂CF₃ | cyclopropyl |
| SO₂CH₃ | (2-) Cl | OCH₂-cyclopropyl | cyclopropyl |
| SO₂CH₃ | (2-) Cl | OC₆H₅ | cyclopropyl |
| SO₂CH₃ | (2-) Cl | H | cyclopropyl |
| SO₂CH₃ | (2-) Cl | CH₃ | cyclopropyl |
| SO₂CH₃ | (2-) Cl | C₂H₅ | cyclopropyl |
| SO₂CH₃ | (2-) Cl | C₃H₇ | cyclopropyl |
| SO₂CH₃ | (2-) Cl | C₃H₇-i | cyclopropyl |
| SO₂CH₃ | (2-) Cl | C₄H₉ | cyclopropyl |
| SO₂CH₃ | (2-) Cl | C₄H₉-i | cyclopropyl |
| SO₂CH₃ | (2-) Cl | C₄H₉-s | cyclopropyl |
| SO₂CH₃ | (2-) Cl | C₄H₉-t | cyclopropyl |
| SO₂CH₃ | (2-) Cl | cyclopropyl | cyclopropyl |
| SO₂CH₃ | (2-) Cl | CH₂-cyclopropyl | cyclopropyl |
| SO₂CH₃ | (2-) Cl | CH=CHCH₃ | cyclopropyl |
| SO₂CH₃ | (2-) Cl | CH₂-C₆H₅ | cyclopropyl |
| SO₂CH₃ | (2-) Cl | CH₂-C₆H₄-4-Cl | cyclopropyl |
| SO₂CH₃ | (2-) Cl | CH₂CH₂-C₆H₅ | cyclopropyl |

-continued

| $R^3$ | (position-) $(R^4)_n$ | $R^5$ | $R^6$ |
|---|---|---|---|
| $SO_2CH_3$ | (2-) Cl | $N(CH_3)_2$ | cyclopropyl |
| $SO_2CH_3$ | (2-) Cl | N-methylmorpholine | cyclopropyl |
| $SO_2CH_3$ | (2-) Cl | Cl | cyclopropyl |
| $SO_2CH_3$ | (2-) Cl | Br | cyclopropyl |
| Cl | (2-) $SO_2CH_3$ | $CF_3$ | cyclopropyl |
| Cl | (2-) $SO_2CH_3$ | $SCH_3$ | cyclopropyl |
| Cl | (2-) $SO_2CH_3$ | $SC_2H_5$ | cyclopropyl |
| Cl | (2-) $SO_2CH_3$ | $SC_3H_7$ | cyclopropyl |
| Cl | (2-) $SO_2CH_3$ | $SC_3H_7$-i | cyclopropyl |
| Cl | (2-) $SO_2CH_3$ | $SCH_2CH=CH_2$ | cyclopropyl |
| Cl | (2-) $SO_2CH_3$ | $SCH_2C{\equiv}CCH_3$ | cyclopropyl |
| Cl | (2-) $SO_2CH_3$ | $SCH=CHCH_3$ | cyclopropyl |
| Cl | (2-) $SO_2CH_3$ | $SC{\equiv}CH$ | cyclopropyl |
| Cl | (2-) $SO_2CH_3$ | $SCH_2$-cyclopropyl | cyclopropyl |
| Cl | (2-) $SO_2CH_3$ | $SCH=C=CH_2$ | cyclopropyl |
| Cl | (2-) $SO_2CH_3$ | $SCH_2CN$ | cyclopropyl |
| Cl | (2-) $SO_2CH_3$ | $SCH_2CH_2CN$ | cyclopropyl |
| Cl | (2-) $SO_2CH_3$ | $OCH_3$ | cyclopropyl |
| Cl | (2-) $SO_2CH_3$ | $OC_2H_5$ | cyclopropyl |
| Cl | (2-) $SO_2CH_3$ | $OC_3H_7$ | cyclopropyl |
| Cl | (2-) $SO_2CH_3$ | $OC_3H_7$-i | cyclopropyl |
| Cl | (2-) $SO_2CH_3$ | $OC_4H_9$ | cyclopropyl |
| Cl | (2-) $SO_2CH_3$ | $OCH_2CF_3$ | cyclopropyl |
| Cl | (2-) $SO_2CH_3$ | $OCH_2$-cyclopropyl | cyclopropyl |
| Cl | (2-) $SO_2CH_3$ | $OC_6H_5$ | cyclopropyl |
| Cl | (2-) $SO_2CH_3$ | H | cyclopropyl |
| Cl | (2-) $SO_2CH_3$ | $CH_3$ | cyclopropyl |
| Cl | (2-) $SO_2CH_3$ | $C_2H_5$ | cyclopropyl |
| Cl | (2-) $SO_2CH_3$ | $C_3H_7$ | cyclopropyl |
| Cl | (2-) $SO_2CH_3$ | $C_3H_7$-i | cyclopropyl |
| Cl | (2-) $SO_2CH_3$ | $C_4H_9$ | cyclopropyl |
| Cl | (2-) $SO_2CH_3$ | $C_4H_9$-i | cyclopropyl |
| Cl | (2-) $SO_2CH_3$ | $C_4H_9$-s | cyclopropyl |

-continued

| R³ | (position-) (R⁴)ₙ | R⁵ | R⁶ |
|---|---|---|---|
| Cl | (2-) SO₂CH₃ | C₄H₉-t |  |
| Cl | (2-) SO₂CH₃ |  |  |
| Cl | (2-) SO₂CH₃ |  |  |
| Cl | (2-) SO₂CH₃ | CH=CHCH₃ |  |
| Cl | (2-) SO₂CH₃ |  |  |
| Cl | (2-) SO₂CH₃ |  |  |
| Cl | (2-) SO₂CH₃ |  |  |
| Cl | (2-) SO₂CH₃ | N(CH₃)₂ |  |
| Cl | (2-) SO₂CH₃ |  |  |
| Cl | (2-) SO₂CH₃ | Cl |  |
| Cl | (2-) SO₂CH₃ | Br |  |
| Cl | (2-) Cl | CF₃ | N(CH₃)₂ |
| Cl | (2-) Cl | SCH₃ | N(CH₃)₂ |
| Cl | (2-) Cl | SC₂H₅ | N(CH₃)₂ |
| Cl | (2-) Cl | SC₃H₇ | N(CH₃)₂ |
| Cl | (2-) Cl | SC₃H₇-i | N(CH₃)₂ |
| Cl | (2-) Cl |  | N(CH₃)₂ |
| Cl | (2-) Cl |  | N(CH₃)₂ |
| Cl | (2-) Cl |  | N(CH₃)₂ |

-continued

| R³ | (position-) (R⁴)ₙ | R⁵ | R⁶ |
|---|---|---|---|
| Cl | (2-) Cl |  | N(CH₃)₂ |
| Cl | (2-) Cl |  | N(CH₃)₂ |
| Cl | (2-) Cl | SCH=C=CH₂ | N(CH₃)₂ |
| Cl | (2-) Cl | SCH₂CN | N(CH₃)₂ |
| Cl | (2-) Cl | SCH₂CH₂CN | N(CH₃)₂ |
| Cl | (2-) Cl | OCH₃ | N(CH₃)₂ |
| Cl | (2-) Cl | OC₂H₅ | N(CH₃)₂ |
| Cl | (2-) Cl | OC₃H₇ | N(CH₃)₂ |
| Cl | (2-) Cl | OC₃H₇-i | N(CH₃)₂ |
| Cl | (2-) Cl | OC₄H₉ | N(CH₃)₂ |
| Cl | (2-) Cl | OCH₂CF₃ | N(CH₃)₂ |
| Cl | (2-) Cl |  | N(CH₃)₂ |
| Cl | (2-) Cl | OC₆H₅ | N(CH₃)₂ |
| Cl | (2-) Cl | H | N(CH₃)₂ |
| Cl | (2-) Cl | CH₃ | N(CH₃)₂ |
| Cl | (2-) Cl | C₂H₅ | N(CH₃)₂ |
| Cl | (2-) Cl | C₃H₇ | N(CH₃)₂ |
| Cl | (2-) Cl | C₃H₇-i | N(CH₃)₂ |
| Cl | (2-) Cl | C₄H₉ | N(CH₃)₂ |
| Cl | (2-) Cl | C₄H₉-i | N(CH₃)₂ |
| Cl | (2-) Cl | C₄H₉-s | N(CH₃)₂ |
| Cl | (2-) Cl | C₄H₉-t | N(CH₃)₂ |
| Cl | (2-) Cl |  | N(CH₃)₂ |
| Cl | (2-) Cl |  | N(CH₃)₂ |
| Cl | (2-) Cl | CH=CHCH₃ | N(CH₃)₂ |
| Cl | (2-) Cl |  | N(CH₃)₂ |
| Cl | (2-) Cl |  | N(CH₃)₂ |
| Cl | (2-) Cl |  | N(CH₃)₂ |
| Cl | (2-) Cl | N(CH₃)₂ | N(CH₃)₂ |
| Cl | (2-) Cl |  | N(CH₃)₂ |
| Cl | (2-) Cl | Cl | N(CH₃)₂ |

-continued

| R³ | (position-) (R⁴)ₙ | R⁵ | R⁶ |
|---|---|---|---|
| Cl | (2-) Cl | Br | N(CH₃)₂ |
| SO₂CH₃ | (2-) Cl | CF₃ | N(CH₃)₂ |
| SO₂CH₃ | (2-) Cl | SCH₃ | N(CH₃)₂ |
| SO₂CH₃ | (2-) Cl | SC₂H₅ | N(CH₃)₂ |
| SO₂CH₃ | (2-) Cl | SC₃H₇ | N(CH₃)₂ |
| SO₂CH₃ | (2-) Cl | SC₃H₇-i | N(CH₃)₂ |
| SO₂CH₃ | (2-) Cl | 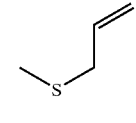 | N(CH₃)₂ |
| SO₂CH₃ | (2-) Cl | 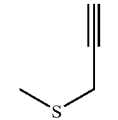 | N(CH₃)₂ |
| SO₂CH₃ | (2-) Cl | 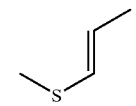 | N(CH₃)₂ |
| SO₂CH₃ | (2-) Cl | 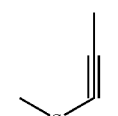 | N(CH₃)₂ |
| SO₂CH₃ | (2-) Cl | 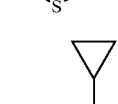 | N(CH₃)₂ |
| SO₂CH₃ | (2-) Cl | SCH=C=CH₂ | N(CH₃)₂ |
| SO₂CH₃ | (2-) Cl | SCH₂CN | N(CH₃)₂ |
| SO₂CH₃ | (2-) Cl | SCH₂CH₂CN | N(CH₃)₂ |
| SO₂CH₃ | (2-) Cl | OCH₃ | N(CH₃)₂ |
| SO₂CH₃ | (2-) Cl | OC₂H₅ | N(CH₃)₂ |
| SO₂CH₃ | (2-) Cl | OC₃H₇ | N(CH₃)₂ |
| SO₂CH₃ | (2-) Cl | OC₃H₇-i | N(CH₃)₂ |
| SO₂CH₃ | (2-) Cl | OC₄H₉ | N(CH₃)₂ |
| SO₂CH₃ | (2-) Cl | OCH₂CF₃ | N(CH₃)₂ |
| SO₂CH₃ | (2-) Cl | 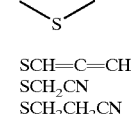 | N(CH₃)₂ |
| SO₂CH₃ | (2-) Cl | OC₆H₅ | N(CH₃)₂ |
| SO₂CH₃ | (2-) Cl | H | N(CH₃)₂ |
| SO₂CH₃ | (2-) Cl | CH₃ | N(CH₃)₂ |
| SO₂CH₃ | (2-) Cl | C₂H₅ | N(CH₃)₂ |
| SO₂CH₃ | (2-) Cl | C₃H₇ | N(CH₃)₂ |
| SO₂CH₃ | (2-) Cl | C₃H₇-i | N(CH₃)₂ |
| SO₂CH₃ | (2-) Cl | C₄H₉ | N(CH₃)₂ |
| SO₂CH₃ | (2-) Cl | C₄H₉-i | N(CH₃)₂ |
| SO₂CH₃ | (2-) Cl | C₄H₉-s | N(CH₃)₂ |
| SO₂CH₃ | (2-) Cl | C₄H₉-t | N(CH₃)₂ |
| SO₂CH₃ | (2-) Cl | 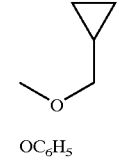 | N(CH₃)₂ |
| SO₂CH₃ | (2-) Cl |  | N(CH₃)₂ |
| SO₂CH₃ | (2-) Cl | CH=CHCH₃ | N(CH₃)₂ |

-continued

| R³ | (position-) (R⁴)ₙ | R⁵ | R⁶ |
|---|---|---|---|
| SO₂CH₃ | (2-) Cl | 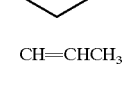 | N(CH₃)₂ |
| SO₂CH₃ | (2-) Cl | 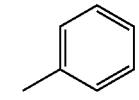 | N(CH₃)₂ |
| SO₂CH₃ | (2-) Cl | 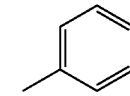 | N(CH₃)₂ |
| SO₂CH₃ | (2-) Cl | N(CH₃)₂ | N(CH₃)₂ |
| SO₂CH₃ | (2-) Cl | 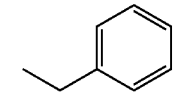 | N(CH₃)₂ |
| SO₂CH₃ | (2-) Cl | Cl | N(CH₃)₂ |
| SO₂CH₃ | (2-) Cl | Br | N(CH₃)₂ |
| Cl | (2-) SO₂CH₃ | CF₃ | N(CH₃)₂ |
| Cl | (2-) SO₂CH₃ | SCH₃ | N(CH₃)₂ |
| Cl | (2-) SO₂CH₃ | SC₂H₅ | N(CH₃)₂ |
| Cl | (2-) SO₂CH₃ | SC₃H₇ | N(CH₃)₂ |
| Cl | (2-) SO₂CH₃ | SC₃H₇-i | N(CH₃)₂ |
| Cl | (2-) SO₂CH₃ | 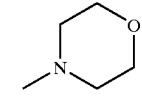 | N(CH₃)₂ |
| Cl | (2-) SO₂CH₃ | 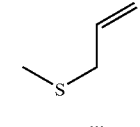 | N(CH₃)₂ |
| Cl | (2-) SO₂CH₃ | 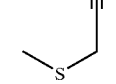 | N(CH₃)₂ |
| Cl | (2-) SO₂CH₃ | 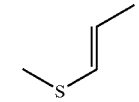 | N(CH₃)₂ |
| Cl | (2-) SO₂CH₃ |  | N(CH₃)₂ |
| Cl | (2-) SO₂CH₃ | SCH=C=CH₂ | N(CH₃)₂ |
| Cl | (2-) SO₂CH₃ | SCH₂CN | N(CH₃)₂ |
| Cl | (2-) SO₂CH₃ | SCH₂CH₂CN | N(CH₃)₂ |
| Cl | (2-) SO₂CH₃ | OCH₃ | N(CH₃)₂ |
| Cl | (2-) SO₂CH₃ | OC₂H₅ | N(CH₃)₂ |
| Cl | (2-) SO₂CH₃ | OC₃H₇ | N(CH₃)₂ |
| Cl | (2-) SO₂CH₃ | OC₃H₇-i | N(CH₃)₂ |
| Cl | (2-) SO₂CH₃ | OC₄H₉ | N(CH₃)₂ |
| Cl | (2-) SO₂CH₃ | OCH₂CF₃ | N(CH₃)₂ |

-continued

| R³ | (position-) (R⁴)ₙ | R⁵ | R⁶ |
|---|---|---|---|
| Cl | (2-) SO₂CH₃ | 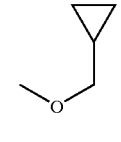 | N(CH₃)₂ |
| Cl | (2-) SO₂CH₃ | OC₆H₅ | N(CH₃)₂ |
| Cl | (2-) SO₂CH₃ | H | N(CH₃)₂ |
| Cl | (2-) SO₂CH₃ | CH₃ | N(CH₃)₂ |
| Cl | (2-) SO₂CH₃ | C₂H₅ | N(CH₃)₂ |
| Cl | (2-) SO₂CH₃ | C₃H₇ | N(CH₃)₂ |
| Cl | (2-) SO₂CH₃ | C₃H₇-i | N(CH₃)₂ |
| Cl | (2-) SO₂CH₃ | C₄H₉ | N(CH₃)₂ |
| Cl | (2-) SO₂CH₃ | C₄H₉-i | N(CH₃)₂ |
| Cl | (2-) SO₂CH₃ | C₄H₉-s | N(CH₃)₂ |
| Cl | (2-) SO₂CH₃ | C₄H₉-t | N(CH₃)₂ |
| Cl | (2-) SO₂CH₃ |  | N(CH₃)₂ |
| Cl | (2-) SO₂CH₃ |  | N(CH₃)₂ |
| Cl | (2-) SO₂CH₃ | CH=CHCH₃ | N(CH₃)₂ |
| Cl | (2-) SO₂CH₃ |  | N(CH₃)₂ |
| Cl | (2-) SO₂CH₃ | 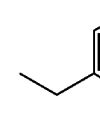 | N(CH₃)₂ |
| Cl | (2-) SO₂CH₃ |  | N(CH₃)₂ |
| Cl | (2-) SO₂CH₃ | N(CH₃)₂ | N(CH₃)₂ |
| Cl | (2-) SO₂CH₃ |  | N(CH₃)₂ |
| Cl | (2-) SO₂CH₃ | Cl | N(CH₃)₂ |
| Cl | (2-) SO₂CH₃ | Br | N(CH₃)₂ |
| Cl | (2-) Cl | CH₃ | OCH₃ |
| Cl | (2-) Cl | C₂H₅ | OCH₃ |
| Cl | (2-) Cl | C₃H₇ | OCH₃ |
| Cl | (2-) Cl | SCH₃ | OCH₃ |
| Cl | (2-) Cl | SC₂H₅ | OCH₃ |
| Cl | (2-) Cl | OCH₃ | OCH₃ |
| Cl | (2-) Cl | OC₂H₅ | OCH₃ |
| Cl | (2-) Cl | CH₃ | OC₂H₅ |
| Cl | (2-) Cl | C₂H₅ | OC₂H₅ |
| Cl | (2-) Cl | C₃H₇ | OC₂H₅ |
| Cl | (2-) Cl | SCH₃ | OC₂H₅ |
| Cl | (2-) Cl | SC₂H₅ | OC₂H₅ |
| Cl | (2-) Cl | OCH₃ | OC₂H₅ |
| Cl | (2-) Cl | OC₂H₅ | OC₂H₅ |
| Cl | (2-) SO₂CH₃ | CH₃ | OCH₃ |
| Cl | (2-) SO₂CH₃ | C₂H₅ | OCH₃ |
| Cl | (2-) SO₂CH₃ | C₃H₇ | OCH₃ |
| Cl | (2-) SO₂CH₃ | SCH₃ | OCH₃ |
| Cl | (2-) SO₂CH₃ | SC₂H₅ | OCH₃ |
| Cl | (2-) SO₂CH₃ | OCH₃ | OCH₃ |
| Cl | (2-) SO₂CH₃ | OC₂H₅ | OCH₃ |
| Cl | (2-) SO₂CH₃ | CH₃ | OC₂H₅ |

-continued

| R³ | (position-) (R⁴)ₙ | R⁵ | R⁶ |
|---|---|---|---|
| Cl | (2-) SO₂CH₃ | C₂H₅ | OC₂H₅ |
| Cl | (2-) SO₂CH₃ | C₃H₇ | OC₂H₅ |
| Cl | (2-) SO₂CH₃ | SCH₃ | OC₂H₅ |
| Cl | (2-) SO₂CH₃ | SC₂H₅ | OC₂H₅ |
| Cl | (2-) SO₂CH₃ | OCH₃ | OC₂H₅ |
| Cl | (2-) SO₂CH₃ | OC₂H₅ | OC₂H₅ |
| SO₂CH₃ | (2-) Cl | Cl | OCH₃ |
| SO₂CH₃ | (2-) Cl | Br | OCH₃ |
| SO₂CH₃ | (2-) Cl | CH₃ | OCH₃ |
| SO₂CH₃ | (2-) Cl | C₂H₅ | OCH₃ |
| SO₂CH₃ | (2-) Cl | C₃H₇ | OCH₃ |
| SO₂CH₃ | (2-) Cl | SCH₃ | OCH₃ |
| SO₂CH₃ | (2-) Cl | SC₂H₅ | OCH₃ |
| SO₂CH₃ | (2-) Cl | OCH₃ | OC₂H₅ |
| SO₂CH₃ | (2-) Cl | OC₂H₅ | OC₂H₅ |
| SO₂CH₃ | (2-) Cl | CH₃ | OC₂H₅ |
| SO₂CH₃ | (2-) Cl | C₂H₅ | OC₂H₅ |
| SO₂CH₃ | (2-) Cl | C₃H₇ | OC₂H₅ |
| SO₂CH₃ | (2-) Cl | SCH₃ | OC₂H₅ |
| SO₂CH₃ | (2-) Cl | SC₂H₅ | OC₂H₅ |
| SO₂CH₃ | (2-) Cl | OCH₃ | OC₂H₅ |
| CF₃ | (2-) Cl | Br | CH₃ |
| CF₃ | (2-) Cl | SCH₃ | CH₃ |
| CF₃ | (2-) Cl | OCH₃ | CH₃ |
| CF₃ | (2-) Cl | N(CH₃)₂ | CH₃ |
| CF₃ | (2-) Cl | CF₃ | CH₃ |
| CF₃ | (2-) NO₂ | Br | CH₃ |
| CF₃ | (2-) NO₂ | SCH₃ | CH₃ |
| CF₃ | (2-) NO₂ | OCH₃ | CH₃ |
| CF₃ | (2-) NO₂ | N(CH₃)₂ | CH₃ |
| CF₃ | (2-) NO₂ | CF₃ | CH₃ |
| CF₃ | (2-) CH₃ | Br | CH₃ |
| CF₃ | (2-) CH₃ | SCH₃ | CH₃ |
| CF₃ | (2-) CH₃ | OCH₃ | CH₃ |
| CF₃ | (2-) CH₃ | N(CH₃)₂ | CH₃ |
| CF₃ | (2-) CH₃ | CF₃ | CH₃ |
| CF₃ | (2-) OCH₃ | Br | CH₃ |
| CF₃ | (2-) OCH₃ | SCH₃ | CH₃ |
| CF₃ | (2-) OCH₃ | OCH₃ | CH₃ |
| CF₃ | (2-) OCH₃ | N(CH₃)₂ | CH₃ |
| CF₃ | (2-) OCH₃ | CF₃ | CH₃ |
| SO₂CH₃ | (2-) NO₂ | Br | CH₃ |
| SO₂CH₃ | (2-) NO₂ | SCH₃ | CH₃ |
| SO₂CH₃ | (2-) NO₂ | OCH₃ | CH₃ |
| SO₂CH₃ | (2-) NO₂ | N(CH₃)₂ | CH₃ |
| SO₂CH₃ | (2-) NO₂ | CF₃ | CH₃ |
| SO₂CH₃ | (2-) CF₃ | Br | CH₃ |
| SO₂CH₃ | (2-) CF₃ | SCH₃ | CH₃ |
| SO₂CH₃ | (2-) CF₃ | OCH₃ | CH₃ |
| SO₂CH₃ | (2-) CF₃ | N(CH₃)₂ | CH₃ |
| SO₂CH₃ | (2-) CF₃ | CF₃ | CH₃ |
| SO₂CH₃ | (2-) SO₂CH₃ | Br | CH₃ |
| SO₂CH₃ | (2-) SO₂CH₃ | SCH₃ | CH₃ |
| SO₂CH₃ | (2-) SO₂CH₃ | OCH₃ | CH₃ |
| SO₂CH₃ | (2-) SO₂CH₃ | N(CH₃)₂ | CH₃ |
| SO₂CH₃ | (2-) SO₂CH₃ | CF₃ | CH₃ |
| CN | (2-) Cl | Br | CH₃ |
| CN | (2-) Cl | SCH₃ | CH₃ |
| CN | (2-) Cl | OCH₃ | CH₃ |
| CN | (2-) Cl | N(CH₃)₂ | CH₃ |
| CN | (2-) Cl | CF₃ | CH₃ |
| CN | (2-) NO₂ | Br | CH₃ |
| CN | (2-) NO₂ | SCH₃ | CH₃ |
| CN | (2-) NO₂ | OCH₃ | CH₃ |
| CN | (2-) NO₂ | N(CH₃)₂ | CH₃ |
| CN | (2-) NO₂ | CF₃ | CH₃ |
| CN | (2-) CF₃ | Br | CH₃ |
| CN | (2-) CF₃ | SCH₃ | CH₃ |
| CN | (2-) CF₃ | OCH₃ | CH₃ |
| CN | (2-) CF₃ | N(CH₃)₂ | CH₃ |
| CN | (2-) CF₃ | CF₃ | CH₃ |
| CN | (2-) SO₂CH₃ | Br | CH₃ |
| CN | (2-) SO₂CH₃ | SCH₃ | CH₃ |
| CN | (2-) SO₂CH₃ | OCH₃ | CH₃ |
| CN | (2-) SO₂CH₃ | N(CH₃)₂ | CH₃ |
| CN | (2-) SO₂CH₃ | CF₃ | CH₃ |
| Br | (2-) NO₂ | Br | CH₃ |

| $R^3$ | (position-) $(R^4)_n$ | $R^5$ | $R^6$ |
|---|---|---|---|
| Br | (2-) $NO_2$ | $SCH_3$ | $CH_3$ |
| Br | (2-) $NO_2$ | $OCH_3$ | $CH_3$ |
| Br | (2-) $NO_2$ | $N(CH_3)_2$ | $CH_3$ |
| Br | (2-) $NO_2$ | $CF_3$ | $CH_3$ |
| Br | (2-) $CF_3$ | Br | $CH_3$ |
| Br | (2-) $CF_3$ | $SCH_3$ | $CH_3$ |
| Br | (2-) $CF_3$ | $OCH_3$ | $CH_3$ |
| Br | (2-) $CF_3$ | $N(CH_3)_2$ | $CH_3$ |
| Br | (2-) $CF_3$ | $CF_3$ | $CH_3$ |
| Br | (2-) $SO_2CH_3$ | Br | $CH_3$ |
| Br | (2-) $SO_2CH_3$ | $SCH_3$ | $CH_3$ |
| Br | (2-) $SO_2CH_3$ | $OCH_3$ | $CH_3$ |
| Br | (2-) $SO_2CH_3$ | $N(CH_3)_2$ | $CH_3$ |
| Br | (2-) $SO_2CH_3$ | $CF_3$ | $CH_3$ |
| Br | (2-) $CH_3$ | Br | $CH_3$ |
| Br | (2-) $CH_3$ | $SCH_3$ | $CH_3$ |
| Br | (2-) $CH_3$ | $OCH_3$ | $CH_3$ |
| Br | (2-) $CH_3$ | $N(CH_3)_2$ | $CH_3$ |
| Br | (2-) $CH_3$ | $CF_3$ | $CH_3$ |
| Cl | (2-) $OCH_3$ | $CF_3$ | $CH_3$ |
| Cl | (2-) $OCH_3$ | $SCH_3$ | $CH_3$ |
| Cl | (2-) $OCH_3$ | $SC_2H_5$ | $CH_3$ |
| Cl | (2-) $OCH_3$ | $SC_3H_7$ | $CH_3$ |
| Cl | (2-) $OCH_3$ | $SC_3H_7$-i | $CH_3$ |
| Cl | (2-) $OCH_3$ | $SCH_2CH=CH_2$ (allyl-S-) | $CH_3$ |
| Cl | (2-) $OCH_3$ | $SCH_2C{\equiv}CH$ (propargyl-S-) | $CH_3$ |
| Cl | (2-) $OCH_3$ | $SCH=CHCH_3$ | $CH_3$ |
| Cl | (2-) $OCH_3$ | $SC{\equiv}CCH_3$ | $CH_3$ |
| Cl | (2-) $OCH_3$ | $SCH_2$-cyclopropyl | $CH_3$ |
| Cl | (2-) $OCH_3$ | $SCH=C=CH_2$ | $CH_3$ |
| Cl | (2-) $OCH_3$ | $SCH_2CN$ | $CH_3$ |
| Cl | (2-) $OCH_3$ | $SCH_2CH_2CN$ | $CH_3$ |
| Cl | (2-) $OCH_3$ | $OCH_3$ | $CH_3$ |
| Cl | (2-) $OCH_3$ | $OC_2H_5$ | $CH_3$ |
| Cl | (2-) $OCH_3$ | $OC_3H_7$ | $CH_3$ |
| Cl | (2-) $OCH_3$ | $OC_3H_7$-i | $CH_3$ |
| Cl | (2-) $OCH_3$ | $OC_4H_9$ | $CH_3$ |
| Cl | (2-) $OCH_3$ | $OCH_2CF_3$ | $CH_3$ |
| Cl | (2-) $OCH_3$ | $OCH_2$-cyclopropyl | $CH_3$ |
| Cl | (2-) $OCH_3$ | $OC_6H_5$ | $CH_3$ |
| Cl | (2-) $OCH_3$ | H | $CH_3$ |
| Cl | (2-) $OCH_3$ | $CH_3$ | $CH_3$ |
| Cl | (2-) $OCH_3$ | $C_2H_5$ | $CH_3$ |
| Cl | (2-) $OCH_3$ | $C_3H_7$ | $CH_3$ |
| Cl | (2-) $OCH_3$ | $C_3H_7$-i | $CH_3$ |
| Cl | (2-) $OCH_3$ | $C_4H_9$ | $CH_3$ |
| Cl | (2-) $OCH_3$ | $C_4H_9$-i | $CH_3$ |
| Cl | (2-) $OCH_3$ | $C_4H_9$-s | $CH_3$ |
| Cl | (2-) $OCH_3$ | $C_4H_9$-t | $CH_3$ |
| Cl | (2-) $OCH_3$ | cyclopropyl | $CH_3$ |
| Cl | (2-) $OCH_3$ | $CH_2$-cyclopropyl | $CH_3$ |
| Cl | (2-) $OCH_3$ | $CH=CHCH_3$ | $CH_3$ |
| Cl | (2-) $OCH_3$ | phenyl | $CH_3$ |
| Cl | (2-) $OCH_3$ | 4-Cl-phenyl | $CH_3$ |
| Cl | (2-) $OCH_3$ | $CH_2$-phenyl | $CH_3$ |
| Cl | (2-) $OCH_3$ | $N(CH_3)_2$ | $CH_3$ |
| Cl | (2-) $OCH_3$ | morpholino | $CH_3$ |
| Cl | (2-) $OCH_3$ | Cl | $CH_3$ |
| Cl | (2-) $OCH_3$ | Br | $CH_3$ |
| $SO_2CH_3$ | (2-) $OCH_3$ | $CF_3$ | $CH_3$ |
| $SO_2CH_3$ | (2-) $OCH_3$ | $SCH_3$ | $CH_3$ |
| $SO_2CH_3$ | (2-) $OCH_3$ | $SC_2H_5$ | $CH_3$ |
| $SO_2CH_3$ | (2-) $OCH_3$ | $SC_3H_7$ | $CH_3$ |
| $SO_2CH_3$ | (2-) $OCH_3$ | $SC_3H_7$-i | $CH_3$ |
| $SO_2CH_3$ | (2-) $OCH_3$ | $SCH_2CH=CH_2$ (allyl-S-) | $CH_3$ |
| $SO_2CH_3$ | (2-) $OCH_3$ | $SCH_2C{\equiv}CH$ (propargyl-S-) | $CH_3$ |
| $SO_2CH_3$ | (2-) $OCH_3$ | $SCH=CHCH_3$ | $CH_3$ |
| $SO_2CH_3$ | (2-) $OCH_3$ | $SC{\equiv}CCH_3$ | $CH_3$ |

-continued

| R³ | (position-) (R⁴)ₙ | R⁵ | R⁶ |
|---|---|---|---|
| SO₂CH₃ | (2-) OCH₃ |  | CH₃ |
| SO₂CH₃ | (2-) OCH₃ | SCH=C=CH₂ | CH₃ |
| SO₂CH₃ | (2-) OCH₃ | SCH₂CN | CH₃ |
| SO₂CH₃ | (2-) OCH₃ | SCH₂CH₂CN | CH₃ |
| SO₂CH₃ | (2-) OCH₃ | OCH₃ | CH₃ |
| SO₂CH₃ | (2-) OCH₃ | OC₂H₅ | CH₃ |
| SO₂CH₃ | (2-) OCH₃ | OC₃H₇ | CH₃ |
| SO₂CH₃ | (2-) OCH₃ | OC₃H₇-i | CH₃ |
| SO₂CH₃ | (2-) OCH₃ | OC₄H₉ | CH₃ |
| SO₂CH₃ | (2-) OCH₃ | OCH₂CF₃ | CH₃ |
| SO₂CH₃ | (2-) OCH₃ |  | CH₃ |
| SO₂CH₃ | (2-) OCH₃ | OC₆H₅ | CH₃ |
| SO₂CH₃ | (2-) OCH₃ | H | CH₃ |
| SO₂CH₃ | (2-) OCH₃ | CH₃ | CH₃ |
| SO₂CH₃ | (2-) OCH₃ | C₂H₅ | CH₃ |
| SO₂CH₃ | (2-) OCH₃ | C₃H₇ | CH₃ |
| SO₂CH₃ | (2-) OCH₃ | C₃H₇-i | CH₃ |
| SO₂CH₃ | (2-) OCH₃ | C₄H₉ | CH₃ |
| SO₂CH₃ | (2-) OCH₃ | C₄H₉-i | CH₃ |
| SO₂CH₃ | (2-) OCH₃ | C₄H₉-s | CH₃ |
| SO₂CH₃ | (2-) OCH₃ | C₄H₉-t | CH₃ |
| SO₂CH₃ | (2-) OCH₃ |  | CH₃ |
| SO₂CH₃ | (2-) OCH₃ |  | CH₃ |
| SO₂CH₃ | (2-) OCH₃ | CH=CHCH₃ | CH₃ |
| SO₂CH₃ | (2-) OCH₃ |  | CH₃ |
| SO₂CH₃ | (2-) OCH₃ |  | CH₃ |
| SO₂CH₃ | (2-) OCH₃ |  | CH₃ |
| SO₂CH₃ | (2-) OCH₃ | N(CH₃)₂ | CH₃ |
| SO₂CH₃ | (2-) OCH₃ |  | CH₃ |
| SO₂CH₃ | (2-) OCH₃ | Cl | CH₃ |
| SO₂CH₃ | (2-) OCH₃ | Br | CH₃ |
| Cl | (2-) OCH₃ | CF₃ |  |

-continued

| R³ | (position-) (R⁴)ₙ | R⁵ | R⁶ |
|---|---|---|---|
| Cl | (2-) OCH₃ | SCH₃ |  |
| Cl | (2-) OCH₃ | SC₂H₅ |  |
| Cl | (2-) OCH₃ | SC₃H₇ |  |
| Cl | (2-) OCH₃ | SC₃H₇-i |  |
| Cl | (2-) OCH₃ |  |  |
| Cl | (2-) OCH₃ |  |  |
| Cl | (2-) OCH₃ |  |  |
| Cl | (2-) OCH₃ |  |  |
| Cl | (2-) OCH₃ |  |  |
| Cl | (2-) OCH₃ | SCH=C=CH₂ |  |
| Cl | (2-) OCH₃ | SCH₂CN |  |
| Cl | (2-) OCH₃ | SCH₂CH₂CN |  |
| Cl | (2-) OCH₃ | OCH₃ |  |
| Cl | (2-) OCH₃ | OC₂H₅ |  |
| Cl | (2-) OCH₃ | OC₃H₇ |  |
| Cl | (2-) OCH₃ | OC₃H₇-i |  |

-continued

| R³ | (position-) (R⁴)ₙ | R⁵ | R⁶ |
|---|---|---|---|
| Cl | (2-) OCH₃ | OC₄H₉ |  |
| Cl | (2-) OCH₃ | OCH₂CF₃ |  |
| Cl | (2-) OCH₃ | 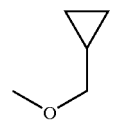 |  |
| Cl | (2-) OCH₃ | OC₆H₅ |  |
| Cl | (2-) OCH₃ | H |  |
| Cl | (2-) OCH₃ | CH₃ |  |
| Cl | (2-) OCH₃ | C₂H₅ |  |
| Cl | (2-) OCH₃ | C₃H₇ |  |
| Cl | (2-) OCH₃ | C₃H₇-i |  |
| Cl | (2-) OCH₃ | C₄H₉ |  |
| Cl | (2-) OCH₃ | C₄H₉-i |  |
| Cl | (2-) OCH₃ | C₄H₉-s |  |
| Cl | (2-) OCH₃ | C₄H₉-t |  |
| Cl | (2-) OCH₃ |  |  |
| Cl | (2-) OCH₃ |  |  |
| Cl | (2-) OCH₃ | CH=CHCH₃ |  |
| Cl | (2-) OCH₃ |  |  |

-continued

| R³ | (position-) (R⁴)ₙ | R⁵ | R⁶ |
|---|---|---|---|
| Cl | (2-) OCH₃ |  |  |
| Cl | (2-) OCH₃ |  |  |
| Cl | (2-) OCH₃ | N(CH₃)₂ |  |
| Cl | (2-) OCH₃ |  |  |
| Cl | (2-) OCH₃ | Cl |  |
| Cl | (2-) OCH₃ | Br |  |
| SO₂CH₃ | (2-) OCH₃ | CF₃ |  |
| SO₂CH₃ | (2-) OCH₃ | SCH₃ |  |
| SO₂CH₃ | (2-) OCH₃ | SC₂H₅ |  |
| SO₂CH₃ | (2-) OCH₃ | SC₃H₇ |  |
| SO₂CH₃ | (2-) OCH₃ | SC₃H₇-i |  |
| SO₂CH₃ | (2-) OCH₃ |  |  |
| SO₂CH₃ | (2-) OCH₃ |  |  |
| SO₂CH₃ | (2-) OCH₃ |  |  |
| SO₂CH₃ | (2-) OCH₃ |  |  |

-continued

| R³ | (position-) (R⁴)ₙ | R⁵ | R⁶ |
|---|---|---|---|
| SO₂CH₃ | (2-) OCH₃ | CH₂-S-cyclopropyl | cyclopropyl |
| SO₂CH₃ | (2-) OCH₃ | SCH=C=CH₂ | cyclopropyl |
| SO₂CH₃ | (2-) OCH₃ | SCH₂CN | cyclopropyl |
| SO₂CH₃ | (2-) OCH₃ | SCH₂CH₂CN | cyclopropyl |
| SO₂CH₃ | (2-) OCH₃ | OCH₃ | cyclopropyl |
| SO₂CH₃ | (2-) OCH₃ | OC₂H₅ | cyclopropyl |
| SO₂CH₃ | (2-) OCH₃ | OC₃H₇ | cyclopropyl |
| SO₂CH₃ | (2-) OCH₃ | OC₃H₇-i | cyclopropyl |
| SO₂CH₃ | (2-) OCH₃ | OC₄H₉ | cyclopropyl |
| SO₂CH₃ | (2-) OCH₃ | OCH₂CF₃ | cyclopropyl |
| SO₂CH₃ | (2-) OCH₃ | OCH₂-cyclopropyl (via O) | cyclopropyl |
| SO₂CH₃ | (2-) OCH₃ | OC₆H₅ | cyclopropyl |
| SO₂CH₃ | (2-) OCH₃ | H | cyclopropyl |
| SO₂CH₃ | (2-) OCH₃ | CH₃ | cyclopropyl |
| SO₂CH₃ | (2-) OCH₃ | C₂H₅ | cyclopropyl |
| SO₂CH₃ | (2-) OCH₃ | C₃H₇ | cyclopropyl |
| SO₂CH₃ | (2-) OCH₃ | C₃H₇-i | cyclopropyl |
| SO₂CH₃ | (2-) OCH₃ | C₄H₉ | cyclopropyl |
| SO₂CH₃ | (2-) OCH₃ | C₄H₉-i | cyclopropyl |
| SO₂CH₃ | (2-) OCH₃ | C₄H₉-s | cyclopropyl |
| SO₂CH₃ | (2-) OCH₃ | C₄H₉-t | cyclopropyl |
| SO₂CH₃ | (2-) OCH₃ | cyclopropyl | cyclopropyl |
| SO₂CH₃ | (2-) OCH₃ | CH₂-cyclopropyl | cyclopropyl |
| SO₂CH₃ | (2-) OCH₃ | CH=CHCH₃ | cyclopropyl |
| SO₂CH₃ | (2-) OCH₃ | C₆H₅ | cyclopropyl |
| SO₂CH₃ | (2-) OCH₃ | 4-Cl-C₆H₄ | cyclopropyl |
| SO₂CH₃ | (2-) OCH₃ | CH₂C₆H₅ | cyclopropyl |
| SO₂CH₃ | (2-) OCH₃ | N(CH₃)₂ | cyclopropyl |
| SO₂CH₃ | (2-) OCH₃ | morpholino | cyclopropyl |
| SO₂CH₃ | (2-) OCH₃ | Cl | cyclopropyl |
| SO₂CH₃ | (2-) OCH₃ | Br | cyclopropyl |
| Cl | (2-) OCH₃ | CF₃ | N(CH₃)₂ |
| Cl | (2-) OCH₃ | SCH₃ | N(CH₃)₂ |
| Cl | (2-) OCH₃ | SC₂H₅ | N(CH₃)₂ |
| Cl | (2-) OCH₃ | SC₃H₇ | N(CH₃)₂ |
| Cl | (2-) OCH₃ | SC₃H₇-i | N(CH₃)₂ |
| Cl | (2-) OCH₃ | SCH₂CH=CH₂ | N(CH₃)₂ |

-continued

| R³ | (position-) (R⁴)ₙ | R⁵ | R⁶ |
|---|---|---|---|
| Cl | (2-) OCH₃ | 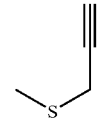 | N(CH₃)₂ |
| Cl | (2-) OCH₃ | 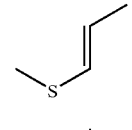 | N(CH₃)₂ |
| Cl | (2-) OCH₃ | 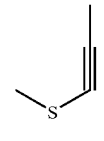 | N(CH₃)₂ |
| Cl | (2-) OCH₃ | 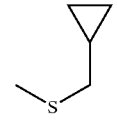 | N(CH₃)₂ |
| Cl | (2-) OCH₃ | SCH=C=CH₂ | N(CH₃)₂ |
| Cl | (2-) OCH₃ | SCH₂CN | N(CH₃)₂ |
| Cl | (2-) OCH₃ | SCH₂CH₂CN | N(CH₃)₂ |
| Cl | (2-) OCH₃ | OCH₃ | N(CH₃)₂ |
| Cl | (2-) OCH₃ | OC₂H₅ | N(CH₃)₂ |
| Cl | (2-) OCH₃ | OC₃H₇ | N(CH₃)₂ |
| Cl | (2-) OCH₃ | OC₃H₇-i | N(CH₃)₂ |
| Cl | (2-) OCH₃ | OC₄H₉ | N(CH₃)₂ |
| Cl | (2-) OCH₃ | OCH₂CF₃ | N(CH₃)₂ |
| Cl | (2-) OCH₃ | 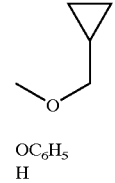 | N(CH₃)₂ |
| Cl | (2-) OCH₃ | OC₆H₅ | N(CH₃)₂ |
| Cl | (2-) OCH₃ | H | N(CH₃)₂ |
| Cl | (2-) OCH₃ | CH₃ | N(CH₃)₂ |
| Cl | (2-) OCH₃ | C₂H₅ | N(CH₃)₂ |
| Cl | (2-) OCH₃ | C₃H₇ | N(CH₃)₂ |
| Cl | (2-) OCH₃ | C₃H₇-i | N(CH₃)₂ |
| Cl | (2-) OCH₃ | C₄H₉ | N(CH₃)₂ |
| Cl | (2-) OCH₃ | C₄H₉-i | N(CH₃)₂ |
| Cl | (2-) OCH₃ | C₄H₉-s | N(CH₃)₂ |
| Cl | (2-) OCH₃ | C₄H₉-t | N(CH₃)₂ |
| Cl | (2-) OCH₃ | 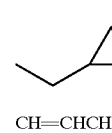 | N(CH₃)₂ |
| Cl | (2-) OCH₃ | 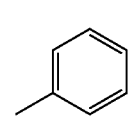 | N(CH₃)₂ |
| Cl | (2-) OCH₃ | CH=CHCH₃ | N(CH₃)₂ |
| Cl | (2-) OCH₃ | 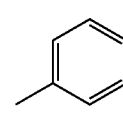 | N(CH₃)₂ |
| Cl | (2-) OCH₃ | 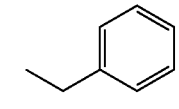 | N(CH₃)₂ |
| Cl | (2-) OCH₃ | 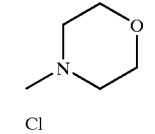 | N(CH₃)₂ |
| Cl | (2-) OCH₃ | N(CH₃)₂ | N(CH₃)₂ |
| Cl | (2-) OCH₃ | 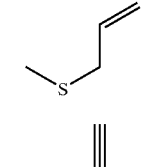 | N(CH₃)₂ |
| Cl | (2-) OCH₃ | Cl | N(CH₃)₂ |
| Cl | (2-) OCH₃ | Br | N(CH₃)₂ |
| SO₂CH₃ | (2-) OCH₃ | CF₃ | N(CH₃)₂ |
| SO₂CH₃ | (2-) OCH₃ | SCH₃ | N(CH₃)₂ |
| SO₂CH₃ | (2-) OCH₃ | SC₂H₅ | N(CH₃)₂ |
| SO₂CH₃ | (2-) OCH₃ | SC₃H₇ | N(CH₃)₂ |
| SO₂CH₃ | (2-) OCH₃ | SC₃H₇-i | N(CH₃)₂ |
| SO₂CH₃ | (2-) OCH₃ | 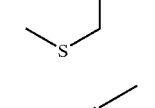 | N(CH₃)₂ |
| SO₂CH₃ | (2-) OCH₃ | 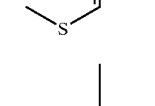 | N(CH₃)₂ |
| SO₂CH₃ | (2-) OCH₃ | 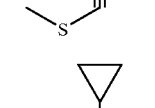 | N(CH₃)₂ |
| SO₂CH₃ | (2-) OCH₃ | 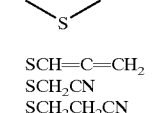 | N(CH₃)₂ |
| SO₂CH₃ | (2-) OCH₃ | 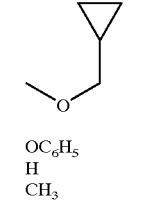 | N(CH₃)₂ |
| SO₂CH₃ | (2-) OCH₃ | SCH=C=CH₂ | N(CH₃)₂ |
| SO₂CH₃ | (2-) OCH₃ | SCH₂CN | N(CH₃)₂ |
| SO₂CH₃ | (2-) OCH₃ | SCH₂CH₂CN | N(CH₃)₂ |
| SO₂CH₃ | (2-) OCH₃ | OCH₃ | N(CH₃)₂ |
| SO₂CH₃ | (2-) OCH₃ | OC₂H₅ | N(CH₃)₂ |
| SO₂CH₃ | (2-) OCH₃ | OC₃H₇ | N(CH₃)₂ |
| SO₂CH₃ | (2-) OCH₃ | OC₃H₇-i | N(CH₃)₂ |
| SO₂CH₃ | (2-) OCH₃ | OC₄H₉ | N(CH₃)₂ |
| SO₂CH₃ | (2-) OCH₃ | OCH₂CF₃ | N(CH₃)₂ |
| SO₂CH₃ | (2-) OCH₃ |  | N(CH₃)₂ |
| SO₂CH₃ | (2-) OCH₃ | OC₆H₅ | N(CH₃)₂ |
| SO₂CH₃ | (2-) OCH₃ | H | N(CH₃)₂ |
| SO₂CH₃ | (2-) OCH₃ | CH₃ | N(CH₃)₂ |
| SO₂CH₃ | (2-) OCH₃ | C₂H₅ | N(CH₃)₂ |
| SO₂CH₃ | (2-) OCH₃ | C₃H₇ | N(CH₃)₂ |
| SO₂CH₃ | (2-) OCH₃ | C₃H₇-i | N(CH₃)₂ |
| SO₂CH₃ | (2-) OCH₃ | C₄H₉ | N(CH₃)₂ |
| SO₂CH₃ | (2-) OCH₃ | C₄H₉-i | N(CH₃)₂ |

-continued

| R³ | (position-) (R⁴)ₙ | R⁵ | R⁶ |
|---|---|---|---|
| SO₂CH₃ | (2-) OCH₃ | C₄H₉-s | N(CH₃)₂ |
| SO₂CH₃ | (2-) OCH₃ | C₄H₉-t | N(CH₃)₂ |
| SO₂CH₃ | (2-) OCH₃ | cyclopropyl | N(CH₃)₂ |
| SO₂CH₃ | (2-) OCH₃ | cyclopropylmethyl | N(CH₃)₂ |
| SO₂CH₃ | (2-) OCH₃ | CH=CHCH₃ | N(CH₃)₂ |
| SO₂CH₃ | (2-) OCH₃ | tolyl | N(CH₃)₂ |
| SO₂CH₃ | (2-) OCH₃ | 4-chlorobenzyl | N(CH₃)₂ |
| SO₂CH₃ | (2-) OCH₃ | benzyl-CH₂ | N(CH₃)₂ |
| SO₂CH₃ | (2-) OCH₃ | N(CH₃)₂ | N(CH₃)₂ |
| SO₂CH₃ | (2-) OCH₃ | morpholinylmethyl | N(CH₃)₂ |
| SO₂CH₃ | (2-) OCH₃ | Cl | N(CH₃)₂ |
| SO₂CH₃ | (2-) OCH₃ | Br | N(CH₃)₂ |
| Cl | (2-) OCH₃ | CH₃ | OCH₃ |
| Cl | (2-) OCH₃ | C₂H₅ | OCH₃ |
| Cl | (2-) OCH₃ | C₃H₇ | OCH₃ |
| Cl | (2-) OCH₃ | SCH₃ | OCH₃ |
| Cl | (2-) OCH₃ | SC₂H₅ | OCH₃ |
| Cl | (2-) OCH₃ | OCH₃ | OCH₃ |
| Cl | (2-) OCH₃ | OC₂H₅ | OCH₃ |
| Cl | (2-) OCH₃ | CH₃ | OC₂H₅ |
| Cl | (2-) OCH₃ | C₂H₅ | OC₂H₅ |
| Cl | (2-) OCH₃ | C₃H₇ | OC₂H₅ |
| Cl | (2-) OCH₃ | SCH₃ | OC₂H₅ |
| Cl | (2-) OCH₃ | SC₂H₅ | OC₂H₅ |
| Cl | (2-) OCH₃ | OCH₃ | OC₂H₅ |
| Cl | (2-) OCH₃ | OC₂H₅ | OC₂H₅ |
| SO₂CH₃ | (2-) OCH₃ | Cl | OCH₃ |
| SO₂CH₃ | (2-) OCH₃ | Br | OCH₃ |
| SO₂CH₃ | (2-) OCH₃ | CH₃ | OCH₃ |
| SO₂CH₃ | (2-) OCH₃ | C₂H₅ | OCH₃ |
| SO₂CH₃ | (2-) OCH₃ | C₃H₇ | OCH₃ |
| SO₂CH₃ | (2-) OCH₃ | SCH₃ | OCH₃ |
| SO₂CH₃ | (2-) OCH₃ | SC₂H₅ | OCH₃ |
| SO₂CH₃ | (2-) OCH₃ | OCH₃ | OC₂H₅ |
| SO₂CH₃ | (2-) OCH₃ | OC₂H₅ | OC₂H₅ |
| SO₂CH₃ | (2-) OCH₃ | CH₃ | OC₂H₅ |
| SO₂CH₃ | (2-) OCH₃ | C₂H₅ | OC₂H₅ |
| SO₂CH₃ | (2-) OCH₃ | C₃H₇ | OC₂H₅ |
| SO₂CH₃ | (2-) OCH₃ | SCH₃ | OC₂H₅ |
| SO₂CH₃ | (2-) OCH₃ | SC₂H₅ | OC₂H₅ |
| SO₂CH₃ | (2-) OCH₃ | OCH₃ | OC₂H₅ |

Group 10

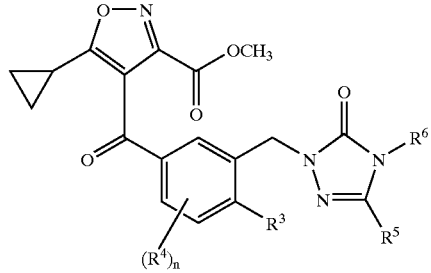

(IB-2)

Here, $R^3$, $(R^4)_n$, $R^5$ and $R^6$ have, for example, the meanings given for Group 9.

Group 11

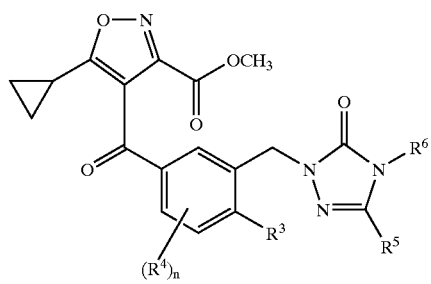

(IB-3)

Here, $R^3$, $(R^4)_n$, $R^5$ and $R^6$ have, for example, the meanings given for Group 9.

Group 12

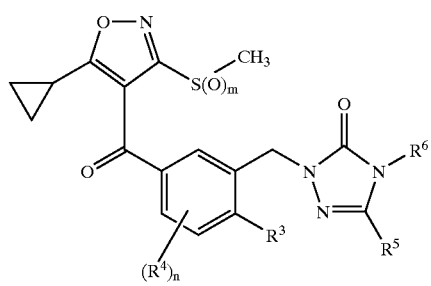

(IB-4)

Here, $R^3$, $(R^4)_n$, $R^5$ and $R^6$ have, for example, the meanings given for Group 9, and m represents the number 0, 1 or 2.

Group 13

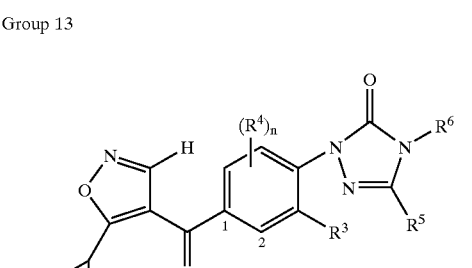

(IC1)

Here, $R^3$, $(R^4)_n$, $R^5$ and $R^6$ have, for example, the meanings given for Group 9.

Group 14

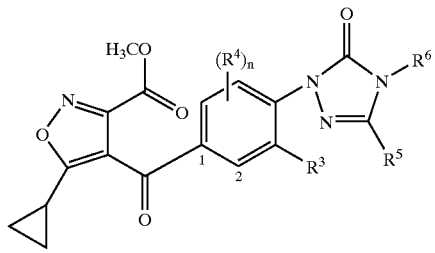
(IC-2)

Here, $R^3$, $(R^4)_n$, $R^5$ and $R^6$ have, for example, the meanings given for Group 9.

Group 15

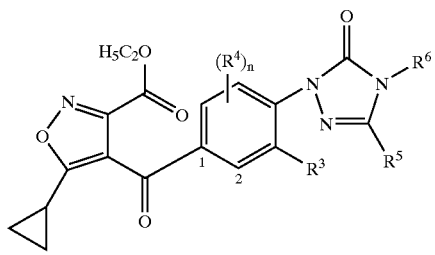
(IC-3)

Here, $R^3$, $(R^4)_n$, $R^5$ and $R^6$ have, for example, the meanings given for Group 9.

Group 16

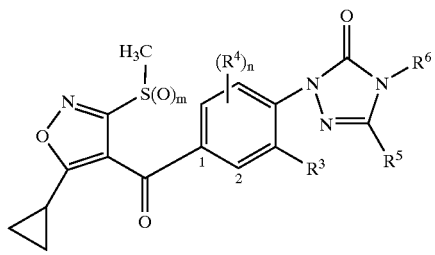
(IC-4)

Here, $R^3$, $(R^4)_n$, $R^5$ and $R^6$ have, for example, the meanings given for Group 9, and m represents the number 0, 1 or 2.

The novel substituted benzoylisoxazoles of the general formula (I) have strong and selective herbicidal activity.

The novel substituted benzoylisoxazoles of the general formula (I) are obtained when (a) benzoylisoxazoles of the general formula (II)

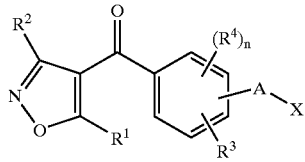
(II)

in which
n, A, $R^1$, $R^2$, $R^3$ and $R^4$ are each as defined above and
X represents halogen
are reacted with heterocycles of the general formula (III)

H—Z (III)

in which
Z is as defined above,
if appropriate in the presence of one or more reaction auxiliaries and if appropriate in the presence of one or more diluents,
or when
if $R^2$ is hydrogen
(b) benzoyl ketones of the general formula (IV)

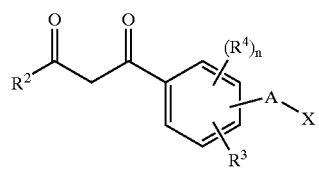
(IV)

in which
n, A, $R^1$, $R^3$, $R^4$ and Z are each as defined above
are reacted with a trialkyl orthoformate or an N,N-dimethylformamide dialkyl acetal and subsequently with hydroxylamine or an acid adduct thereof,
if appropriate in the presence of one or more reaction auxiliaries and if appropriate in the presence of one or more diluents,
or when
if $R^2$ represents optionally substituted alkoxycarbonyl
(c) benzoyl ketones of the general formula (IV)

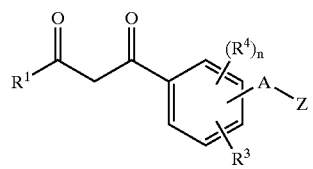
(IV)

in which
n, A, $R^1$, $R^3$, $R^4$ and Z are each as defined above
are reacted with an alkyl cyanoformate and then with hydroxylamine or an acid adduct thereof, or with an alkyl chloro-hydroximino-acetate, if appropriate in the presence of one or more reaction auxiliaries and if appropriate in the presence of one or more diluents,
or when
if $R^2$ represents alkylthio
(d) benzoyl ketones of the general formula (IV)

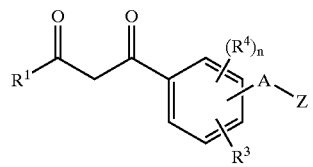
(IV)

in which
n, A, $R^1$, $R^3$, $R^4$ and Z are each as defined above
are reacted with carbon disulphide and with an alkylating agent and then with hydroxylamine or an acid adduct thereof,
if appropriate in the presence of one or more reaction auxiliaries and if appropriate in the presence of one or more diluents, and electrophilic or nucleophilic substitutions and/or oxidations or reductions within the scope of the definition of the substituents are, if appropriate, subsequently carried out in a customary manner on the compounds of the formula (I) obtained according to processes (a) to (d).

The compounds of the formula (I) can be converted by customary methods into other compounds of the formula (I) according to the above definition, for example by nucleophilic substitution (for example $R^5$: Cl→$OC_2H_5$, $SCH_3$) or by oxidation (for example $R^5$: $CH_2SCH_3$→$CH_2S(O)CH_3$).

In the preparation of compounds of the general formula (I), it is also possible that compounds of the general formula (IE)

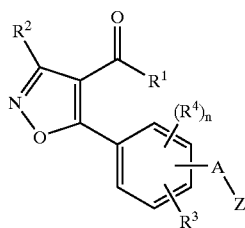

in which n, A, $R^1$, $R^2$, $R^3$, $R^4$ and Z are each as defined above are formed in certain amounts.

The compounds of the general formula (IE) also form, as novel substances, part of the subject-matter of the present application.

Using, for example, (3-chloromethyl-4-trifluoromethyl-phenyl)-(3,5-dimethyl-isoxazol-4-yl)-methanone and 4-methyl-5-trifluoromethyl-2,4-dihydro-3H-1,2,4-triazol-3-one as starting materials, the course of the reaction in the process (a) according to the invention can be illustrated by the following formula scheme:

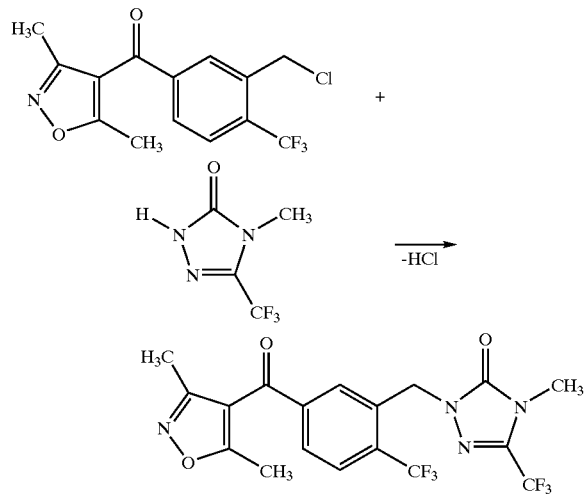

Using, for example, 1-[2-chloro-3-(3,4-dimethyl-5-oxo-4,5-dihydro-[1,2,4-triazol-1-yl-methyl)-phenyl]-pentane-1,3-dione, N,N-dimethyl-formamide diethyl acetal and hydroxylamine as starting materials, the course of the reaction in the process (b) according to the invention can be illustrated by the following formula scheme:

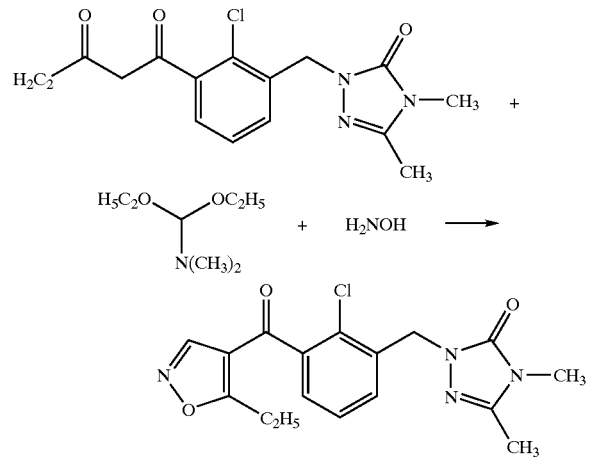

Using, for example, 1-[2-chloro-3-(4-ethoxy-3-ethyl-5-oxo-4,5-dihydro-1,2,4-triazol-1-yl-methyl)-phenyl]-3-cyclopropyl-propane1,3-dione, ethyl cyanoformate and hydroxylamine as starting materials, the course of the reaction in the process (c) according to the invention can be illustrated by the following formula scheme:

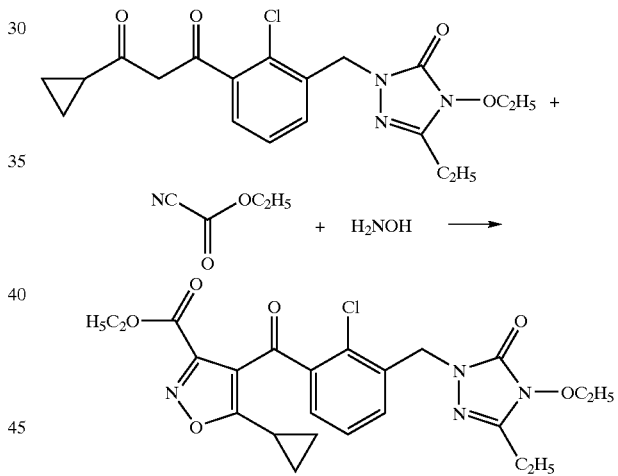

Using, for example, 1-[2-chloro-3-(4-methyl-3-methylthio-5-oxo-4,5-dihydro-1,2,4-triazol-1-yl-methyl)-phenyl]-3-cyclopropyl-propane-1,3-dione, carbon disulphide, methyl bromide and hydroxylamine as starting materials, the course of the reaction in the process (d) according to the invention can be illustrated by the following formula scheme:

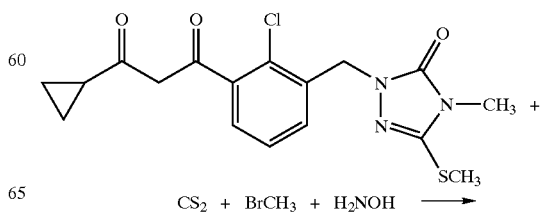

-continued

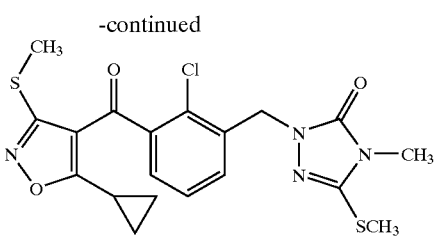

The formula (II) provides a general definition of the benzoylisoxazoles to be used as starting materials in the process (a) according to the invention for preparing compounds of the general formula (I). In the general formula (II), n, A, $R^1$, $R^2$, $R^3$ and $R^4$ each preferably have those meanings which have already been mentioned above, in connection with the description of the compounds of the general formula (I) according to the invention, as being preferred, particularly preferred, very particularly preferred or most preferred for n, A, $R^1$, $R^2$, $R^3$ and $R^4$; X preferably represents fluorine, chlorine, bromine or iodine, in particular chlorine or bromine.

Except for ethyl 4-(2-bromo-methyl-benzoyl)-5-cyclopropyl-isoxazole-3-carboxylate (cf. WO-A-95/31446), the starting materials of the general formula (II) have hitherto not been disclosed in the literature; except for ethyl 4-(2-bromo-methyl-benzoyl)-5-cyclopropyl-isoxazole-3-carboxylate, they also form, as novel substances, part of the subject-matter of the present application.

The novel benzoylisoxazoles of the general formula (II) are obtained when benzoylisoxazoles of the general formula (V)

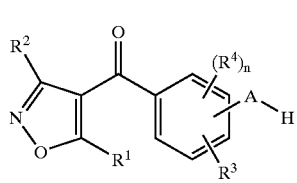

in which
n, A, $R^1$, $R^2$, $R^3$ and $R^4$ are each as defined above
are reacted with a side-chain halogenating agent, such as, for example, N-bromo-succinimide or N-chloro-succinimide, under UV light: or in the presence of a reaction auxiliary, such as, for example, 2,2'-azo-bis-isobutyronitrile, in the presence of a diluent, such as, for example, carbon tetrachloride, at temperatures between 0° C. and 100° C. (cf. WO-A-95/31446; Preparation Examples).

The intermediates of the general formula (V) are known and/or can be prepared by processes known per se (cf. WO-A-95/31446; Preparation Examples).

The formula (III) provides a general definition of the heterocycles further to be used as starting materials in the process (a) according to the invention for preparing compounds of the general formula (I). In the general formula (III), Z preferably has that meaning which has already been mentioned above, in connection with the description of the compounds of the general formula (I) according to the invention, as being preferred for Z.

The starting materials of the general formula (III) are known and/or can be prepared by processes known per se.

The formula (IV) provides a general defintion of the benzoyl ketones to be used as starting materials in the processes (b), (c) and (d) according to the invention for preparing compounds of the general formula (I). In the general formula (IV), n, A, $R^1$, $R^3$, $R^4$ and Z each preferably have those meanings which have already been mentioned above, in connection with the description of the compounds of the general formula (I) according to the invention, as being preferred, particularly preferred, very particularly preferred or most preferred for n, A, $R^1$, $R^3$, $R^4$ and Z.

The starting materials of the general formula (IV) have hitherto not been disclosed in the literature; they also, as novel substances, form part of the subject-matter of the present application.

The novel benzoyl ketones of the general formula (IV) are obtained when ketones of the general formula (VI)

in which
$R^1$ is as defined above,
are reacted with benzoic acid derivatives of the general formula (VII)

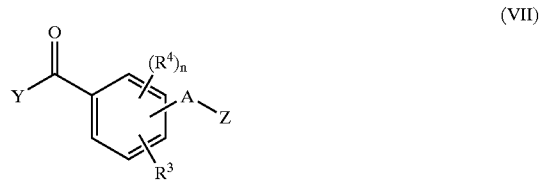

in which
n, A, $R^3$, $R^4$ and Z are each as defined above, and
Y represents halogen (in particular fluorine, chlorine or bromine) or represents optionally substituted alkoxy (in particular methoxy, ethoxy or ethoxy ethoxy),
if appropriate in the presence of a reaction auxiliary, such as, for example, sodium hydride, and if appropriate in the presence of a diluent, such as, for example, tetrahydrofuran, at temperatures between 0° C. and 100° C. (cf. the Preparation Examples).

The benzoic acid derivatives of the general formula (VII) required as intermediates are known and/or can be prepared by processes known per se (cf. DE-A-38 39 480, DE-A-42 39 296, EP-A-597 360, EP-A609 734, DE-A-43 03 676, EP-A-617 026, DE-A-44 05 614, U.S. Pat. No. 5,378,681).

The benzoic acid derivatives of the general formula (VII) are obtained when halogeno(alkyl)benzoic acid derivatives of the general formula (VIII)

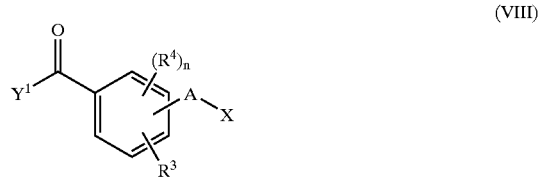

in which
n, A, $R^3$ and $R^4$ are each as defined above and
X represents halogen (in particular fluorine, chlorine or bromine) and
$Y^1$ represents optionally substituted alkoxy (in particular methoxy, ethoxy or ethoxyethoxy), are reacted with compounds of the general formula (III),

in which

Z is as defined above, if appropriate in the presence of a reaction auxiliary, such as, for example, sodium hydride, triethylamine or potassium carbonate, and if appropriate in the presence of a diluent, such as, for example, acetone, acetonitrile, N,N-dimethylformamide or N,N-dimethyl-acetamide, at temperatures between 50° C. and 200° C. (cf. the Preparation Examples).

The halogeno(alkyl)benzoic acid derivatives of the formula (VIII) required as intermediates are known and/or can be prepared by processes known per se (cf. EP-A-90 369, EP-A-93 488, EP-A-399 732, EP-A-480 641, EP-A-609 798, EP-A-763 524, DE-A-21 26 720, WO-A-93103722, WO-A-97/38977, U.S. Pat. No. 3,978,127, U.S. Pat. No. 4,837,333).

The process (b) according to the invention for preparing the compounds of the formula (I) is carried out using orthoformic esters or N,N-dimethylformamide acetates. These compounds preferably contain alkyl groups having 1 to 4 carbon atoms, in particular methyl or ethyl. Examples which may be mentioned are trimethyl orthoformate, triethyl orthoformate, N,N-dimethyl-formamide dimethyl acetal and N,N-dimethyl-formamide diethyl acetal.

The process (c) according to the invention for preparing the compounds of the formula (I) is carried out using alkyl cyanoformates or alkyl chloro-hydroximino-acetates. These compounds preferably contain alkyl groups having 1 to 4 carbon atoms, in particular methyl or ethyl. Examples which may be mentioned are methyl cyanoformate, ethyl cyanoformate, methyl chloro-hydroximino-acetate and ethyl chloro-hydroximino-acetate.

The process (d) according to the invention for preparing the compounds of the formula (I) is carried out using (carbon disulphide and) alkylating agents. These compounds preferably contain alkyl groups having 1 to 4 carbon atoms, in particular methyl or ethyl. Examples which may be mentioned are methyl chloride, methyl bromide, methyl iodide, dimethyl sulphate, ethyl chloride, ethyl bromide, ethyl iodine and diethyl sulphate.

The processes (b), (c) and—if appropriate—(d) according to the invention for preparing the compounds of the formula (I) are carried out using hydroxylamine or an acid adduct thereof. A preferred acid adduct which may be mentioned is hydroxylamine hydrochloride.

The processes according to the invention for preparing the compounds of the general formula (I) are preferably carried out using diluents. Suitable diluents for carrying out the processes (a), (b), (c) and (d) according to the invention are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether, ketones, such as acetone, butanone or methyl isobutyl ketone; nitrites, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

Suitable reaction auxiliaries for the processes (a), (b), (c) and (d) according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hyride, potassium hydride or calcium hydride, lithium hydroxide, sodium hydroxide, potassium hydroxide or calcium hydroxide, sodium methoxide, ethoxide, n- or i-propoxide, n-, i-, s- or -t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine tributylamine ethyl-diisopropylamine N,N-dimethyl-cyclohexylamine, dicyclohexylamine ethyl-dicyclohexylamine, N,N-dimethylaniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methyl-pyridine, 4-di-methylamino-pyridine, N-methylpiperidine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

When carrying out the processes (a), (b), (c) and (d) according to the invention, the reaction temperatures can be varied within a relatively wide range. In general, the processes are carried out at temperatures between 0° C. and 150° C., preferably between 10° C. and 120° C.

The processes according to the invention are generally carried out under atmospheric pressure. However, it is also possible to carry out the processes according to the invention under elevated or reduced pressure—in general between 0.1 bar and 10 bar.

For carrying out the processes according to the invention, the starting materials are generally employed in approximately equimolar amounts. However, it is also possible for one of the components to be used in a relatively large excess. The reaction is generally carried out in a suitable diluent in the presence of a reaction auxiliary, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants: *Dicotyledonous* weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

*Dicotyledonous* crops of the genera: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.*

*Monocotyledonous* weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.*

*Monocotyledonous* crops of the genera: *Oryza, Zea, Triticum, Hordeum, Avena, Secale, Sorghum, Panicum, Saccharum, Ananas, Asparagus, Allium.*

However, the use of the active compounds according to the invention is in no way restricted to these genera, but also extends in the same manner to other plants.

Depending on the concentration, the compounds according to the invention are suitable for total weed control, for example on industrial terrain and rail tracks and on paths and areas with or without tree growth. Equally, the compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention have strong herbicidal activity and a broad activity spectrum when used on the soil and on above-ground parts of plants. To a certain extent they are also suitable for selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amicarbazone, amidochlor, amidosulfuron, anilofos, asulam, atrazine, azafenidin, azimsulfuron, benazolin(-ethyl), benfuresate, bensulfuron(-methyl), bentazone, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxy- fen, chloramben, chloridazon, chlorimuron(-ethyl), chlornitrofen, chlorosulftiron, chlorotoluron, cinidon (-ethyl), cinmethylin, cinosulfuron, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop (-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron (-methyl), ethofumesate, ethoxyfen, ethoxysulfuron, etobenzanid, fenoxaprop-(-P-ethyl), flamprop(-isopropyl), flamprop(-isopropyl-L), flamprop(-methyl), flazasulfuron, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-P-methyl), hexazinone, imazamethabenz-(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, picolinafen, piperophos, pretilachlor primisulfuron(-methyl), procarbazone, prometryn, propachlor, propanil, propaquizafop, propisochlor, propyzamide, prosulfocarb, prosulfuron, pyraflufen(-ethyl), pyrazolate, pyrazosulfuron (-ethyl), pyrazoxyfen, pyribenzoxim, pyributicarb, pyridate, pyriminobac(-methyl), pyrithiobac(-sodium), quinchlorac, quimnerac, quinoclamine, quizalofop(-P-ethyl), quizalofop (-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin, triflusulfuron and tritosuilfron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

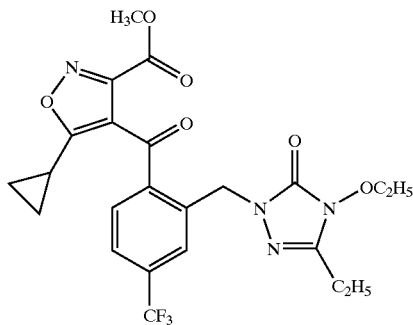

(Process (a))

At room temperature (about 20° C.), a solution of 1.20 g (33% pure, i.e. 2.8 mMol) of methyl 4-(3-bromomethyl-5-trifluoromethyl-benzoyl)-5-cyclopropyl-isoxazole-3-carboxylate in 10 ml of N,N-dimethyl-formamide is added dropwise with stirring to a mixture of 0.44 g (2.8 mMol) of 4-ethoxy-5-ethyl-2,4-dihydro-3H-1,2,4-triazol-3-one, 84 mg (2.8 mMol) of sodium hydride (75% pure) and 20 ml of N,N-dimethyl-formamide, and the reaction mixture is stirred at room temperature for 30 minutes. The mixture is then diluted with saturated aqueous sodium chloride solution to about twice its original volume and extracted twice with ethyl acetate. The combined organic extract solutions are dried with sodium sulphate and filtered. The filtrate is concentrated under water pump vacuum and the residue is purified by column chromatography (silica gel, hexanelethyl acetate, vol.: 7/3).

This gives 0.45 g (96% of theory based on 33% pure starting material) of (5-cyclopropyl-3-methoxycarbonyl-isoxazol-4-yl)-[2-(4-ethoxy-3-ethyl-5-oxo-4,5-dihydro-[1,2,4]-triazol-1-yl-methyl)-4-trifluoromethyl-phenyl]-methanone as an amorphous product.

logP (determined at pH=2.3): 3.56.

Example 2

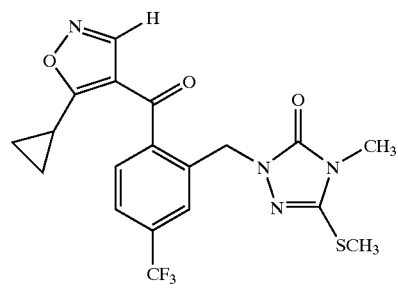

(process (b))

A mixture of 1.5 g (36 mMol) of 1-cyclopropyl-3-[2-(4-methyl-3-methylthio-5-oxo-4,5-dihydro-[1,2,4]-triazol-1-yl-methyl)4trifluoromethyl-phenyl]-propane-1,3Aione, 0.56 g (46 mMol) of N,N-dimethyl-formamide dimethyl acetal and 15 ml of toluene is stirred at 90° C. for 60 minutes. The mixture is then concentrated under water pump vacuum, the residue is taken up in 15 ml of ethanol and the mixture is, after addition of 0.25 g (36 mMol) of hydroxylamine hydrochloride, stirred at room temperature (about. 20° C. ) for two hours. The mixture is concentrated under water pump vacuum, the residue is shaken with methylene chloride/water and the organic phase is separated off, washed with saturated aqueous sodium chloride solution, dried with sodium sulphate and filtered. The filtrate is concentrated under water pump vacuum and the residue is purified by column chromatography (silica gel, ethyl acetate/hexane, vol: 1/1).

This gives 0.20 g (13% of theory) of (5-cyclopropyl-isoxazol-4-yl)-[2-(4-methyl-3-methylthio-5-oxo-4,5-dihydro-[1,2,4]-triazol-1-yl-methyl)-4-trifluoromethyl-phenyl]-methanone as an amorphous product.

logP (determined at pH=2.3): 2.94.

Analogously to Examples 1 and 2, and in accordance with the general description of the preparation process according to the invention, it is also possible to prepare, for example, the compound of the general formula (I)—or of the formulate (IA), (IB), (IC) of (ID)—listed in Tables 1 and 1a below.

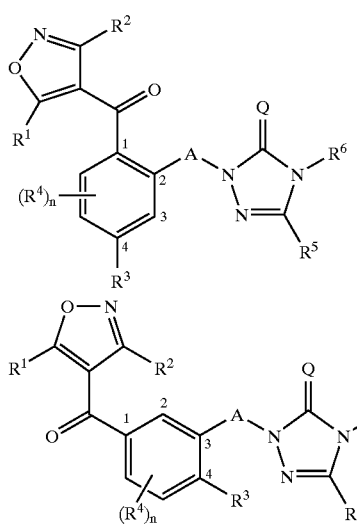

(IA)

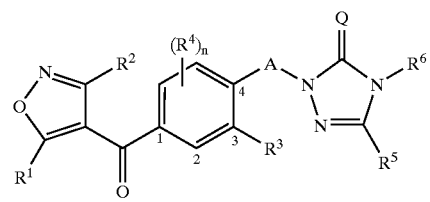

(IB)

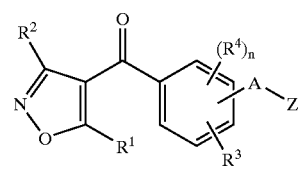

(IC)

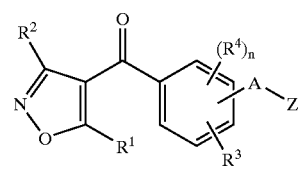

(ID)

TABLE 1

Examples of the compounds of the formulae (I) or (IA), (IB), (IC)

| Ex.-No. | A | Q | R¹ | R² | R³ | (position) (R⁴)ₙ | R⁵ | R⁶ | (Formula) physical data |
|---|---|---|---|---|---|---|---|---|---|
| 3 | CH₂ | O | cyclopropyl | CH₂C(O)OCH₃ | Br | — | OC₂H₅ | CH₃ | (IA) logP = 3.15[a] |
| 4 | CH₂ | O | cyclopropyl | CH₂C(O)OCH₃ | Br | — | C₂H₅ | OC₂H₅ | (IA) logP = 3.36[b] |
| 5 | CH₂ | O | cyclopropyl | CH₂C(O)OCH₃ | Br | — | CF₃ | CH₃ | (IA) logP = 3.50[a] |
| 6 | CH₂ | O | cyclopropyl | CH₂C(O)OCH₃ | CF₃ | — | OC₂H₅ | CH₃ | (IA) logP = 3.32[a] |
| 7 | CH₂ | O | cyclopropyl | CH₂C(O)OCH₃ | CF₃ | — | SCH₃ | CH₃ | (IA) logP = 3.22[a] |
| 8 | CH₂ | O | cyclopropyl | H | Cl | (2) Cl | CF₃ | CH₃ | (IB) ¹H-NMR (DMSO-D₆, δ): 8.7 ppm |
| 9 | CH₂ | O | cyclopropyl | H | F | — | SCH₃ | CH₃ | (IA) ¹H-NMR (CDCl₃, δ): 8.3 ppm |

TABLE 1-continued

Examples of the compounds of the formulae (I) or (IA), (IB), (IC)

| Ex.-No. | A | Q | R$^1$ | R$^2$ | R$^3$ | (position) (R$^4$)$_n$ | R$^5$ | R$^6$ | (Formula) physical data |
|---|---|---|---|---|---|---|---|---|---|
| 10 | CH$_2$ | O | cyclopropyl | H | Cl | (2) OCH$_3$ | CF$_3$ | CH$_3$ | (IB) $^1$H-NMR (DMSO-D$_6$, δ): 8.6 ppm |
| 11 | CH$_2$ | O | cyclopropyl | H | Cl | (2) Cl | OC$_2$H$_5$ | CH$_3$ | (IB) $^1$H-NMR (DMSO-D$_6$, δ): 8.7 ppm |
| 12 | CH$_2$ | O | cyclopropyl | H | Cl | (2) Cl | OCH$_3$ | CH$_3$ | (IB) $^1$H-NMR (DMSO-D$_6$, δ): 8.7 ppm |
| 13 | CH$_2$ | O | cyclopropyl | H | CF$_3$ | — | OCH$_3$ | CH$_3$ | (IA) |

TABLE 1a

Examples of the compounds of the formula (I) or (ID)

| Ex.-No. | R$^1$ | R$^2$ | (position) R$^3$ | (position) (R$^4$)$_n$ | (position) —A—Z | physical data |
|---|---|---|---|---|---|---|
| ID-1 | cyclopropyl | H | (2) Cl | (4) Cl | (3) 1-ethyl-3-methyl-imidazolidin-2-one | logP = 2.48$^{a)}$ |
| ID-2 | cyclopropyl | H | (2) OCH$_3$ | (4) Cl | (3) 1-ethyl-3-methyl-imidazolidin-2-one | logP = 2.46$^{a)}$ |
| ID-3 | cyclopropyl | H | (2) Cl | (4) Cl | (3) 1-ethyl-3-ethyl-imidazolidin-2-one | |
| ID-4 | cyclopropyl | H | (2) OCH$_3$ | (4) Cl | (3) 1-ethyl-3-ethyl-imidazolidin-2-one | |
| ID-5 | cyclopropyl | H | (2) Cl | (4) Cl | (3) 1-ethyl-3-methyl-tetrahydropyrimidin-2-one | |

TABLE 1a-continued

Examples of the compounds of the formula (I) or (ID)

| Ex.-No. | R¹ | R² | (position) R³ | (position) (R⁴)ₙ | (position) —A—Z | physical data |
|---|---|---|---|---|---|---|
| ID-6 | cyclopropyl | H | (2) Cl | (4) Cl | (3) 1-ethyl-3-(n-propyl)imidazolidin-2-one | |
| ID-7 | cyclopropyl | H | (2) Cl | (4) Cl | (3) 1-ethyl-3-(i-propyl)imidazolidin-2-one | |
| ID-8 | cyclopropyl | H | (2) Cl | (4) Cl | (3) 1-ethyl-3-(s-butyl)imidazolidin-2-one | |
| ID-9 | cyclopropyl | H | (2) Cl | (4) Cl | (3) 1-ethyl-3-(t-butyl)imidazolidin-2-one | |
| ID-10 | cyclopropyl | H | (2) OCH₃ | (4) Cl | (3) 1-ethyl-3-methyltetrahydropyrimidin-2-one | |
| ID-11 | cyclopropyl | H | (2) Cl | (4) SO₂CH₃ | (3) 1-ethyl-3-methylimidazolidin-2-one | |
| ID-12 | cyclopropyl | H | (2) Cl | (4) SO₂CH₃ | (3) 1-ethyl-3-methyltetrahydropyrimidin-2-one | |
| ID-13 | cyclopropyl | H | (2) SO₂CH₃ | (4) Cl | (3) 1-ethyl-3-methylimidazolidin-2-one | |

TABLE 1a-continued

Examples of the compounds of the formula (I) or (ID)

| Ex.-No. | R¹ | R² | (position) R³ | (position) (R⁴)ₙ | (position) —A—Z | physical data |
|---|---|---|---|---|---|---|
| ID-14 | cyclopropyl | H | (2) SO₂CH₃ | (4) Cl | (3) ethyl-methyl-tetrahydropyrimidin-2-one | |
| ID-15 | cyclopropyl | H | (2) Cl | (4) CF₃ | (3) ethyl-methyl-imidazolidin-2-one | |
| ID-16 | cyclopropyl | H | (2) Cl | (4) CF₃ | (3) ethyl-methyl-tetrahydropyrimidin-2-one | |
| ID-17 | cyclopropyl | H | (2) NO₂ | (4) CF₃ | (3) ethyl-methyl-imidazolidin-2-one | |
| ID-18 | cyclopropyl | H | (2) NO₂ | (4) CF₃ | (3) ethyl-methyl-tetrahydropyrimidin-2-one | |
| ID-19 | cyclopropyl | H | (2) OCH₃ | (4) CF₃ | (3) ethyl-methyl-imidazolidin-2-one | |
| ID-20 | cyclopropyl | H | (2) OCH₃ | (4) CF₃ | (3) ethyl-methyl-tetrahydropyrimidin-2-one | |
| ID-21 | cyclopropyl | H | (2) Cl | (4) CN | (3) ethyl-methyl-imidazolidin-2-one | |

TABLE 1a-continued

Examples of the compounds of the formula (I) or (ID)

| Ex.-No. | R¹ | R² | (position) R³ | (position) (R⁴)ₙ | (position) —A—Z | physical data |
|---|---|---|---|---|---|---|
| ID-22 | cyclopropyl | H | (2) Cl | (4) CN | (3) 1-ethyl-3-methyl-tetrahydropyrimidin-2-one | |
| ID-23 | cyclopropyl | H | (2) OCH₃ | (4) CN | (3) 1-ethyl-3-methyl-imidazolidin-2-one | |
| ID-24 | cyclopropyl | H | (2) OCH₃ | (4) CN | (3) 1-ethyl-3-methyl-tetrahydropyrimidin-2-one | |
| ID-25 | cyclopropyl | H | (2) Cl | (4) F | (3) 1-ethyl-3-methyl-imidazolidin-2-one | |
| ID-26 | cyclopropyl | H | (2) Cl | (4) F | (3) 1-ethyl-3-methyl-tetrahydropyrimidin-2-one | |
| ID-27 | cyclopropyl | H | H | — | (2) 1-ethyl-3-methyl-imidazolidin-2-one | |
| ID-28 | cyclopropyl | H | H | — | (2) 1-ethyl-3-methyl-tetrahydropyrimidin-2-one | |
| ID-29 | cyclopropyl | H | (4) F | — | (2) 1-ethyl-3-methyl-imidazolidin-2-one | |

TABLE 1a-continued

Examples of the compounds of the formula (I) or (ID)

| Ex.-No. | R¹ | R² | (position) R³ | (position) (R⁴)ₙ | (position) —A—Z | physical data |
|---|---|---|---|---|---|---|
| ID-30 | cyclopropyl | H | (4) F | — | (2) N-ethyl, N'-methyl tetrahydropyrimidin-2-one | |
| ID-31 | cyclopropyl | H | (4) Cl | — | (2) N-ethyl, N'-methyl imidazolidin-2-one | |
| ID-32 | cyclopropyl | H | (4) Cl | — | (2) N-ethyl, N'-methyl tetrahydropyrimidin-2-one | |
| ID-33 | cyclopropyl | H | (4) F | — | (2) N-ethyl, N'-ethyl imidazolidin-2-one | |
| ID-34 | cyclopropyl | H | (4) Cl | — | (2) N-ethyl, N'-ethyl imidazolidin-2-one | |
| ID-35 | cyclopropyl | H | (4) Br | — | (2) N-ethyl, N'-methyl imidazolidin-2-one | |
| ID-36 | cyclopropyl | H | (4) I | — | (2) N-ethyl, N'-methyl imidazolidin-2-one | |
| ID-37 | cyclopropyl | H | (4) NO₂ | — | (2) N-ethyl, N'-methyl imidazolidin-2-one | |

TABLE 1a-continued
Examples of the compounds of the formula (I) or (ID)
| Ex.-No. | R¹ | R² | (position) R³ | (position) (R⁴)ₙ | (position) —A—Z | physical data |
|---|---|---|---|---|---|---|
| ID-38 | 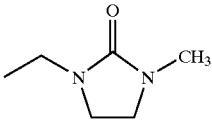 | H | (4) CN | — | (2) 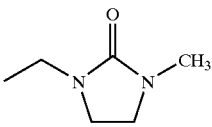 | |
| ID-39 | 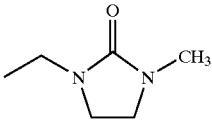 | H | (4) CF₃ | — | (2) 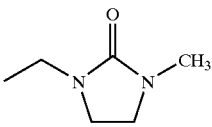 | |
| ID-40 | 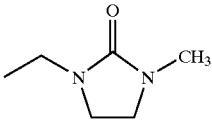 | H | (4) SO₂CH₃ | — | (2) 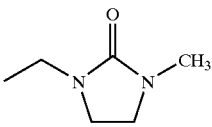 | |
| ID-41 | 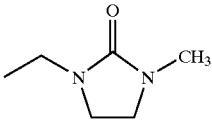 | H | (4) OCH₃ | — | (2) 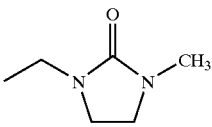 | |
| ID-42 | 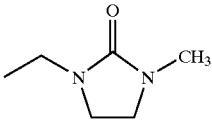 | H | (4) OCF₃ | — | (2) 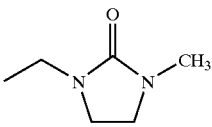 | |
| ID-43 | 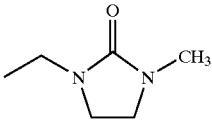 | H | (4) OCHF₂ | — | (2) 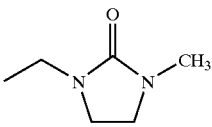 | |
| ID-44 | 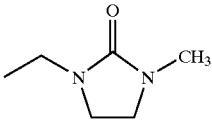 | H | (4) SCH₃ | — | (2) 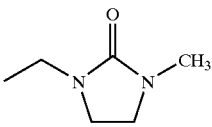 | |
| ID-45 | 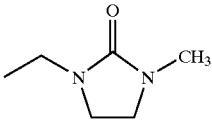 | H | (4) SOCH₃ | — | (2) 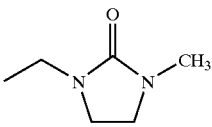 | |
| ID-46 | 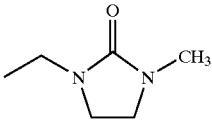 | 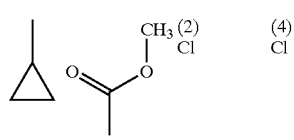 | (2) CH₃ Cl | (4) Cl | (3) 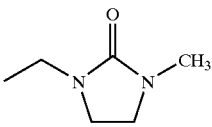 | |

TABLE 1a-continued

Examples of the compounds of the formula (I) or (ID)

| Ex.-No. | $R^1$ | $R^2$ | (position) $R^3$ | (position) $(R^4)_n$ | (position) —A—Z | physical data |
|---|---|---|---|---|---|---|
| ID-47 | cyclopropyl-CH$_3$ | CH$_3$-O-C(=O)-O- | (2) OCH$_3$ | (4) Cl | (3) N-ethyl-N'-methyl imidazolidinone | |
| ID-48 | cyclopropyl-CH$_3$ | CH$_3$-O-C(=O)-O- | (2) Cl | (4) Cl | (3) N-ethyl-N'-methyl tetrahydropyrimidinone | |
| ID-49 | cyclopropyl-CH$_3$ | CH$_3$-O-C(=O)-O- | (2) OCH$_3$ | (4) Cl | (3) N-ethyl-N'-methyl tetrahydropyrimidinone | |
| ID-50 | cyclopropyl | SCH$_3$ | (2) Cl | (4) Cl | (3) N-ethyl-N'-methyl imidazolidinone | |
| ID-51 | cyclopropyl | SCH$_3$ | (2) OCH$_3$ | (4) Cl | (3) N-ethyl-N'-methyl imidazolidinone | |
| ID-52 | cyclopropyl | SCH$_3$ | (2) Cl | (4) Cl | (3) N-ethyl-N'-methyl tetrahydropyrimidinone | |
| ID-53 | cyclopropyl | SCH$_3$ | (2) OCH$_3$ | (4) Cl | (3) N-ethyl-N'-methyl tetrahydropyrimidinone | |
| ID-54 | cyclopropyl | H | (2) Cl | (4) Cl | (3) N-ethyl-N'-ethyl tetrahydropyrimidinone | |

TABLE 1a-continued

Examples of the compounds of the formula (I) or (ID)

| Ex.-No. | R¹ | R² | (position) R³ | (position) (R⁴)ₙ | (position) —A—Z | physical data |
|---|---|---|---|---|---|---|
| ID-55 | cyclopropyl | H | (2) OCH₃ | (4) Cl | (3) N-ethyl-N'-ethyl tetrahydropyrimidin-2-one | |
| ID-56 | cyclopropyl | H | (2) Cl | (4) Cl | (3) N-ethyl-N'-isopropyl tetrahydropyrimidin-2-one | |
| ID-57 | cyclopropyl | H | (2) OCH₃ | (4) Cl | (3) N-ethyl-N'-isopropyl tetrahydropyrimidin-2-one | |
| ID-58 | cyclopropyl | H | (4) CF₃ | — | (2) N-ethyl-N'-methyl tetrahydropyrimidin-2-one | |
| ID-59 | cyclopropyl | H | (4) CF₃ | — | (2) N-ethyl-N'-ethyl imidazolidin-2-one | |
| ID-60 | cyclopropyl | H | (4) CF₃ | — | (2) N-ethyl-N'-ethyl tetrahydropyrimidin-2-one | |
| ID-61 | cyclopropyl | H | (2) Cl | (4) Cl | (3) N-ethyl oxazolidin-2-one | |
| ID-62 | cyclopropyl | H | (2) OCH₃ | (4) Cl | (3) N-ethyl oxazolidin-2-one | |

TABLE 1a-continued

Examples of the compounds of the formula (I) or (ID)

| Ex.-No. | R$^1$ | R$^2$ | (position) R$^3$ | (position) (R$^4$)$_n$ | (position) —A—Z | physical data |
|---|---|---|---|---|---|---|
| ID-63 | cyclopropyl | H | (2) Cl | (4) Cl | (3) N-ethyl, N'-cyclopropyl tetrahydropyrimidin-2-one | |
| ID-64 | cyclopropyl | H | (2) OCH$_3$ | (4) Cl | (3) N-ethyl, N'-cyclopropyl tetrahydropyrimidin-2-one | |
| ID-65 | cyclopropyl | H | (2) Cl | (4) Cl | (3) N-ethyl, N'-cyclopropyl imidazolidin-2-one | |
| ID-66 | cyclopropyl | H | (2) OCH$_3$ | (4) Cl | (3) N-ethyl, N'-cyclopropyl imidazolidin-2-one | |
| ID-67 | cyclopropyl | H | (2) NO$_2$ | (4) SO$_2$CH$_3$ | (3) N-ethyl, N'-C$_2$H$_5$ imidazolidin-2-one | |
| ID-68 | cyclopropyl | H | (2) NO$_2$ | (4) SO$_2$CH$_3$ | (3) N-ethyl, N'-CH$_3$ tetrahydropyrimidin-2-one | |
| ID-69 | cyclopropyl | H | (2) Cl | (4) SO$_2$CH$_3$ | (3) N-ethyl, N'-cyclopropyl imidazolidin-2-one | |
| ID-70 | cyclopropyl | H | (2) NO$_2$ | (4) SO$_2$CH$_3$ | (3) N-ethyl, N'-cyclopropyl imidazolidin-2-one | |

TABLE 1a-continued

Examples of the compounds of the formula (I) or (ID)

| Ex.-No. | R¹ | R² | (position) R³ | (position) (R⁴)ₙ | (position) —A—Z | physical data |
|---|---|---|---|---|---|---|
| ID-71 | cyclopropyl | H | (2) NO₂ | (4) CF₃ | (3) 1-ethyl-3-methyl-tetrahydropyrimidin-2-one | |
| ID-72 | cyclopropyl | H | (2) NO₂ | (4) CF₃ | (3) 1-cyclopropyl-3-ethyl-imidazolidin-2-one | |
| ID-73 | cyclopropyl | H | (2) NO₂ | (4) CF₃ | (3) 1-cyclopropyl-3-ethyl-imidazolidin-2-one | |
| ID-74 | cyclopropyl | H | (2) Cl | (4) SO₂CH₃ | (3) 1-tert-butyl-3-ethyl-imidazolidin-2-one | |
| ID-75 | cyclopropyl | H | (2) NO₂ | (4) SO₂CH₃ | (3) 1-tert-butyl-3-ethyl-imidazolidin-2-one | |
| ID-76 | cyclopropyl | H | (2) NO₂ | (4) CF₃ | (3) 1-tert-butyl-3-ethyl-imidazolidin-2-one | |
| ID-77 | cyclopropyl | H | (2) Cl | (4) SO₂CH₃ | (3) 1-tert-butyl-3-ethyl-tetrahydropyrimidin-2-one | |

TABLE 1a-continued

Examples of the compounds of the formula (I) or (ID)

| Ex.-No. | R¹ | R² | (position) R³ | (position) (R⁴)ₙ | (position) —A—Z | physical data |
|---|---|---|---|---|---|---|
| ID-78 | cyclopropyl | H | (2) NO₂ | (4) SO₂CH₃ | (3) N-ethyl-N'-tert-butyl cyclic urea | |
| ID-79 | cyclopropyl | H | (2) NO₂ | (4) CF₃ | (3) N-ethyl-N'-tert-butyl cyclic urea | |

The logP values given in Table 1 were determined in accordance with EE Directive 79/831 Annex V.A8 by HPLC (High Performance Liquid Chromatography) using a reverse-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding data in Table 1 are labelled [a].

(b) Mobile phases for the determination in the neutral range: 0.01 molar aqueous phosphate buffer solution, acetonitrile; linear gradient from 10% acetonitrile to 90% acetonitrile—the corresponding data in Table 1 are labelled [b].

Calibration was carried out using unbranched alkan-2-ones (with from 3 to 16 carbon atoms) whose logP values are known (determination of the logP values by the retention times using linear interpolation between two successive alkanones).

The lambda-max values were determined in the maxima of the chromatographic signals, using the UV spectra from 200 nm to 400 nm.

Starting Materials of the Formula (II)

Example (II-1)

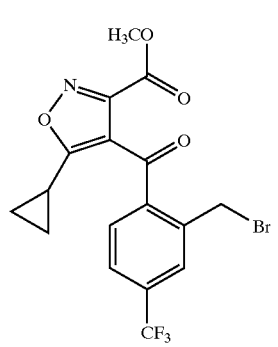

A mixture of 3.0 g (8.5 mMol) of methyl 5-cyclopropyl-4-(2-methyl-4-trifluoro-methyl-benzoyl)-isoxazole-4-carboxylate, 1.5 g (8.5 mMol) of N-bromo-succinimide, 0.15 g of 2,2'-azo-bis-isobutyronitrile and 45 ml of carbon tetrachloride is heated under reflux for two hours and, after cooling, filtered. The filtrate is diluted with methylene chloride to about twice its original volume, washed with 20% strength aqueous sodium hydrogen sulphite solution, dried with sodium sulphate and filtered. From the filtrate, the solvent is carefully distilled off under water pump vacuum.

This gives 2.5 g (68% of theory) of methyl 5-cyclopropyl-4-(2-bromomethyl4-trifluoromethyl-benzoyl)isoxazole4-carboxylate as an amorphous product which can be reacted further without any purification.

Analogously to Example (II-1), it is also possible to prepare, for example, the compounds of the formula (II) listed in Table 2 below.

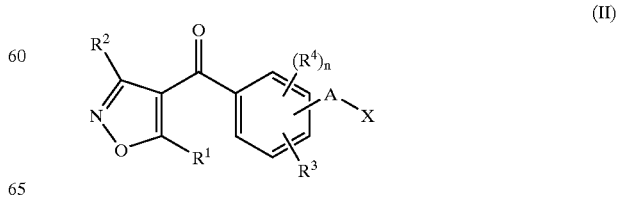

(II)

TABLE 2
Examples of the compounds of the formula (II)
| Ex.-No. | R¹ | R² | (position) R³ | (position) (R⁴)ₙ | (position) A-X | physical data |
|---|---|---|---|---|---|---|
| II-2 |  | 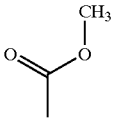 | (4) Br | — | (2) $CH_2Br$ | |
| II-3 |  | 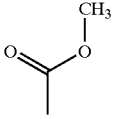 | (4) Cl | — | (2) $CH_2Br$ | |
| II-4 |  | 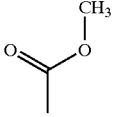 | (4) $CH_3$ | — | (2) $CH_2Br$ | |
| II-5 |  | 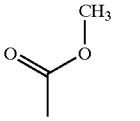 | (4) CN | — | (2) $CH_2Br$ | |
| II-6 |  | 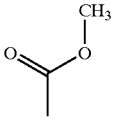 | (4) $OCH_3$ | — | (2) $CH_2Br$ | |
| II-7 |  | 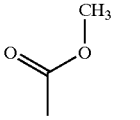 | (4) $SCH_3$ | — | (2) $CH_2Br$ | |
| II-8 |  | 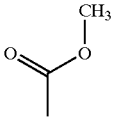 | (4) $SO_2CH_3$ | — | (2) $CH_2Br$ | |
| II-9 |  | 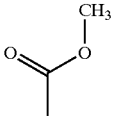 | (4) $SO_2N(CH_3)_2$ | — | (2) $CH_2Br$ | |
| II-10 |  | $SCH_3$ | (4) $CF_3$ | — | (2) $CH_2Br$ | |
| II-11 |  | 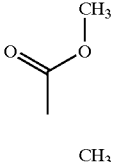 | (4) $OCHF_2$ | — | (2) $CH_2Br$ | |
| II-12 |  | 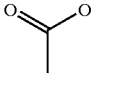 | (4) $OCF_3$ | — | (2) $CH_2Br$ | |

TABLE 2-continued

Examples of the compounds of the formula (II)

| Ex.-No. | R$^1$ | R$^2$ | (position) R$^3$ | (position) (R$^4$)$_n$ | (position) A-X | physical data |
|---|---|---|---|---|---|---|
| II-13 | cyclopropyl | -O-C(=O)-O-CH$_3$ (methyl carbonate) | (4) NO$_2$ | — | (2) CH$_2$Br | |
| II-14 | cyclopropyl | -O-C(=O)-O-CH$_3$ | (4) Cl | (2) Cl | (3) CH$_2$Br | |
| II-15 | cyclopropyl | H | (4) Cl | (2) Cl | (3) CH$_2$Br | |
| II-16 | cyclopropyl | -O-C(=O)-O-C$_2$H$_5$ | (4) Cl | (2) Cl | (3) CH$_2$Br | |
| II-17 | cyclopropyl | -O-C(=O)-O-C$_2$H$_5$ | H | — | (3) CH$_2$Br | |
| II-18 | cyclopropyl | H | H | — | (3) CH$_2$Br | |
| II-19 | cyclopropyl | H | (4) Cl | (2) OCH$_3$ | (3) CH$_2$Br | |
| II-20 | cyclopropyl | H | (4) CH$_3$ | (3) OCH$_3$ | (2) CH$_2$Br | |
| II-21 | cyclopropyl | H | (4) CN | (3) OCH$_3$ | (2) CH$_2$Br | |
| II-22 | cyclopropyl | H | (4) SO$_2$CH$_3$ | (3) CH$_2$OCH$_3$ | (2) CH$_2$Br | |
| II-23 | cyclopropyl | H | (4) CF$_3$ | (3) CH$_2$OCH$_3$ | (2) CH$_2$Br | |
| II-24 | cyclopropyl | H | (4) F | (2) Cl | (3) CH$_2$Br | |

Starting Materials of the Formula (IV)

Example (IV-1)

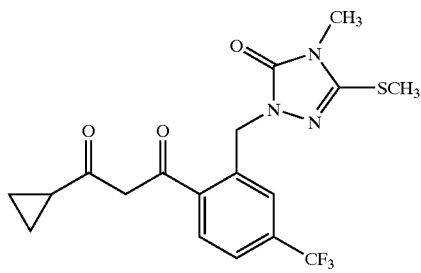

A mixture of 0.94 g (11 mMol) of cyclopropyl methyl ketone, 0.35 g (11 mMol) of sodium hydride (75% pure) and 15 ml of tetrahydrofuran is stirred at 20° C. for 30 minutes. A solution of 2.0 g (5.5 mMol) of 4-methyl-5-methylthio-2-(2-methoxycarbonyl-5-trifluoromethyl-benzyl)-2,4-dihydro-3H-1,2,4-triazol-3-one in 8 ml of tetrahydrofuran is then added dropwise and, after addition of 0.2 g of dibenzo-18-crone-6, the reaction mixture is heated under reflux for 60 minutes. After cooling to room temperature, the mixture is diluted with 100 ml of ethyl acetate, shaken with saturated aqueous ammonium chloride solution, dried with sodium sulphate and filtered through silica gel. From the filtrate, the solvent is carefully distilled off under water pump vacuum.

This gives 1.5 g (66% of theory) of 1-cyclopropyl-3-[4-methyl-3-methylthio-5-oxo-4,5-dihydro-[1,2,4]-triazol-1-yl-methyl)-phenyl]-propane-1,3-dione as an amorphous product which can be re acted further without purification.

Starting Materials of the Formula (VII)

Example (VII-1)

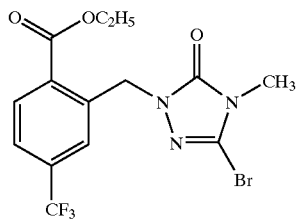

Step 1

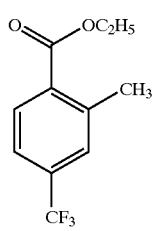

10 g (49 mMol) of 2-methyl-4-trifluoromethyl-benzoic acid are dissolved in 150 ml of ethanol and admixed with 1 ml of conc. sulphuric acid. The mixture is heated under reflux for 24 hours and then concentrated, the residue is taken up in methylene chloride and the mixture is extracted with saturated aqueous sodium bicarbonate solution. The methylene chloride phase is dried over sodium sulphate and concentrated under water pump vacuum.

This gives 9 g (80% of theory) of ethyl 2-methyl-4-trifluoromethyl-benzoate as an amorphous residue.

Step 2

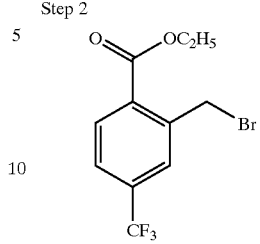

9 g (39 mMol) of ethyl 2-methyl-4-trifluoromethyl-benzoate are dissolved in 200 ml of carbon tetrachloride and admixed with 7 g (39 nMol) of N-bromo-succinimide and 0.1 g of dibenzoyl peroxide. After 6 hours of heating under reflux, the succinimide which has separated off is filtered off, and the filtrate is concentrated under water pump vacuum.

This gives 12 g of an amorphous residue which, in addition to ethyl 2-bromomethyl-4-trifluoromethyl-benzoate, contains 17% of ethyl 2,2-dibromomethyl-4-trifluoro-methyl-benzoate and 12% of ethyl 2-methyl-4-trifluoromethyl-benzoate.

Step 3

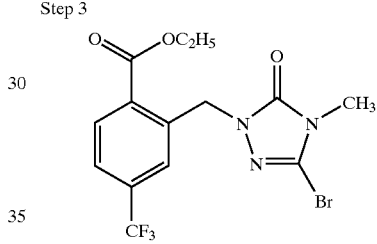

4 g of ethyl 2-bromomethyl-4-trifluoromethyl-benzoate (about 70% pure) and 2.28 g (12.8 mMol) of 5-bromo-4-methyl-2,4-dihydro-3H-1,2,4-triazol-3-one are dissolved in 150 ml of acetonitrile and the solution is admixed with 5.3 g (38.4 mMol) of potassium carbonate and heated under reflux with vigorous stirring for 2 hours. The reaction mixture is taken up in water and repeatedly extracted with methylene chloride. The combined methylene chloride phases are dried over sodium sulphate, concentrated under water pump vacuum and chromatographed.

This gives 2 g (38% of theory) of 5-bromo-4-methyl-2-(2-ethoxycarbonyl-5-trifluoromethyl-benzyl)-2,4-dihydro-3H-1,2,4-triazol-3-one as an amorphous product.

$^1$H-NMR (CDCl$_3$, δ): 5.46 ppm.

Example (VII-2)

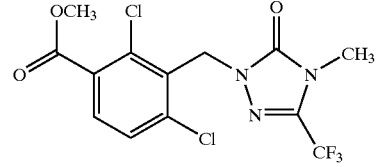

6.7 g (40mMol) of 4-methyl-5-trifluoromethyl-2,4-dihydro-3H-1,2,4-triazol-3-one are initially charged in 150 ml of acetonitrile and stirred with 11 g (80 mMol) of potassium carbonate. The mixture is heated to 50° C., and a solution of 13.1 g (44 mMol) of methyl 3-bromomethyl-2, 4-dichloro-benzoate in 20 ml of acetonitrile is then added dropwise with stirring, and the reaction mixture is heated with stirring and at reflux for another 15 hours. The mixture is then concentrated under water pump vacuum and the residue is taken up in methylene chloride, washed with 1N hydrochloric acid, dried with sodium sulphate and filtered. The filtrate is concentrated under reduced pressure, the residue is digested with petroleum ether and the resulting crysalline product is isolated by filtration with suction.

This gives 14.9 g (97% of theory) of 4-methyl-5-trifluoromethyl-2-(2,6-dichloro-3-methoxycarbonyl-benzyl)-2,4-dihydro-3H-1,2,4-triazol-3-one of melting point 109° C.

Analogously to the Examples (VII-1) and (VII-2), it is also possible to prepare, for example, the compounds of the general formula (VII) listed in Table 3 below.

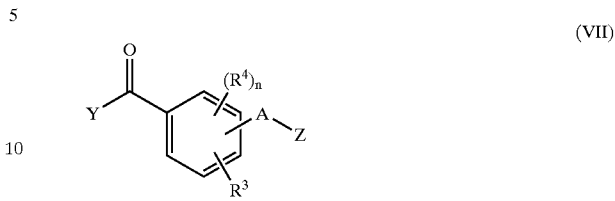

(VII)

TABLE 3

Examples of the compounds of the formula (VII)

| Ex. No. | (position) $R^3$ | (position) $(R^4)_n$ | (position) -A–Z | Y | physical data |
|---|---|---|---|---|---|
| VII-3 | (2-) Cl | (4-) Cl | (3-) [triazolinone with ethyl, CH₃, SCH₃] | OCH₃ | m.p.: 229° C. logP = 2.27[a] |
| VII-4 | (2-) Cl | (4-) Cl | (3-) [triazolinone with ethyl, CH₃, OC₂H₅] | OCH₃ | m.p.: 120° C. logP = 2.38[a] |
| VII-5 | (2-) Cl | (4-) Cl | (3-) [triazolinone with ethyl, cyclopropyl, cyclopropyl] | OCH₃ | m.p.: 127° C. logP = 2.55[a] |
| VII-6 | (2-) Cl | (4-) Cl | (3-) [triazolinone with ethyl, CH₃, OCH₃] | OCH₃ | m.p.: 121° C. logP = 2.04[a] |
| VII-7 | (2-) Cl | (4-) Cl | (3-) [triazolinone with ethyl, CH₃, OC₃H₇-i] | OCH₃ | m.p.: 68° C. logP = 2.73[a] |

TABLE 3-continued
Examples of the compounds of the formula (VII)
| Ex. No. | (position) R³ | (position) (R⁴)ₙ | (position) -A–Z | Y | physical data |
|---|---|---|---|---|---|
| VII-8 | (2-) Cl | (4-) Cl | (3-) 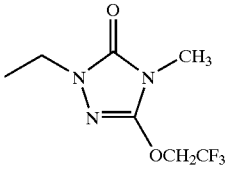 | OCH₃ | m.p.: 129° C. logP = 2.72[a] |
| VII-9 | (2-) Cl | (4-) Cl | (3-) 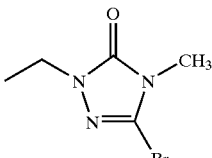 | OCH₃ | m.p.: 164° C. logP = 2.18[a] |
| VII-10 | (2-) Cl | (4-) Cl | (3-) 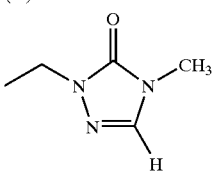 | OCH₃ | m.p.: 158° C. logP = 1.55[a] |
| VII-11 | (2-) Cl | (4-) Cl | (3-) 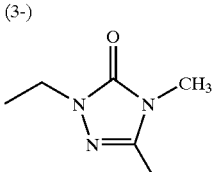 | OCH₃ | m.p.: 106° C. logP = 2.16[a] |
| VII-12 | (2-) Cl | (4-) Cl | (3-) 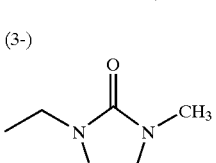 | OCH₃ | m.p.: 126° C. logP = 2.11[a] |
| VII-13 | (2-) Cl | (4-) Cl | (3-) 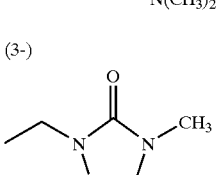 | OCH₃ | m.p.: 146° C. logP = 1.65[a] |
| VII-14 | (2-) Cl | (4-) Cl | (3-) 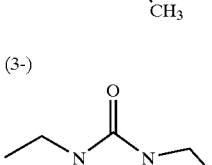 | OCH₃ | m.p.: 178° C. logP = 1.86[a] |

TABLE 3-continued

Examples of the compounds of the formula (VII)

| Ex. No. | (position) R³ | (position) (R⁴)ₙ | (position) -A-Z | Y | physical data |
|---|---|---|---|---|---|
| VII-15 | (2-) Cl | (4-) Cl | (3-) 2,4-dihydro-2-ethyl-4-cyclopropyl-5-methoxy-3H-1,2,4-triazol-3-one | OCH₃ | m.p.: 97° C. logP = 2.36[a] |
| VII-16 | (2-) Cl | (4-) Cl | (3-) 2,4-dihydro-2-ethyl-4-cyclopropyl-5-ethoxy-3H-1,2,4-triazol-3-one | OCH₃ | m.p.: 99° C. logP = 2.73[a] |
| VII-17 | (2-) Cl | (4-) Cl | (3-) 2,4-dihydro-2-ethyl-4-cyclopropyl-5-isopropoxy-3H-1,2,4-triazol-3-one | OCH₃ | m.p.: 56° C. logP = 3.08[a] |
| VII-18 | (2-) Cl | (4-) Cl | (3-) 2,4-dihydro-2-ethyl-4-cyclopropyl-5-(2,2,2-trifluoroethoxy)-3H-1,2,4-triazol-3-one | OCH₃ | m.p.: 102° C. logP = 3.05[a] |
| VII-19 | (2-) Cl | (4-) Cl | (3-) 2,4-dihydro-2-ethyl-4-cyclopropyl-5-methylthio-3H-1,2,4-triazol-3-one | OCH₃ | m.p.: 131° C. logP = 2.70[a] |
| VII-20 | (2-) Cl | (4-) Cl | (3-) 2,4-dihydro-2-ethyl-4-cyclopropyl-5-methyl-3H-1,2,4-triazol-3-one | OCH₃ | m.p.: 135° C. logP = 1.97[a] |
| VII-21 | (2-) Cl | (4-) Cl | (3-) 2,4-dihydro-2-ethyl-4-cyclopropyl-5-dimethylamino-3H-1,2,4-triazol-3-one | OCH₃ | m.p.: 143° C. logP = 2.42[a] |

TABLE 3-continued

Examples of the compounds of the formula (VII)

| Ex. No. | (position) R³ | (position) (R⁴)ₙ | (position) -A–Z | Y | physical data |
|---|---|---|---|---|---|
| VII-22 | (2-) Cl | (4-) Cl | (3-) *N-ethyl-4-ethoxy-5-ethyl-1,2,4-triazol-3(4H)-one* | OCH₃ | m.p.: 85° C. logP = 2.58[a] |
| VII-23 | (2-) Cl | (4-) Cl | (3-) *1-ethyl-3-methylimidazolidin-2-one* | OCH₃ | logP = 1.98[a] |
| VII-24 | (2-) Cl | (4-) Cl | (3-) *1-ethyl-3-methyltetrahydropyrimidin-2(1H)-one* | OCH₃ | logP = 2.07[a] |
| VII-25 | (2-) Cl | (4-) Cl | (3-) *2-ethyl-1,2-benzisothiazol-3(2H)-one 1,1-dioxide* | OCH₃ | m.p.: 157° C. logP = 2.94[a] |
| VII-26 | (4-) CF₃ | — | (2-) *1-ethyl-4-methyl-5-(methylsulfonyl)-1,2,4-triazol-3(4H)-one* | OC₂H₅ | ¹H-NMR (CDCl₃, δ): 5.53 ppm. |
| VII-27 | (4-) NO₂ | — | (3-) *1-ethyl-4-methyl-5-(trifluoromethyl)-1,2,4-triazol-3(4H)-one* | OC₂H₅ | ¹H-NMR (CDCl₃, δ): 5.48 ppm. |
| VII-28 | (4-) NO₂ | — | (3-) *1-ethyl-4-cyclopropyl-5-cyclopropyl-1,2,4-triazol-3(4H)-one* | OC₂H₅ | ¹H-NMR (CDCl₃, δ): 5.30 ppm. |

TABLE 3-continued
Examples of the compounds of the formula (VII)
| Ex. No. | (position) R³ | (position) (R⁴)ₙ | (position) -A-Z | Y | physical data |
|---|---|---|---|---|---|
| VII-29 | (4-) SO₂CH₃ | — | (3-) 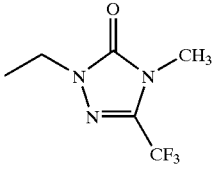 | OC₂H₅ | ¹H-NMR (CDCl₃, δ): 5.61 ppm. |
| VII-30 | (4-) Cl | — | (3-) 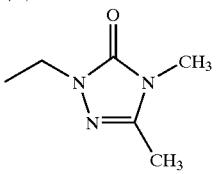 | OC₂H₅ | ¹H-NMR (CDCl₃, δ): 5.08 ppm. |
| VII-31 | (4-) Cl | — | (3-) 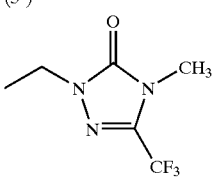 | OC₂H₅ | ¹H-NMR (CDCl₃, δ): 5.17 ppm. |
| VII-32 | (4-) Cl | — | (3-) 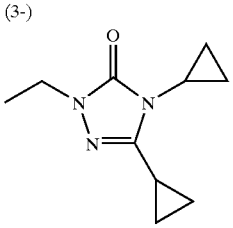 | OC₂H₅ | ¹H-NMR (CDCl₃, δ): 5.00 ppm |
| VII-33 | (4-) SO₂CH₃ | — | (2-) 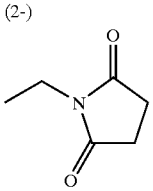 | OC₂H₅ | logP = 1.53[a)] |
| VII-34 | (4-) Br | — | (2-) 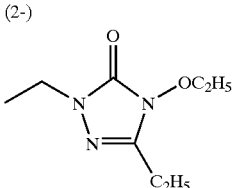 | OC₂H₅ | logP = 3.24[a)] |
| VII-35 | (4-) Br | — | (2-) 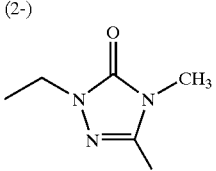 | OC₂H₅ | logP = 3.40[a)] |

TABLE 3-continued

Examples of the compounds of the formula (VII)

| Ex. No. | (position) R³ | (position) (R⁴)ₙ | (position) -A–Z | Y | physical data |
|---|---|---|---|---|---|
| VII-36 | (4-) F | — | (3-) 1-ethyl-4-methyl-5-bromo-1,2,4-triazol-3(4H)-one | OC₂H₅ | logP = 2.41[a)] |
| VII-37 | (4-) F | — | (2-) 1-ethyl-4-methyl-5-methylthio-1,2,4-triazol-3(4H)-one | OC₂H₅ | logP = 2.45[a)] |
| VII-38 | (4-) Br | — | (3-) 1-ethyl-4,5-dimethyl-1,2,4-triazol-3(4H)-one | OC₂H₅ | logP = 2.06[a)] |
| VII-39 | (4-) Br | — | (3-) 1-ethyl-4-methyl-5-bromo-1,2,4-triazol-3(4H)-one | OC₂H₅ | logP = 2.64[a)] |
| VII-40 | (4-) Br | — | (3-) 1-ethyl-4-methyl-5-trifluoromethyl-1,2,4-triazol-3(4H)-one | OC₂H₅ | logP = 3.23[a)] |
| VII-41 | (4-) Br | — | (3-) 1-ethyl-4,5-dicyclopropyl-1,2,4-triazol-3(4H)-one | OC₂H₅ | logP = 3.02[a)] |
| VII-42 | (4-) Cl | — | (2-) 1-ethyl-4-cyclopropyl-5-ethoxy-1,2,4-triazol-3(4H)-one | OC₂H₅ | logP = 3.23[a)] |

TABLE 3-continued

Examples of the compounds of the formula (VII)

| Ex. No. | (position) R³ | (position) (R⁴)ₙ | (position) -A-Z | Y | physical data |
|---|---|---|---|---|---|
| VII-43 | (4-) Cl | — | (2-) ethyl-methyl-triazolinone with CF₃ | OC₂H₅ | logP = 3.31[a] |
| VII-44 | (4-) Cl | — | (2-) ethyl-OC₂H₅-triazolinone with C₂H₅ | OC₂H₅ | logP = 3.14[a] |
| VII-45 | (4-) NO₂ | — | (2-) ethyl-cyclopropyl-triazolinone with OC₂H₅ | OC₂H₅ | logP = 2.42[a] |
| VII-46 | (4-) NO₂ | — | (2-) ethyl-methyl-triazolinone with SCH₃ | OC₂H₅ | logP = 2.82[a] |
| VII-47 | (4-) CF₃ | — | (2-) ethyl-cyclopropyl-triazolinone with OC₂H₅ | OC₂H₅ | logP = 3.48[a] |
| VII-48 | (4-) CF₃ | — | (2-) ethyl-OC₂H₅-triazolinone with C₂H₅ | OC₂H₅ | logP = 3.38[a] |
| VII-49 | (4-) CF₃ | — | (2-) ethyl-methyl-triazolinone with SCH₃ | OC₂H₅ | logP = 3.02[a] |

TABLE 3-continued
Examples of the compounds of the formula (VII)
| Ex. No. | (position) R³ | (position) (R⁴)ₙ | (position) -A–Z | | Y | physical data |
|---|---|---|---|---|---|---|
| VII-50 | (4-) CF₃ | — | (2-) | 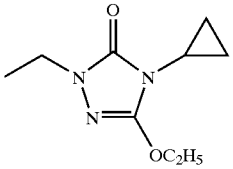 | OC₃H₇ | logP = 3.91[a)] |
| VII-51 | (4-) OCH₃ | — | (2-) | 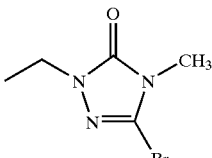 | OC₂H₅ | |
| VII-52 | (4-) OCH₃ | — | (2-) | 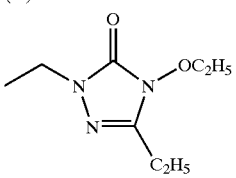 | OC₂H₅ | |
| VII-53 | (4-) CF₃ | — | (2-) | 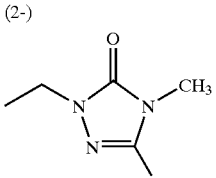 | OC₂H₅ | ¹H-NMR (CDCl₃, δ): 5.37 ppm. |
| VII-54 | (4-) CF₃ | — | (2-) | 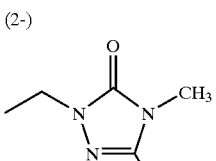 | OC₂H₅ | ¹H-NMR (CDCl₃, δ): 5.37 ppm. |
| VII-55 | — | — | (2-) | 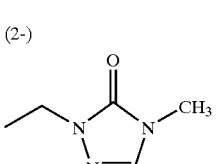 | OC₂H₅ | |
| VII-56 | — | — | (2-) | 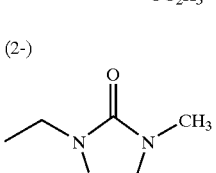 | OC₂H₅ | ¹H-NMR (CDCl₃, δ): 5.37 ppm. |

TABLE 3-continued

Examples of the compounds of the formula (VII)

| Ex. No. | (position) R³ | (position) (R⁴)ₙ | (position) -A–Z | Y | physical data |
|---|---|---|---|---|---|
| VII-57 | — | — | (2-) [1-ethyl-4-ethoxy-5-ethyl-1,2,4-triazol-3(4H)-one] | OC₂H₅ | ¹H-NMR (CDCl₃, δ): 5.40 ppm. |
| VII-58 | (4-) Br | — | (2-) [1-ethyl-4-methyl-5-ethoxy-1,2,4-triazol-3(4H)-one] | OC₂H₅ | logP = 2.95[a)] |
| VII-59 | (4-) Br | — | (2-) [1-ethyl-4-methyl-5-methoxy-1,2,4-triazol-3(4H)-one] | OC₂H₅ | ¹H-NMR (CDCl₃, δ): 5.31 ppm. |
| VII-60 | (4-) Br | — | (2-) [1-ethyl-pyrrolidine-2,5-dione] | OC₂H₅ | logP = 2.44[a)] |
| VII-61 | (4-) F | — | (2-) [1-ethyl-4-methyl-5-ethoxy-1,2,4-triazol-3(4H)-one] | OC₂H₅ | ¹H-NMR (CDCl₃, δ): 5.35 ppm. |
| VII-62 | (4-) F | — | (2-) [1-ethyl-4-methyl-5-trifluoromethyl-1,2,4-triazol-3(4H)-one] | OC₂H₅ | ¹H-NMR (CDCl₃, δ): 5.53 ppm. |
| VII-63 | (4-) F | — | (2-) [1-ethyl-4-ethoxy-5-ethyl-1,2,4-triazol-3(4H)-one] | OC₂H₅ | ¹H-NMR (CDCl₃, δ): 5.40 ppm. |

TABLE 3-continued

Examples of the compounds of the formula (VII)

| Ex. No. | (position) R³ | (position) (R⁴)ₙ | (position) -A-Z | Y | physical data |
|---|---|---|---|---|---|
| VII-64 | (4-) F | — | (2-) ethyl-N,N'-triazolone with OCH₃ and CH₃ | OC₂H₅ | ¹H-NMR (CDCl₃, δ): 5.36 ppm. |
| VII-65 | (4-) Br | — | (2-) ethyl-N,N'-triazolone with OC₃H₇-i and CH₃ | OC₂H₅ | logP = 3.34[a] |
| VII-66 | (4-) Br | — | (2-) ethyl-N,N'-triazolone with OC₃H₇-n and CH₃ | OC₂H₅ | logP = 3.38[a] |
| VII-67 | (4-) Br | — | (2-) ethyl-N,N'-triazolone with OCH₂CF₃ and CH₃ | OC₂H₅ | logP = 3.31[a] |
| VII-68 | (4-) Br | — | (2-) ethyl-fused pyrrolo-triazolone | OC₂H₅ | logP = 2.16[a] |
| VII-69 | (4-) Br | — | (2-) ethyl-fused pyrido-triazolone | OC₂H₅ | logP = 2.41[a] |
| VII-70 | (4-) CF₃ | — | (2-) ethyl-N,N'-triazolone with OC₃H₇-i and CH₃ | OC₂H₅ | logP = 3.51[a] |

TABLE 3-continued

Examples of the compounds of the formula (VII)

| Ex. No. | (position) R³ | (position) (R⁴)ₙ | (position) -A–Z | | Y | physical data |
|---|---|---|---|---|---|---|
| VII-71 | (4-) CF₃ | — | (2-) | 1-ethyl-4-methyl-5-(n-propoxy)-1,2,4-triazol-3(2H)-one | OC₂H₅ | logP = 3.54[a] |
| VII-72 | (4-) Br | — | (2-) | 3-ethyl-oxazolidin-2-one | OC₂H₅ | logP = 2.36[a] |
| VII-73 | (4-) Br | — | (2-) | 3-ethyl-5-methyl-1,3,4-oxadiazol-2(3H)-one | OC₂H₅ | logP = 2.88[a] |
| VII-74 | (4-) CF₃ | — | (2-) | 2-methyl-4-ethyl-1,2,4-triazol-3(4H)-one | OC₂H₅ | logP = 2.68[a] |
| VII-75 | (4-) Br | — | (2-) | 1-ethyl-4-methyl-5-bromo-1,2,4-triazol-3(2H)-one | OC₂H₅ | logP = 2.80[a] |
| VII-76 | (4-) CF₃ | — | (3-) | 1-ethyl-4-cyclopropyl-5-methoxy-1,2,4-triazol-3(2H)-one | OC₂H₅ | logP = 3.87[a] |
| VII-77 | (4-) CF₃ | — | (2-) | 1-ethyl-4-cyclopropyl-5-(methoxymethyl)-1,2,4-triazol-3(2H)-one | OC₂H₅ | logP = 2.88[a] |

TABLE 3-continued
Examples of the compounds of the formula (VII)
| Ex. No. | (position) R³ | (position) (R⁴)ₙ | (position) -A-Z | Y | physical data |
|---|---|---|---|---|---|
| VII-78 | (4-) CF₃ | — | (2-) 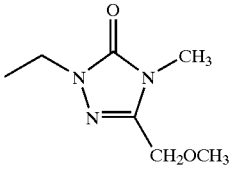 | OC₂H₅ | logP = 2.60[a)] |
| VII-79 | (4-) CF₃ | — | (2-) 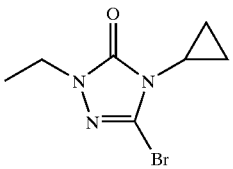 | OC₂H₅ | logP = 3.35[a)] |
| VII-80 | (4-) Br | — | (2-) 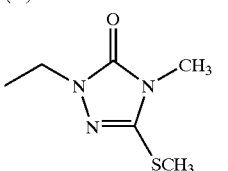 | OC₂H₅ | logP = 2.86[a)] |
| VII-81 | (4-) Cl | — | (2-) 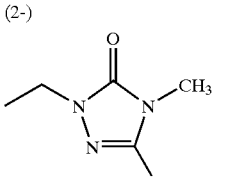 | OC₂H₅ | logP = 2.83[a)] |
| VII-82 | (4-) Br | — | (2-) 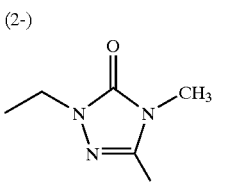 | OC₂H₅ | logP = 2.60[a)] |
| VII-83 | (4-) CF₃ | — | (2-) 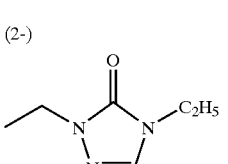 | OC₂H₅ | ¹H-NMR (CDCl₃, δ): 5.36 ppm. |
| VII-84 | (4-) CF₃ | — | (2-) 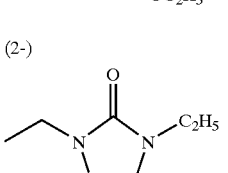 | OC₂H₅ | ¹H-NMR (CDCl₃, δ): 5.37 ppm. |

TABLE 3-continued

Examples of the compounds of the formula (VII)

| Ex. No. | (position) R³ | (position) (R⁴)ₙ | (position) -A–Z | Y | physical data |
|---|---|---|---|---|---|
| VII-85 | (4-) CF₃ | — | (2-) ethyl-methyl-triazolinone with N(CH₃)₂ | OC₂H₅ | logP = 2.79[a] |
| VII-86 | (4-) CF₃ | — | (2-) N-ethyl benzisothiazolone dioxide | OC₂H₅ | logP = 3.67[a] |
| VII-87 | (4-) CF₃ | — | (2-) N-ethyl phthalimide | OC₂H₅ | logP = 3.80[a] |
| VII-88 | (3-) CH₃ | — | (2-) ethyl-methyl-triazolinone with OC₂H₅ | OC₂H₅ | logP = 2.54[a] |
| VII-89 | (4-) SO₂CH₃ | — | (2-) ethyl-methyl-triazolinone with SCH₃ | OC₂H₅ | logP = 1.82[a] |
| VII-90 | (4-) CF₃ | — | (2-) N-ethyl-5-trifluoromethyl uracil | OC₂H₅ | logP = 2.93[a] |
| VII-91 | (4-) CF₃ | — | (2-) ethyl-cyclopropyl-triazolinone with OCH₃ | OC₂H₅ | logP = 3.08[a] |

TABLE 3-continued

Examples of the compounds of the formula (VII)

| Ex. No. | (position) R³ | (position) (R⁴)ₙ | (position) -A–Z | Y | physical data |
|---|---|---|---|---|---|
| VII-92 | (4-) CF₃ | — | (2-) 3-methyl-4-ethyl-1,3,4-oxadiazol-2(3H)-one | OC₂H₅ | logP = 3.04[a] |
| VII-93 | (4-) CF₃ | — | (2-) 1-ethyl-4-methyl-5-(OCH₂CF₃)-1,2,4-triazol-3(4H)-one | OC₂H₅ | logP = 3.45[a] |
| VII-94 | (4-) F | — | (2-) 1-ethyl-4-methyl-5-N(CH₃)₂-1,2,4-triazol-3(4H)-one | OC₂H₅ | logP = 2.21[a] |
| VII-95 | (4-) F | — | (2-) 1-ethyl-4-methyl-5-(OC₃H₇-n)-1,2,4-triazol-3(4H)-one | OC₂H₅ | logP = 2.96[a] |
| VII-96 | (4-) F | — | (2-) 1-ethyl-4-methyl-5-(CH₂OCH₃)-1,2,4-triazol-3(4H)-one | OC₂H₅ | logP = 2.05[a] |
| VII-97 | (4-) F | — | (2-) 1-ethyl-4-cyclopropyl-5-OCH₃-1,2,4-triazol-3(4H)-one | OC₂H₅ | logP = 2.50[a] |
| VII-98 | (4-) F | — | (2-) 1-ethyl-4-cyclopropyl-5-OC₅H₅-1,2,4-triazol-3(4H)-one | OC₂H₅ | logP = 2.89[a] |

TABLE 3-continued

Examples of the compounds of the formula (VII)

| Ex. No. | (position) R³ | (position) (R⁴)ₙ | (position) -A-Z | Y | physical data |
|---|---|---|---|---|---|
| VII-99 | (4-) CF₃ | — | (2-) [2-ethyl-4,4-dimethyl-5-methyl-pyrazol-3(2H)-one] | OC₂H₅ | logP = 2.91[a] |
| VII-100 | (4-) Cl | — | (2-) [2-ethyl-4-methyl-5-methyl-1,2,4-triazol-3(4H)-one] | OC₂H₅ | ¹H-NMR (CDCl₃, δ): 5.39 ppm. |
| VII-101 | (4-) Cl | — | (2-) [2-ethyl-4-methyl-5-CF₃-1,2,4-triazol-3(4H)-one] | OC₂H₅ | ¹H-NMR (CDCl₃, δ): 5.50 ppm. |
| VII-102 | (4-) Cl | — | (2-) [2-ethyl-4-methyl-5-SO₂CH₃-1,2,4-triazol-3(4H)-one] | OC₂H₅ | ¹H-NMR (CDCl₃, δ): 5.49 ppm. |
| VII-103 | (4-) CF₃ | — | (2-) [2-ethyl-4-methyl-5-methyl-1,2,4-triazol-3(4H)-one] | OC₂H₅ | ¹H-NMR (CDCl₃, δ): 5.29 ppm. |
| VII-104 | (4-) CF₃ | — | (2-) [2-ethyl-4-methyl-5-CF₃-1,2,4-triazol-3(4H)-one] | OC₂H₅ | ¹H-NMR (CDCl₃, δ): 5.53 ppm. |
| VII-105 | (4-) CF₃ | — | (2-) [2-ethyl-4-cyclopropyl-5-cyclopropyl-1,2,4-triazol-3(4H)-one] | OC₂H₅ | ¹H-NMR (CDCl₃, δ): 5.34 ppm. |

TABLE 3-continued

Examples of the compounds of the formula (VII)

| Ex. No. | (position) R³ | (position) (R⁴)ₙ | (position) -A-Z | Y | physical data |
|---|---|---|---|---|---|
| VII-106 | (4-) SO₂CH₃ | — | (2-) [1-ethyl-4-cyclopropyl-5-cyclopropyl-1,2,4-triazol-3(4H)-one] | OC₂H₅ | ¹H-NMR (CDCl₃, δ): 5.39 ppm. |
| VII-107 | (4-) SO₂CH₃ | — | (2-) [1-ethyl-4-methyl-5-methyl-1,2,4-triazol-3(4H)-one] | OC₂H₅ | ¹H-NMR (CDCl₃, δ): 5.43 ppm. |
| VII-108 | (4-) SO₂CH₃ | — | (2-) [1-ethyl-4-methyl-5-N(CH₃)₂-1,2,4-triazol-3(4H)-one] | OC₂H₅ | ¹H-NMR (CDCl₃, δ): 5.40 ppm. |
| VII-109 | (4-) SO₂CH₃ | — | (2-) [1-ethyl-4-methyl-5-OC₂H₅-1,2,4-triazol-3(4H)-one] | OC₂H₅ | ¹H-NMR (CDCl₃, δ): 5.38 ppm. |
| VII-110 | (4-) Br | — | (2-) [1-ethyl-4-methyl-5-CF₃-1,2,4-triazol-3(4H)-one] | OC₂H₅ | ¹H-NMR (CDCl₃, δ): 5.49 ppm. |
| VII-111 | — | — | (2-) [1-ethyl-4-cyclopropyl-5-cyclopropyl-1,2,4-triazol-3(4H)-one] | OC₂H₅ | ¹H-NMR (CDCl₃, δ): 5.3 ppm. |
| VII-112 | — | — | (2-) [1-ethyl-4-methyl-5-SCH₃-1,2,4-triazol-3(4H)-one] | OC₂H₅ | ¹H-NMR (CDCl₃, δ): 5.44 ppm. |

TABLE 3-continued

Examples of the compounds of the formula (VII)

| Ex. No. | (position) R³ | (position) (R⁴)ₙ | (position) -A–Z | Y | physical data |
|---|---|---|---|---|---|
| VII-113 | (4-) CF₃ | — | (2-) 1,2-diethyl-4-methyl-1,2,4-triazolidine-3,5-dione | OC₂H₅ | logP = 2.58[a] |
| VII-114 | (4-) SO₂CH₃ | — | (2-) 2-ethyl-4-methyl-5-(methylthio)-2,4-dihydro-3H-1,2,4-triazol-3-one | OCH₃ | logP = 1.53[a] |
| VII-115 | (4-) SO₂CH₃ | — | (2-) 5-ethoxy-2-ethyl-4-methyl-2,4-dihydro-3H-1,2,4-triazol-3-one | OCH₃ | logP = 1.59[a] |
| VII-116 | (4-) I | — | (2-) 5-ethoxy-2-ethyl-4-methyl-2,4-dihydro-3H-1,2,4-triazol-3-one | OCH₃ | logP = 2.68[a] |
| VII-117 | (4-) CF₃ | — | (2-) 5-ethoxy-2-ethyl-4-methyl-2,4-dihydro-3H-1,2,4-triazol-3-one | OCH₃ | logP = 2.74[a] |
| VII-118 | (4-) CF₃ | — | (2-) 2-ethyl-4-methyl-5-(methylthio)-2,4-dihydro-3H-1,2,4-triazol-3-one | OCH₃ | logP = 2.65[a] |
| VII-119 | (4-) CF₃ | — | (2-) 5-bromo-2-ethyl-4-methyl-2,4-dihydro-3H-1,2,4-triazol-3-one | OC₂H₅ | logP = 2.96[a] |

TABLE 3-continued

Examples of the compounds of the formula (VII)

| Ex. No. | (position) R³ | (position) (R⁴)ₙ | (position) -A-Z | Y | physical data |
|---|---|---|---|---|---|
| VII-120 | — | — | (2-) [1,2,4-triazoline-3,5-dione, 1,4-diethyl-2-methyl derivative] | $OCH_3$ | m.p.: 106° C. |
| VII-121 | (4-) $CF_3$ | — | (2-) [N-ethyl benzoxazol-2(3H)-one] | $OCH_3$ | logP = 3.37[a] |
| VII-122 | (4-) $CF_3$ | — | (2-) [N-ethyl benzisothiazol-3(2H)-one 1,1-dioxide] | $OCH_3$ | logP = 3.29[a] |
| VII-123 | (4-) $CF_3$ | — | (2-) [3-ethyl-1,2,3-benzotriazin-4(3H)-one] | $OCH_3$ | logP = 3.26[a] |
| VII-124 | (4-) Cl | (2-) $OCH_3$ | (3-) [1-ethyl-3-methylimidazolidin-2-one] | $OCH_3$ | ¹H-NMR (DMSO-D₆, δ): 4.44 ppm. |
| VII-125 | (4-) Cl | (2-) $OCH_3$ | (3-) [1-ethyl-3-methyltetrahydropyrimidin-2(1H)-one] | $OCH_3$ | ¹H-NMR (DMSO-D₆, δ): 4.66 ppm. |
| VII-126 | (4-) Cl | (2-) $OCH_3$ | (3-) [1-ethyl-4-ethoxy-5-ethyl-1,2,4-triazolin-3-one] | $OCH_3$ | ¹H-NMR (DMSO-D₆, δ): 4.95 ppm. |

The logP values given in Table 3 were determined in accordance with EEC Directive 79/831 Annex V.A8 by HPLC (High Performance Liquid Chromatography) using a reverse-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding data in Table 3 are labelled [a].

(b) Mobile phases for the determination in the neutral range: 0.01 molar aqueous phosphate buffer solution, acetonitrile; linear gradient from 10% acetonitrile to 90% acetonitrile—the corresponding data in Table 3 are labelled b).

Calibration was carried out using unbranched alkan-2-ones (with from 3 to 16 carbon atoms) whose logP values are known (determination of the logP values by the retention times using linear interpolation between two successive alkanones).

The lambda-max values were determined in the maxima of the chromatographic signals, using the UV spectra from 200 nm to 400 nm.

USE EXAMPLES

Example A
Pre-emergence Test

| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 1000 liters of water per hectare.

After three weeks, the degree of damage to the plants is rated in % damage in comparison to the development of the untreated control.

The figures denote:

| 0% | = | no effect (like untreated control) |
| 100% | = | total destruction |

In this test, for example, the compounds of preparation examples 3 and 4 exhibit strong action against weeds, whilst being tolerated well by crop plants, such as, for example, maize.

Example B
Post-emergence Test

| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound such that the particular amounts of active compound desired are applied per unit area. The concentration of the spray liquor is chosen so that the particular amounts of active compound desired are applied in 1000 l of water/ha After three weeks, the degree of damage to the plants is rated in % damage in comparison to the development of the untreated control.

The figures denote:

| 0% | = | no effect (like untreated control) |
| 100% | = | total destruction |

In this test, for example, the compounds of Preparation Examples 3 and 4 exhibit very strong activity against weeds, whilst being tolerated well by crop plants, such as, for example, wheat.

What is claimed is:

1. A compound of the Formula (I),

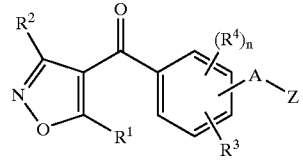

(I)

in which n represents the number 0, 1, 2 or 3,

A represents alkanediyl (alkylene), $R^1$ represents hydrogen or represents in each case optionally substituted alkyl, alkenyl or cycloalkyl, $R^2$ represents hydrogen, cyano, carbamoyl, halogen, or represents in each case optionally substituted alkyl, alkylcarbonyl, alkoxy, alkoxycarbonyl, alkylthio, alkylsulphinyl or alkylsulphonyl, $R^3$ represents hydrogen, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, $R^4$ represents nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, and Z represents an optionally substituted 4- to 12-membered, saturated or unsaturated, monocyclic or bicyclic, heterocyclic grouping which contains 1 to 4 hetero atoms (up to 4 nitrogen atoms and optionally—alternatively or additionally—one oxygen atom or one sulphur atom, or one SO grouping or one $SO_2$ grouping) and which additionally contains one to three oxo groups (C=O) and/or thioxo groups (C=S) as components of the heterocycle.

2. The compound according to claim 1, wherein n represents the number 0, 1 or 2, A represents alkanediyl (alkylene) having 1 to 4 carbon atoms, $R^1$ represents hydrogen, represents optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl having 1 to 6 carbon atoms, represents optionally cyano- or halogen-substituted alkenyl having 2 to 6 carbon atoms, or represents optionally cyano-, halogen- or $C_1$–$C_4$-alkyl-substituted cycloalkyl having 3 to 6 carbon atoms, R² represents hydrogen, cyano, carbamoyl, halogen, represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkylcarbonyl, alkoxy or alkoxycarbonyl having in each case up to 6 carbon atoms, or represents optionally halogen-substituted alkylthio, alkylsulphinyl or alkylsulphonyl having 1 to 6 carbon atoms, R³ represents hydrogen, nitro, cyano, carboxyl, carbamoyl, thiocarbamoyl, halogen, represents in each case optionally halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl or alkylsulphonyl having in each case up to 4 carbon atoms in the alkyl groups, or represents alkylamino, dialkylamino or dialkylaminosulphonyl having in each case up to 4 carbon atoms in the alkyl groups, R⁴ represents nitro, cyano, carboxyl, carbamoyl, thiocarbamoyl, halogen, represents in each case optionally halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl or alkylsulphonyl having in each case up to 4 carbon atoms in the alkyl groups, or represents alkylamino, dialkylamino or dialkylaminosulphonyl having in each case up to 4 carbon atoms in the alkyl groups, and Z represents one of the heterocyclic groupings below -continued

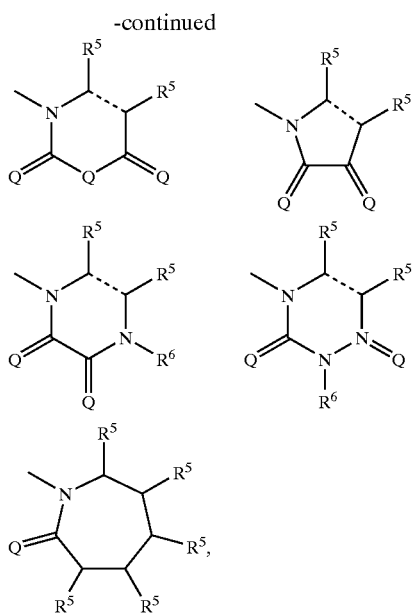

in which the dotted bond is in each case a single bond or a double bond, and each heterocyclic grouping preferably only carries two substituents of the definition $R^5$ and/or $R^6$, Q represents oxygen or sulphur, $R^5$ represents hydrogen, hydroxyl, mercapto, cyano, halogen, represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkylcarbonyl, alkoxy, alkoxycarbonyl, alkylthio, alkylsulphinyl or alkylsulphonyl having in each case up to 6 carbon atoms in the alkyl groups, represents in each case optionally halogen-substituted alkylamino or dialkylamino having in each case up to 6 carbon atoms in the alkyl groups, represents in each case optionally halogen-substituted alkenyl, alkinyl, alkenyloxy, alkenylthio or alkenylamino having in each case up to 6 carbon atoms in the alkenyl or alkinyl groups, represents in each case optionally halogen-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and optionally up to 4 carbon atoms in the alkyl moiety, or represents in each case optionally halogen-, $C_1$–$C_4$-alkyl- or $C_1$–$C_4$-alkoxy-substituted phenyl, phenyloxy, phenylthio, phenylamino, benzyl, benzyloxy, benzylthio or benzylamino, represents pyrrolidino, piperidino or morpholino, or—if two adjacent radicals $R^5$ and $R^5$ are located at a double bond—also together with the adjacent radical $R^5$ represents a benzo grouping, and $R^6$ represents hydrogen, hydroxyl, amino, alkylidenamino having up to 4 carbon atoms, represents in each case optionally halogen- or $C_1$–$C_4$-alkoxy-substituted alkyl, alkoxy, alkylamino, dialkylamino or alkanoylamino having in each case up to 6 carbon atoms in the alkyl groups, represents in each case optionally halogen-substituted alkenyl, alkinyl or alkenyloxy having in each case up to 6 carbon atoms in the alkenyl or alkinyl groups, represents in each case optionally halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents in each case optionally halogen-, $C_1$–$C_4$-alkyl- or $C_1$–$C_4$-alkoxy-substituted phenyl or benzyl, or together with an adjacent radical $R^5$ or $R^6$ represents optionally halogen- or $C_1$–$C_4$-alkyl-substituted alkanediyl having 3 to 5 carbon atoms, where the individual radicals $R^5$ and $R^6$—if a plurality of them are attached to the same heterocyclic grouping—can have identical or different meanings within the scope of the above said definition of said radicals.

3. The compound according to claim 1 wherein

A represents methylene, ethylidene (ethane-1,1-diyl) or dimethylene (ethane-1,2-diyl), $R^1$ represents hydrogen, represents in each case optionally fluorine-, chlorine-, methoxy-, ethoxy-, n- or i-propoxy-, methylthio-, ethylthio-, n- or i-propylthio-, methylsulphinyl-, ethylsulphinyl, n- or i-propylsulphinyl-, methylsulphonyl-, ethylsulphonyl-, n- or i-propylsulphonyl-substituted methyl, ethyl, n- or i-propyl, n-, i-, s- or t-butyl, represents in each case optionally fluorine-, chlorine- or bromine-substituted propenyl, butenyl, propinyl or butinyl, or represents in each case optionally cyano-, fluorine-, chlorine-, bromine-, methyl- or ethyl-substituted cyclopropyl, cyclobutyl, cyclopentyl or cyclohexyl, $R^2$ represents hydrogen, cyano, carbamoyl, fluorine, chlorine, bromine, represents in each case optionally cyano-, fluorine-, chlorine-, methoxy- or ethoxy-substituted methyl, ethyl, n- or i-propyl, acetyl, propionyl, n- or i-butyroyl, methoxy, ethoxy, n- or i-propoxy, methoxycarbonyl, ethoxycarbonyl, n- or i-propoxycarbonyl, or represents in each case optionally fluorine- and/or chlorine-substituted methylthio, ethylthio, n- or i-propylthio, $R^3$ represents hydrogen, nitro, cyano, carboxyl, carbamoyl, thiocarbamoyl, fluorine, chlorine, bromine, iodine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl, $R^4$ represents nitro, cyano, carboxyl, carbamoyl, thiocarbamoyl, fluorine, chlorine, bromine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethyl-sulphonyl, n- or i-propylsulphonyl, or represents methylamino, ethylamino, n- or i-propylamino, dimethylamino, diethylamino, dimethylaminosulphonyl or diethylaminosulphonyl, Z represents one of the groupings

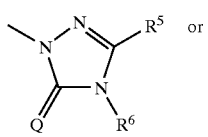
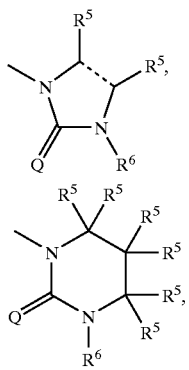

$R^5$ represents hydrogen, hydroxyl, mercapto, cyano, fluorine, chlorine, bromine, iodine, represents in each case optionally fluorine-, chlorine-, methoxy-, ethoxy-, n- or i-propoxy-, n-, i-, s- or t-butoxy-, methylthio-, ethylthio-, n- or i-propylthio-, n-, i-, s- or t-butylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, n-, i-, s- or t-butylamino, dimethylamino, diethylamino, di-n-propylamino or di-i-propylamino, represents in each case optionally fluorine- and/or chlorine-substituted ethenyl, propenyl, butenyl, ethinyl, propinyl, butinyl, propenyloxy, butenyloxy, propenylthio, butenylthio, propenylamino or butenylamino, represents in each case optionally fluorine- and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluorine-, chlorine-, methyl-, ethyl-, n- or i-propyl-, n-, i-, s- or t-butyl-, methoxy-, ethoxy-, n- or i-propoxy-substituted phenyl, phenyloxy, phenylthio, phenylamino, benzyl, benzyloxy, benzylthio or benzylamino, represents pyrrolidino, piperidino or morpholino, or—if two adjacent radicals $R^5$ and $R^5$ are located at a double bond—together with the adjacent radical $R^5$ also represents a benzo grouping, and $R^6$ represents hydrogen, hydroxyl, amino, represents in each case optionally fluorine- and/or chlorine-, methoxy- or ethoxy-substituted methyl, ethyl, n- or i-propyl, n-, i- or s-butyl, methoxy, ethoxy, n- or i-propoxy, methylamino, ethylamino or dimethylamino, represents in each case optionally fluorine- and/or chlorine-substituted ethenyl, propenyl, ethinyl, propinyl or propenyloxy, represents in each case optionally fluorine- and/or chlorine-substituted cyclopropyl, cyclobutyl, cyclopentyl, cyclohexyl, cyclopropylmethyl, cyclobutylmethyl, cyclopentylmethyl, cyclohexylmethyl, or represents in each case optionally fluorine-, chlorine-, methyl-, ethyl-, n- or i-propyl-, n-, i-, s- or t-butyl-, methoxy-, ethoxy-, n- or i-propoxy-substituted phenyl or benzyl, or together with an adjacent radical $R^5$ or $R^6$ represents in each case optionally methyl- and/or ethyl-substituted propane-1,3-diyl (trimethylene) or butane-1,4-diyl (tetramethylene).

4. The compound according to claim 1 wherein $R^1$ represents hydrogen, represents in each case optionally fluorine-, chlorine-, methoxy-, ethoxy-, methylthio-, ethylthio-, methylsulphinyl-, ethylsulphinyl-, methysulphonyl- or ethylsulphonyl-substituted methyl, ethyl, n- or i-propyl, n-, i-, s- or t-butyl, or represents optionally cyano-, fluorine-, chlorine-, bromine-, methyl- or ethyl-substituted cyclopropyl, $R^2$ represents hydrogen, cyano, carbamoyl, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxycarbonyl, ethoxycarbonyl, n- or i-propoxycarbonyl, or represents in each case optionally fluorine- and/or chlorine-substituted methylthio, ethylthio, n- or i-propylthio, $R^3$ represents hydrogen, nitro, cyano, fluorine, chlorine, bromine, iodine, methyl, ethyl, trifluoromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl, $R^4$ represents nitro, cyano, fluorine, chlorine, bromine, methyl, ethyl, trifluoromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl, $R^5$ represents hydrogen, hydroxyl, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, fluoroethyl, chloroethyl, difluoroethyl, dichloroethyl, fluoro-n-propyl, fluoro-i-propyl, chloro-n-propyl, chloro-i-propyl, methoxymethyl, ethoxymethyl, methoxyethyl, ethoxyethyl, methoxy, ethoxy, n- or i-propoxy, n-, i-, s- or t-butoxy, fluoroethoxy, chloroethoxy, difluoroethoxy, dichloroethoxy, trifluoroethoxy, trichloroethoxy, chlorofluoroethoxy, chlorodifluoroethoxy, fluorodichloroethoxy, methylthio, ethylthio, n- or i-propylthio, fluoroethylthio, chloroethylthio, difluoro-ethylthio, dichloroethylthio, chlorofluoroethylthio, chlorodifluoro-ethylthio, fluorodichloroethylthio, methylsulphinyl, ethylsulphinyl, n- or i-propylsulphinyl, methylsulphonyl, ethylsulphonyl, n- or i-propylsulphonyl, dimethylamino, propenylthio, butenylthio, propinylthio, butinylthio, cyclopropyl, cyclopropylmethyl, cyclopropylmelhoxy, phenyl or phenoxy, and $R^6$ represents amino, methyl, ethyl, n- or i-propyl, n-, i-, s- or t-butyl, methoxy, ethoxy, methylamino, dimethylamino, cyclopropyl or cyclopropylmethyl, or together with $R^5$ represents propane-1,3-diyl (trimethylene), butane-1,4-diyl (tetramethylene) or pentane-1,5-diyl (pentamethylene).

5. The compound according to claim 1 wherein A represents methylene.

6. The compound according to claim 2 wherein Q represents oxygen (O).

7. The compound according to claim 1 wherein $R^1$ represents cyclopropyl.

8. The compound according to claim 1 wherein $R^2$ represents hydrogen, methoxycarbonyl or ethoxycarbonyl.

9. The compound according to claim 2 wherein $R^6$ represents methyl, dimethylamino or cyclopropyl.

10. The compound according to claim 1 wherein $R^3$ represents chlorine, bromine, cyano, trifluoromethyl or methylsulphonyl.

11. The compound according to claim 1 wherein $R^4$ represents cyano, chlorine, nitro, methyl, trifluoromethyl, methoxy or methylsulphonyl.

12. A compound of the Formula (IA)

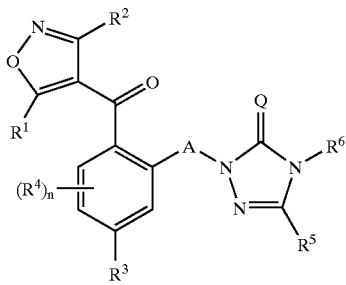

in which
n, A, Q, $R^1$, $R^2$, $R^3$, $R^4$, $R^5$ and $R^6$ are each as defined in claim 2.

13. A compound of the Formula (IB)

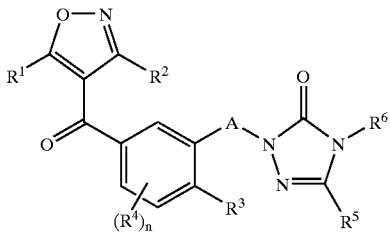

in which
n, A, Q, $R^1$, $R^2$, $R^3$, $R^4$, $R^5$ and $R^6$ are each as defined in claim 2.

14. A compound of the Formula (IC)

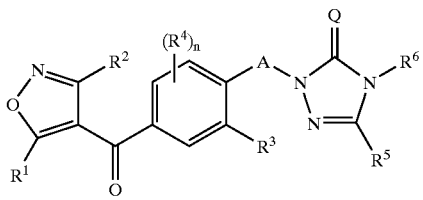

in which
n, A, Q, $R^1$, $R^2$, $R^3$, $R^4$, $R^5$ and $R^6$ are each as defined in claim 2.

15. A process for preparing a compound of the Formula (I) according to claim 1 wherein (a) a benzoylisoxazole of the Formula (II)

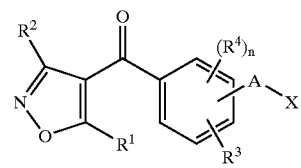

in which
n, A, $R^1$, $R^2$, $R^3$ and $R^4$ are each as defined in claim 1 and
X represents halogen
is reacted with a heterocycle of the Formula (III)

$$H-Z \qquad (III)$$

in which
Z is as defined in claim 1,
optionally in the presence of one or more reaction auxiliaries and optionally in the presence of one or more diluents,
or that
if $R^2$ is hydrogen
(b) a benzoyl ketone of the Formula (IV)

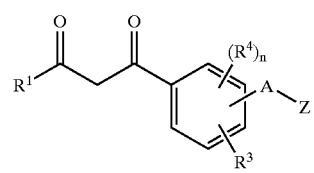

in which
n, A, $R^1$, $R^3$, $R^4$ and Z are each as defined in claim 1
is reacted with a compound selected from the group consisting of an orthoformic ester and an N,N-dimethylformamide acetal
and are subsequently reacted with hydroxylamine or an acid adduct thereof,
optionally in the presence of one or more reaction auxiliaries and optionally in the presence of one or more diluents,
or that
if $R^2$ represents optionally substituted alkoxycarbonyl
(c) a benzoyl ketone of the Formula (IV)

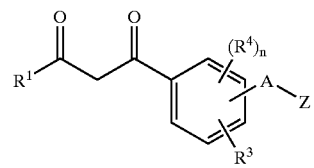

in which
n, A, $R^1$, $R^3$, $R^4$ and Z are each as defined in claim 1 is reacted with a cyanoformic ester and then hydroxylamine, or an acid adduct of hydroxylamine, or are reacted with an alkyl chloro-hydroximino-acetate,
optionally in the presence of one or more reaction auxiliaries and optionally in the presence of one or more diluents, or that
if $R^2$ represents alkylthio
(d) a benzoyl ketone of the Formula (IV)

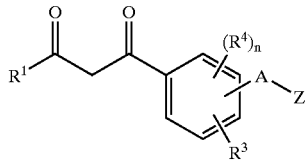
(IV)

in which
n, A, $R^1$, $R^3$, $R^4$ and Z are each as defined in claim 1
is reacted with carbon disulphide and with an alkylating agent
and then with hydroxylamine or an acid adduct thereof,
optionally in the presence of one or more reaction auxiliaries and optionally in the presence of one or more diluents, and further optionally comprising the step of conducting electrophilic or nucleophilic substitutions and/or oxidations or reductions on the compounds of the Formula (I) obtained according to one of said processes (a) to (d).

16. An herbicidal composition comprising at least one compound according to claim 1 and an extender.

17. A method for controlling undesirable plants comprising applying an effective amount of a compound of the Formula (I) according to claim 1 to one or more members selected from the group consisting of said plants and a habitat of said plants.

* * * * *